(12) United States Patent
Sherman et al.

(10) Patent No.: US 11,096,801 B2
(45) Date of Patent: Aug. 24, 2021

(54) ORTHOPAEDIC SURGICAL SYSTEM FOR DETERMINING JOINT FORCES OF A PATIENT'S KNEE JOINT

(71) Applicant: DEPUY IRELAND UNLIMITED COMPANY, County Cork (IE)

(72) Inventors: Jason T. Sherman, Warsaw, IN (US); Michael J. Rock, Leeds (GB); Daren L. Deffenbaugh, Winona Lake, IN (US); Kyle S. Moore, Acushnet, MA (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 226 days.

(21) Appl. No.: 16/269,041

(22) Filed: Feb. 6, 2019

(65) Prior Publication Data

US 2019/0167448 A1    Jun. 6, 2019

Related U.S. Application Data

(62) Division of application No. 13/436,854, filed on Mar. 31, 2012, now Pat. No. 10,206,792.

(51) Int. Cl.
*A61F 2/46* (2006.01)
*A61B 17/02* (2006.01)
*A61B 90/00* (2016.01)

(52) U.S. Cl.
CPC .......... *A61F 2/4684* (2013.01); *A61B 17/025* (2013.01); *A61F 2/4657* (2013.01);
(Continued)

(58) Field of Classification Search
CPC .................. A61F 2/4684; A61F 2/4657; A61F 2002/4461; A61F 2002/4666; A61F 2/389;
(Continued)

(56) References Cited

U.S. PATENT DOCUMENTS 4,501,266 A    2/1985  McDaniel
4,566,448 A    1/1986  Rohr
(Continued)

FOREIGN PATENT DOCUMENTS

CN    101156810 A    4/2008
CN    101849864 A    10/2010
(Continued)

OTHER PUBLICATIONS

Translation of Japanese Office Action, Japanese Application No. 2013-072732, dated Feb. 21, 2017, 5 pages.
(Continued)

*Primary Examiner* — Patrick Fernandes
(74) *Attorney, Agent, or Firm* — Barnes & Thornburg LLP

(57) ABSTRACT

An orthopaedic surgical system includes a sensor module for determining the joint force of a patient's knee joint and an adaptor for coupling various tibial trialing components to the sensor module. The sensor module includes a tibial paddle to which the adaptor is configured to couple. The adaptor and tibial paddle include structures that control the orientation at which the adaptor is attachable to the tibial paddle. Some tibial trialing components may be positioned over the adaptor in a mobile orientation that facilities rotation of the tibial trialing component relative to the tibial paddle or a fixed orientation that restricts the rotation of the tibial trialing component.

20 Claims, 32 Drawing Sheets

(52) U.S. Cl.
CPC . *A61B 2017/0268* (2013.01); *A61B 2090/061* (2016.02); *A61B 2090/064* (2016.02); *A61B 2090/065* (2016.02); *A61F 2002/4661* (2013.01); *A61F 2002/4666* (2013.01)

(58) Field of Classification Search
CPC ........ A61F 2/38; A61F 2/3859; A61B 17/025; A61B 2090/064; A61B 2090/061; A61B 2090/065; A61B 2017/0268; A61B 17/155; A61B 17/1764
See application file for complete search history.

(56) References Cited

U.S. PATENT DOCUMENTS

| | | | |
|---|---|---|---|
| 4,576,309 A | 3/1986 | Tzifansky et al. |
| 4,795,473 A | 1/1989 | Grimes |
| 4,796,610 A | 1/1989 | Cromartie |
| 4,804,000 A | 2/1989 | Lamb |
| 4,808,186 A | 2/1989 | Smith |
| 4,822,362 A | 4/1989 | Walker |
| 4,825,857 A | 5/1989 | Kenna |
| 4,828,562 A | 5/1989 | Kenna |
| 4,834,057 A | 5/1989 | McLeod |
| 4,856,993 A | 8/1989 | Maness et al. |
| 4,888,021 A | 12/1989 | Forte |
| 4,892,093 A | 1/1990 | Zarmowski |
| 4,892,546 A | 1/1990 | Kotz |
| 4,899,761 A | 2/1990 | Brown et al. |
| 4,907,578 A | 3/1990 | Petersen |
| 4,926,847 A | 5/1990 | Luckman |
| 4,932,974 A | 6/1990 | Pappas |
| 4,935,023 A | 6/1990 | Whiteside |
| 4,936,853 A | 6/1990 | Fabian et al. |
| 4,938,762 A | 7/1990 | Wehrli |
| 4,944,756 A | 7/1990 | Kenna |
| 4,959,071 A | 9/1990 | Brown |
| 4,963,153 A | 10/1990 | Noesberger |
| 4,973,331 A | 11/1990 | Pursley et al. |
| 4,979,949 A | 12/1990 | Matsen et al. |
| 4,986,281 A | 1/1991 | Preves et al. |
| 5,002,547 A | 3/1991 | Poggie et al. |
| 5,018,514 A | 5/1991 | Grood et al. |
| 5,020,797 A | 6/1991 | Burns |
| 5,032,132 A | 7/1991 | Matsen |
| 5,033,291 A | 7/1991 | Podoloff et al. |
| 5,037,423 A | 8/1991 | Kenna |
| 5,056,530 A | 10/1991 | Butler et al. |
| 5,080,675 A | 1/1992 | Lawes et al. |
| 5,082,003 A | 1/1992 | Lamb et al. |
| 5,098,436 A | 3/1992 | Ferrante et al. |
| 5,122,144 A | 6/1992 | Bert |
| 5,125,408 A | 6/1992 | Basser |
| 5,129,909 A | 7/1992 | Sutherland |
| 5,133,660 A | 7/1992 | Fenick |
| 5,197,488 A | 3/1993 | Kovacevic |
| 5,207,711 A | 5/1993 | Caspari et al. |
| 5,213,112 A | 5/1993 | Niwa |
| 5,228,459 A | 7/1993 | Caspari et al. |
| 5,234,433 A | 8/1993 | Bert |
| 5,234,434 A | 8/1993 | Gable |
| 5,234,435 A | 8/1993 | Seagrave |
| 5,236,432 A | 8/1993 | Matsen et al. |
| 5,250,050 A | 10/1993 | Poggie et al. |
| 5,257,996 A | 11/1993 | McGuire |
| 5,312,411 A | 5/1994 | Steele et al. |
| 5,320,529 A | 6/1994 | Pompa |
| 5,326,363 A | 7/1994 | Aikins |
| 5,329,933 A | 7/1994 | Graf |
| 5,342,367 A | 8/1994 | Ferrante et al. |
| 5,358,527 A | 10/1994 | Forte |
| 5,360,016 A | 11/1994 | Kovacevic |
| 5,364,401 A | 11/1994 | Ferrante |
| 5,364,402 A | 11/1994 | Mumme |
| 5,395,401 A | 3/1995 | Bahler |
| 5,403,319 A | 4/1995 | Matsen et al. |
| 5,417,694 A | 5/1995 | Marik et al. |
| 5,423,334 A | 6/1995 | Jordan |
| 5,425,775 A | 6/1995 | Kovacevic |
| 5,431,652 A | 7/1995 | Shimamoto et al. |
| 5,431,653 A | 7/1995 | Callaway |
| 5,443,518 A | 8/1995 | Insall |
| 5,456,724 A | 10/1995 | Yen et al. |
| 5,470,354 A | 11/1995 | Hershberger |
| 5,489,311 A | 2/1996 | Cipolletti |
| 5,496,352 A | 3/1996 | Renger |
| 5,514,144 A | 5/1996 | Bolton |
| 5,514,183 A | 5/1996 | Epstein |
| 5,520,695 A | 5/1996 | Luckman |
| 5,540,696 A | 7/1996 | Booth et al. |
| 5,562,674 A | 10/1996 | Stalcup et al. |
| 5,569,261 A | 10/1996 | Marik et al. |
| 5,571,110 A | 11/1996 | Matsen et al. |
| 5,571,197 A | 11/1996 | Insall |
| 5,597,379 A | 1/1997 | Haines |
| 5,611,774 A | 3/1997 | Postelmans |
| 5,613,971 A | 3/1997 | Lower |
| 5,630,820 A | 5/1997 | Todd |
| 5,643,272 A | 7/1997 | Haines |
| 5,649,929 A | 7/1997 | Callaway |
| 5,656,785 A | 8/1997 | Trainor et al. |
| 5,658,293 A | 8/1997 | Vanlaningham |
| 5,669,914 A | 9/1997 | Eckoff |
| 5,671,695 A | 9/1997 | Schroeder |
| 5,682,886 A | 11/1997 | Delp et al. |
| 5,683,397 A | 11/1997 | Vendrely et al. |
| 5,688,280 A | 11/1997 | Booth, Jr. et al. |
| 5,688,282 A | 11/1997 | Baron et al. |
| 5,690,635 A | 11/1997 | Matsen et al. |
| 5,702,422 A | 12/1997 | Stone |
| 5,702,463 A | 12/1997 | Pothier et al. |
| 5,733,292 A | 3/1998 | Gustilo et al. |
| 5,735,904 A | 4/1998 | Pappas |
| 5,743,909 A | 4/1998 | Collette |
| 5,768,134 A | 6/1998 | Swaelens et al. |
| 5,769,894 A | 6/1998 | Ferragamo |
| 5,782,925 A | 7/1998 | Collazo et al. |
| 5,800,438 A | 9/1998 | Tuke |
| 5,800,552 A | 9/1998 | Forte |
| 5,810,827 A | 9/1998 | Haines |
| 5,824,085 A | 10/1998 | Sahay et al. |
| 5,824,104 A | 10/1998 | Tuke |
| 5,840,047 A | 11/1998 | Stedham |
| 5,860,980 A | 1/1999 | Axelson et al. |
| 5,871,018 A | 2/1999 | Delp et al. |
| 5,879,389 A | 3/1999 | Koshino |
| 5,880,976 A | 3/1999 | DiGioia, III et al. |
| 5,891,150 A | 4/1999 | Chan |
| 5,911,723 A | 6/1999 | Ashby |
| 5,931,777 A | 8/1999 | Sava |
| 5,935,086 A | 8/1999 | Beacon et al. |
| 5,976,147 A | 11/1999 | LaSalle et al. |
| 6,013,103 A | 1/2000 | Kaufman et al. |
| 6,019,767 A | 2/2000 | Howell |
| 6,022,377 A | 2/2000 | Nuelle et al. |
| 6,034,296 A | 3/2000 | Elvin et al. |
| 6,046,752 A | 5/2000 | Roger |
| 6,056,754 A | 5/2000 | Haines |
| 6,056,756 A | 5/2000 | Eng et al. |
| 6,080,154 A | 6/2000 | Reay-Young et al. |
| 6,086,592 A | 7/2000 | Rosenberg |
| 6,096,043 A | 8/2000 | Techiera et al. |
| 6,102,952 A | 8/2000 | Koshino |
| 6,113,604 A | 9/2000 | Whittaker et al. |
| 6,126,692 A | 10/2000 | Robie et al. |
| 6,165,142 A | 12/2000 | Bar |
| 6,174,294 B1 | 1/2001 | Crabb et al. |
| 6,210,638 B1 | 4/2001 | Grieco et al. |
| 6,327,491 B1 | 12/2001 | Franklin et al. |
| 6,447,448 B1 | 9/2002 | Ishikawa et al. |
| 6,488,711 B1 | 12/2002 | Grafinger |
| 6,540,787 B2 | 4/2003 | Biegun et al. |
| 6,553,681 B2 | 4/2003 | Ekholm, Jr. et al. |
| 6,565,570 B2 | 5/2003 | Sterett et al. |

(56) References Cited

U.S. PATENT DOCUMENTS

| | | |
|---|---|---|
| 6,575,980 B1 | 6/2003 | Robie et al. |
| 6,589,283 B1 | 7/2003 | Metzger |
| 6,610,096 B2 | 8/2003 | MacDonald |
| 6,632,225 B2 | 10/2003 | Sanford et al. |
| 6,645,215 B1 | 11/2003 | McGovern et al. |
| 6,648,896 B2 | 11/2003 | Overes |
| 6,702,821 B2 | 3/2004 | Bonutti |
| 6,706,005 B2 | 3/2004 | Roy et al. |
| 6,758,850 B2 | 7/2004 | Smith et al. |
| 6,770,078 B2 | 8/2004 | Bonutti |
| 6,821,299 B2 | 11/2004 | Kirking et al. |
| 6,827,723 B2 | 12/2004 | Carson |
| 6,856,834 B2 | 2/2005 | Treppo et al. |
| 6,905,513 B1 | 6/2005 | Metzger |
| 6,923,817 B2 | 8/2005 | Carson |
| 6,972,039 B2 | 12/2005 | Metzger et al. |
| 6,974,481 B1 | 12/2005 | Carson |
| 6,984,249 B2 | 1/2006 | Keller |
| 7,104,996 B2 | 9/2006 | Bonutti |
| 7,153,281 B2 | 12/2006 | Holmes |
| 7,232,416 B2 | 6/2007 | Czernicki |
| 7,275,218 B2 | 9/2007 | Petrella et al. |
| 7,333,013 B2 | 2/2008 | Berger |
| 7,362,228 B2 | 4/2008 | Nycz et al. |
| 7,412,897 B2 | 8/2008 | Crottet et al. |
| 7,544,211 B2 | 6/2009 | Rochetin |
| 7,559,931 B2 | 7/2009 | Stone |
| 7,575,602 B2 | 8/2009 | Amirouche et al. |
| 7,604,665 B2 | 10/2009 | Iannotti et al. |
| 7,615,055 B2 | 11/2009 | Stefanchik et al. |
| 7,632,283 B2 | 12/2009 | Heldreth |
| 7,794,499 B2 | 9/2010 | Navarro et al. |
| 7,849,751 B2 | 12/2010 | Clark et al. |
| 7,892,236 B1 | 2/2011 | Bonutti |
| 7,894,872 B2 | 2/2011 | Sherman |
| 7,932,825 B2 | 4/2011 | Berger |
| 8,082,162 B2 | 12/2011 | Flood |
| 8,112,175 B2 | 2/2012 | Handfield et al. |
| 8,118,815 B2 | 2/2012 | van der Walt |
| 8,551,023 B2 | 10/2013 | Sherman et al. |
| 9,538,953 B2 | 1/2017 | Sherman et al. |
| 10,182,867 B2 | 1/2019 | Iannotti et al. |
| 10,918,442 B2 | 2/2021 | Iannotti et al. |
| 2001/0021877 A1 | 9/2001 | Biegun et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0133175 A1 | 9/2002 | Carson |
| 2002/0147455 A1 | 10/2002 | Carson |
| 2002/0156480 A1 | 10/2002 | Overes et al. |
| 2003/0028196 A1 | 2/2003 | Bonutti |
| 2003/0069591 A1 | 4/2003 | Carson et al. |
| 2003/0069644 A1 | 4/2003 | Kovacevic et al. |
| 2003/0130665 A1 | 7/2003 | Pinczewski et al. |
| 2003/0139645 A1 | 7/2003 | Adelman |
| 2003/0144669 A1 | 7/2003 | Robinson |
| 2003/0153978 A1 | 8/2003 | Whiteside |
| 2003/0187452 A1 | 10/2003 | Smith et al. |
| 2003/0236472 A1 | 12/2003 | Van Hoeck et al. |
| 2004/0019382 A1 | 1/2004 | Amirouche et al. |
| 2004/0064073 A1 | 4/2004 | Heldreth |
| 2004/0064191 A1 | 4/2004 | Wasielewski |
| 2004/0097951 A1 | 5/2004 | Steffensmeier |
| 2004/0122441 A1 | 6/2004 | Muratsu |
| 2004/0153091 A1 | 8/2004 | Figueroa et al. |
| 2004/0243148 A1 | 12/2004 | Wasielewski |
| 2005/0010302 A1 | 1/2005 | Dietz et al. |
| 2005/0021044 A1 | 1/2005 | Stone et al. |
| 2005/0038442 A1 | 2/2005 | Freeman |
| 2005/0085920 A1 | 4/2005 | Williamson |
| 2005/0113846 A1 | 5/2005 | Carson |
| 2005/0149041 A1 | 7/2005 | McGinley et al. |
| 2005/0177169 A1 | 8/2005 | Fisher et al. |
| 2005/0177170 A1 | 8/2005 | Fisher et al. |
| 2005/0177173 A1 | 8/2005 | Aebi et al. |
| 2005/0234332 A1 | 10/2005 | Murphy |
| 2005/0234448 A1 | 10/2005 | McCarthy |
| 2005/0234461 A1 | 10/2005 | Burdulis et al. |
| 2005/0234465 A1 | 10/2005 | McCombs et al. |
| 2005/0234466 A1 | 10/2005 | Stallings |
| 2005/0234468 A1 | 10/2005 | Carson |
| 2005/0247319 A1 | 11/2005 | Berger |
| 2005/0251026 A1 | 11/2005 | Stone |
| 2005/0256527 A1 | 11/2005 | Delfosse et al. |
| 2005/0261071 A1 | 11/2005 | Cameron |
| 2005/0267485 A1 | 12/2005 | Cordes et al. |
| 2006/0012736 A1 | 1/2006 | Nishino et al. |
| 2006/0081063 A1 | 4/2006 | Neubauer et al. |
| 2006/0149277 A1 | 7/2006 | Cinquin et al. |
| 2006/0161051 A1 | 7/2006 | Terrill-Grisoni et al. |
| 2006/0219776 A1 | 10/2006 | Finn |
| 2006/0224088 A1 | 10/2006 | Roche |
| 2006/0232408 A1 | 10/2006 | Nycz et al. |
| 2006/0241569 A1 | 10/2006 | DiSilvestro |
| 2006/0271056 A1 | 11/2006 | Terrill-Grisoni et al. |
| 2007/0162142 A1 | 7/2007 | Stone |
| 2007/0219561 A1 | 9/2007 | Lavallee et al. |
| 2007/0233144 A1 | 10/2007 | Lavallee |
| 2007/0239165 A1 | 10/2007 | Amirouche |
| 2007/0244488 A1 | 10/2007 | Metzger et al. |
| 2008/0051892 A1 | 2/2008 | Malandain |
| 2008/0091272 A1 | 4/2008 | Aram et al. |
| 2008/0114463 A1 | 5/2008 | Auger et al. |
| 2008/0133022 A1 | 6/2008 | Caylor |
| 2008/0306413 A1 | 12/2008 | Crottet et al. |
| 2009/0005708 A1 | 1/2009 | Johanson et al. |
| 2009/0018544 A1 | 1/2009 | Heavener |
| 2009/0088674 A1 | 4/2009 | Caillouette et al. |
| 2009/0088760 A1 | 4/2009 | Aram et al. |
| 2009/0099570 A1 | 4/2009 | Paradis et al. |
| 2009/0138019 A1 | 5/2009 | Wasielewski |
| 2009/0138021 A1 | 5/2009 | Colquhoun |
| 2009/0266728 A1 | 10/2009 | Turner et al. |
| 2009/0270869 A1 | 10/2009 | Colquhoun et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0326544 A1 | 12/2009 | Chessar et al. |
| 2010/0016705 A1 | 1/2010 | Stone |
| 2010/0063508 A1 | 3/2010 | Borja et al. |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0137869 A1 | 6/2010 | Borja et al. |
| 2010/0137871 A1 | 6/2010 | Borja |
| 2010/0194541 A1 | 8/2010 | Stevenson et al. |
| 2010/0198275 A1 | 8/2010 | Chana et al. |
| 2010/0217156 A1 | 8/2010 | Fisher et al. |
| 2010/0249533 A1 | 9/2010 | Pierce et al. |
| 2010/0249658 A1 | 9/2010 | Sherman et al. |
| 2010/0249659 A1 | 9/2010 | Sherman et al. |
| 2010/0249660 A1 | 9/2010 | Sherman et al. |
| 2010/0249777 A1 | 9/2010 | Sherman et al. |
| 2010/0249789 A1 | 9/2010 | Rock et al. |
| 2010/0250571 A1 | 9/2010 | Pierce et al. |
| 2011/0066079 A1 | 3/2011 | Otto et al. |
| 2013/0006252 A1 | 1/2013 | Waite, II et al. |
| 2013/0006253 A1 | 1/2013 | Waite, II et al. |
| 2013/0006370 A1 | 1/2013 | Wogoman et al. |
| 2013/0006371 A1 | 1/2013 | Wogoman et al. |
| 2013/0006377 A1 | 1/2013 | Waite, II et al. |
| 2013/0261502 A1 | 10/2013 | Sherman et al. |
| 2013/0261503 A1 | 10/2013 | Sherman et al. |
| 2013/0261505 A1 | 10/2013 | Sherman et al. |
| 2014/0018707 A1 | 1/2014 | Sherman et al. |

FOREIGN PATENT DOCUMENTS

| | | |
|---|---|---|
| DE | 857860 C | 12/1952 |
| DE | 10335410 A1 | 2/2005 |
| EP | 0645987 | 4/1995 |
| EP | 0720834 B1 | 6/1999 |
| EP | 1129676 | 9/2001 |

(56) References Cited

FOREIGN PATENT DOCUMENTS

| | | |
|---|---|---|
| EP | 1245193 | 10/2002 |
| EP | 1348382 A2 | 10/2003 |
| EP | 1402857 A2 | 3/2004 |
| EP | 1645229 | 4/2006 |
| EP | 1707159 B1 | 11/2008 |
| EP | 1402857 B1 | 8/2010 |
| EP | 1915951 B1 | 6/2011 |
| FR | 2897528 A1 | 8/2007 |
| JP | 2001293003 A | 10/2001 |
| JP | 2010063783 A | 3/2010 |
| WO | 7900739 | 10/1979 |
| WO | 93/25157 A1 | 12/1993 |
| WO | 1996017552 A1 | 6/1996 |
| WO | 9935972 | 7/1999 |
| WO | 0078225 A1 | 12/2000 |
| WO | 03065949 A2 | 8/2003 |
| WO | 2004008988 A2 | 1/2004 |
| WO | 2005023120 A1 | 3/2005 |
| WO | 2005037671 A2 | 4/2005 |
| WO | 2005089681 A | 9/2005 |
| WO | 2007036694 A1 | 4/2007 |
| WO | 2007036699 | 4/2007 |
| WO | 2010/011978 A1 | 1/2010 |
| WO | 2010022272 A1 | 2/2010 |
| WO | 2010/030809 A1 | 3/2010 |
| WO | 2012004580 A1 | 1/2012 |
| WO | 2013044174 A2 | 3/2013 |

OTHER PUBLICATIONS

European Search Report for European Patent Application No. 14161315.8-1654, dated Jun. 16, 2014, 5 pages.

European Search Report for European Patent Application No. 113161813.4-1654, dated Jun. 11, 2013, 5 pages.

Coordinate Ultra Revision Knee System, Surgical Technique, 1997, p. 24.

GMK Revision, Surgical Technique, Ref. 99.27.12US rev. 1, 1999, 74 pages.

P.F.C. Sigma Knee System, Revision, Surgical Technique, 2000, p. 66.

P.F.C. Sigma Rotating Platform Knee System with M.B.T. Tray, Primary Procedure with a Curved or Posterior Stabilized Implant, 2003, 43 pages.

Smith & Nephew, Legion, Revision Knee System, Surgical Technique, 2005, 40 pages.

PFC Sigma RP-F, Specialist 2 Instruments, Surgical Technique, Performance in Flexion, 2007, 32 pages.

Sigma High Performance Instruments, Design Rationale, 2007, 12 pages.

Biomet, Vanguard SSK, Revision System, Surgical Technique, Feb. 2008, 64 pages.

LCS High Performance Instruments, Surgical Technique, 2008, 44 pages.

DePuy Orthopaedics, Inc., Sigma Revision and M.B.T. Revision Tray, Surgical Technique, 2008, 82 pages.

Zimmer NexGen LCCK, Surgical Technique for use with LCCK 4-in-1 Instrument, 2009, 52 pages.

Sigma High Performance Instruments, Classic Surgical Technique, 2010, 52 pages.

Sigma Revision and M.B.T. Revision Tray, Surgical Technique, 2012, p. 84.

S-Rom Noiles Rotating Hinge, Surgical Technique, 2012, p. 76.

Attune Knee System Surgical Technique, 2013, 73 pages.

Translation of Chinese Search Report and Text of First Office Action, Chinese Application No. 201310110962.8, dated Mar. 7, 2016, 5 pages.

European Search Report for Eureopean Patent Application No. 06251808.9-2310, dated Jul. 14, 2006, 7 pgs.

European Search Report for European Patent Application No. 10156105.8-2319, dated Jun. 15, 2010, 8 pgs.

| MEDIAL-LATERAL BALANCE | | | | BALANCE | | | | |
|---|---|---|---|---|---|---|---|---|
| % MEDIAL | | % LATERAL | | 80 | 82 | 84 | 86 | 88 |
| TO | FROM | FROM | TO | | | | | |
| 100% | 85% | 0% | 15% | ON | OFF | OFF | OFF | OFF |
| 84% | 75% | 16% | 25% | ON | ON | OFF | OFF | OFF |
| 74% | 65% | 26% | 35% | OFF | ON | OFF | OFF | OFF |
| 64% | 55% | 36% | 45% | OFF | ON | ON | OFF | OFF |
| 54% | 46% | 46% | 54% | OFF | OFF | ON | OFF | OFF |
| 45% | 36% | 55% | 64% | OFF | OFF | ON | ON | OFF |
| 35% | 26% | 65% | 74% | OFF | OFF | OFF | ON | OFF |
| 25% | 16% | 75% | 84% | OFF | OFF | OFF | ON | ON |
| 15% | 0% | 85% | 100% | OFF | OFF | OFF | OFF | ON |

FIG. 7

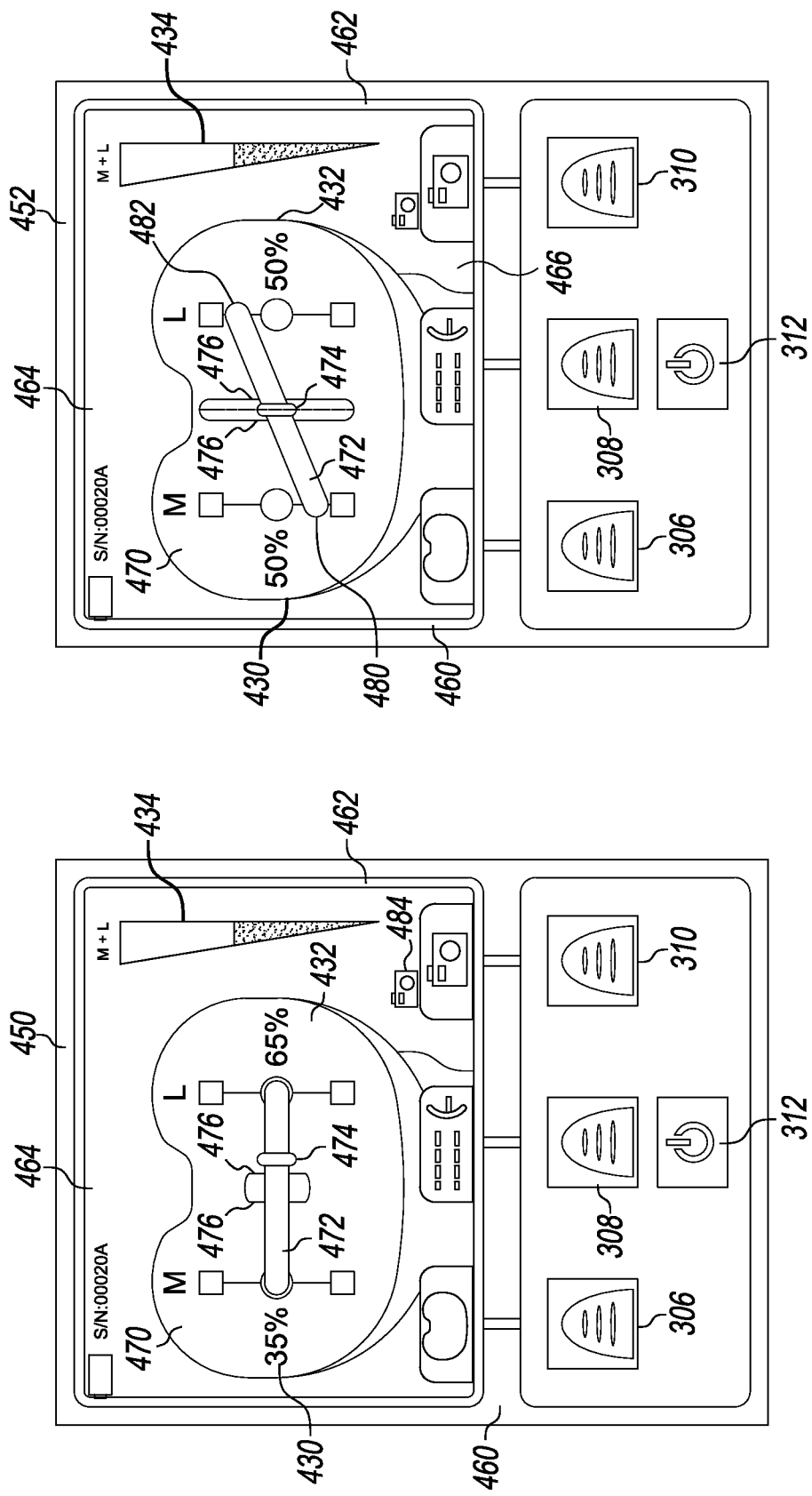

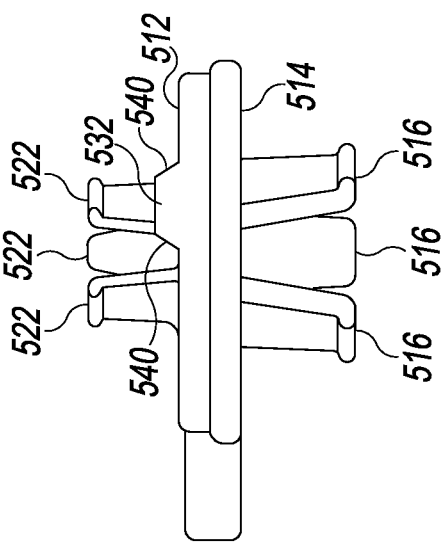
FIG. 20C
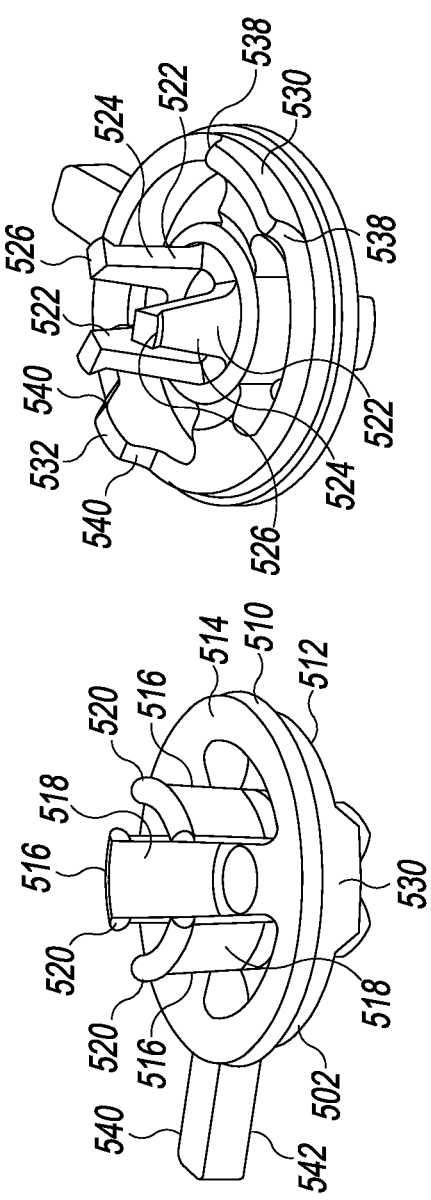
FIG. 20A
FIG. 20B
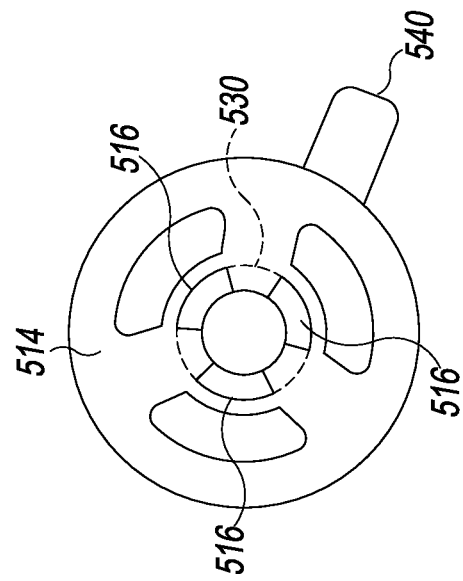
FIG. 20E
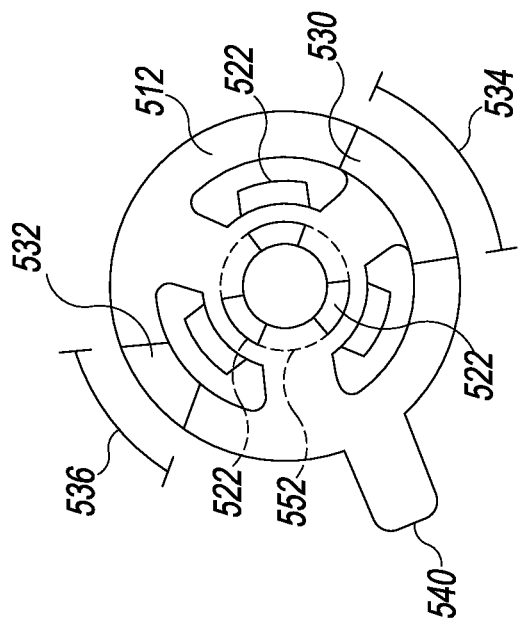
FIG. 20D

US 11,096,801 B2

ORTHOPAEDIC SURGICAL SYSTEM FOR DETERMINING JOINT FORCES OF A PATIENT'S KNEE JOINT

This application is a divisional application under 35 U.S.C. § 121 claiming priority to U.S. patent application Ser. No. 13/436,854, now U.S. Pat. No. 10,206,792, filed Mar. 31, 2012, which is expressly incorporated herein by reference.

CROSS-REFERENCE TO RELATED U.S. PATENT APPLICATION(S)

Cross-reference is made to U.S. Utility patent application Ser. No. 13/436,855, now U.S. Pat. No. 10,070,973, entitled "ORTHOPAEDIC SENSOR MODULE AND SYSTEM FOR DETERMINING JOINT FORCES OF A PATIENT'S KNEE JOINT," by Jason T. Sherman, which was filed on Mar. 31, 2012; to U.S. Utility patent application Ser. No. 13/436,859, now U.S. Pat. No. 10,098,761, entitled "SYSTEM AND METHOD FOR VALIDATING AN ORTHOPAEDIC SURGICAL PLAN," by Jason T. Sherman, which was filed on Mar. 31, 2012; to U.S. Utility patent application Ser. No. 12/415,225, now U.S. Pat. No. 8,556,830, entitled "DEVICE AND METHOD FOR DISPLAYING JOINT FORCE DATA" by Jason T. Sherman, which was filed on Mar. 31, 2009; to U.S. Utility patent application Ser. No. 12/415,290, now U.S. Pat. No. 8,721,568, entitled "METHOD FOR PERFORMING AN ORTHOPAEDIC SURGICAL PROCEDURE" by Mick Rock, which was filed on Mar. 31, 2009; to U.S. Utility patent application Ser. No. 12/415,172, now U.S. Pat. No. 8,551,023, entitled "DEVICE AND METHOD FOR DETERMINING FORCES OF A PATIENT'S JOINT" by Jason T. Sherman, which was filed on Mar. 31, 2009; to U.S. Utility patent application Ser. No. 12/415,365, now U.S. Pat. No. 8,597,210, entitled "SYSTEM AND METHOD FOR DISPLAYING JOINT FORCE DATA" by Jason Sherman, which was filed on Mar. 31, 2009; and to U.S. Utility patent application Ser. No. 12/415,350, now U.S. Pat. No. 8,740,817, entitled "DEVICE AND METHOD FOR DETERMINING FORCES OF A PATIENT'S KNEE JOINT" by Jason T. Sherman, which was filed on Mar. 31, 2009; the entirety of each of which is incorporated herein by reference.

TECHNICAL FIELD

The present disclosure relates generally to orthopaedic surgical instruments and, more particularly, to systems, devices, and methods for determining and displaying joint force data.

BACKGROUND

Orthopaedic prostheses are implanted in patients by orthopaedic surgeons to, for example, correct or otherwise alleviate bone and/or soft tissue loss, trauma damage, and/or deformation of the bone(s) of the patients. Orthopaedic prostheses may replace a portion or the complete joint of a patient. For example, the orthopaedic prosthesis may replace the patient's knee, hip, shoulder, ankle, or other joint. In the case of a knee replacement, the orthopaedic knee prosthesis may include a tibial tray, a femoral component, and a polymer insert or bearing positioned between the tibial tray and the femoral component. In some cases, the knee prosthesis may also include a prosthetic patella component, which is secured to a posterior side of the patient's surgically-prepared patella.

During the orthopaedic surgical procedure, a surgeon initially prepares the patient's bone(s) to receive the orthopaedic prosthesis. For example, in the case of a knee replacement orthopaedic surgical procedure, the surgeon may resect a portion of the patient's proximal tibia to which the tibia tray will be attached, a portion of patient's distal femur to which the femoral component will be attached, and/or a portion of the patient's patella to which the patella component will be attached. During such procedures, the surgeon may attempt to balance or otherwise distribute the joint forces of the patient's joint in order to produce joint motion that is similar to the motion of a natural joint. To do so, the surgeon may use surgical experience and manually "feel" for the appropriate joint force balance. Additionally or alternatively, the orthopaedic surgeon may use surgical instruments, such as a ligament balancer in the case of a knee replacement procedure, to assist in the balancing or distributing of joint forces.

In addition, in some surgical procedures such as minimally invasive orthopaedic procedures, surgeons may rely on computer assisted orthopaedic surgery (CAOS) systems to improve the surgeon's ability to see the operative area, to improve alignment of bone cut planes, and to improve the reproducibility of such cut planes. Computer assisted orthopaedic surgery systems assist surgeons in the performance of orthopaedic surgical procedures by, for example, displaying images illustrating surgical steps of the surgical procedure being performed and rendered images of the relevant bones of the patient. Additionally, computer assisted orthopaedic surgery (CAOS) systems provide surgical navigation for the surgeon by tracking and displaying the position of the patient's bones, implants, and/or surgical tools.

SUMMARY

According to one aspect, an orthopaedic surgical system for determining a joint force of a patient's joint may include a sensor module and an adaptor attachable and detachable from the tibial paddle of the sensor module. The sensor module may include a tibial paddle shaped to be positioned between a patient's proximal tibia and distal femur, an elongated handle secured to the tibial paddle, and a sensor array position in the tibial paddle and configured to generate sensor signals indicative of a joint force between the patient's tibia and femur. The tibial paddle may include an inner sidewall defining a centrally-located aperture.

Additionally, the adaptor may include a plurality of lower retainer clips receivable in the centrally-located aperture to attach the adaptor to the tibial paddle. In some embodiments, the adaptor may further include a hub and each of the plurality of lower retainer clips may include a stem extending downwardly from the hub and a lip extending outwardly at a distal end of each stem. Each lip of each lower retainer clip may be configured to engage the inner sidewall of the centrally-located aperture of the tibial paddle to secure the adaptor thereto.

In some embodiments, the tibial paddle may further include a first alignment aperture and a second alignment aperture defined in the tibial paddle. In such embodiments, the adaptor may include a hub from which the plurality of lower retainer clips extend downwardly, a first alignment tab extending downwardly from the hub, and a second alignment tab extending downwardly from the hub. The first alignment tab may be configured to be received in the first alignment aperture and the second alignment tab being configured to be received in the second alignment aperture when the adaptor is coupled to the tibial paddle of the sensor module. In some embodiments, the first alignment aperture may be located toward an anterior side of the tibial paddle, the second alignment aperture may be located toward a posterior side of the tibial paddle, and the centrally-located aperture may be located between the first and second alignment apertures. Additionally, each of the first and second alignment apertures may be defined by a corresponding inner sidewall of the tibial paddle, the corresponding inner sidewalls being curved in a plane defined by the tibial paddle.

Additionally, in some embodiments, each of the first and second alignment tabs may be keyed such that the adaptor is attachable to the tibial paddle in a single orientation. For example, the first alignment tab may be larger than the second alignment tab. In some embodiments, the first alignment tab may have a greater length than the second alignment tab. Additionally, the first alignment aperture may have a larger opening on a surface of the tibial paddle than the second alignment aperture. In some embodiments, the hub of the adaptor may have a circular shape, the first alignment aperture may be located toward an anterior side of the tibial paddle, the second alignment aperture may be located toward a posterior side of the tibial paddle, and the centrally-located aperture may be located between the first and second alignment apertures. Additionally, the adaptor may further include an anti-rotation protrusion extending from the hub along an axis that is parallel to a plane defined by the tibial paddle when the adaptor is coupled to the tibial paddle.

In some embodiments, each of the first and second alignment tabs may include a first and second angled sidewall and each of the first and second alignment apertures comprise a first and second angled sidewall. In such embodiments, the angled sidewalls of the first and second alignment tabs and the first and second alignment apertures may cooperate to provide an amount of lift-off force to detach the adaptor from the tibial plate in response to a reference amount of torque being applied to the adaptor. Additionally, the inner sidewall of the tibial paddle may include an angled section configured to apply inwardly an amount of force to the plurality of lower retainer clips in response to the lift-off force.

The adaptor may include a hub from which the plurality of lower retainer clips extend downwardly and a plurality of upper retainer clips extending upwardly from the hub in some embodiments. In such embodiments, the upper retainer clips may be shaped or sized such that the upper retainer clips are not insertable into the centrally-located aperture of the tibial paddle. Additionally, the adaptor may further include an anti-rotation protrusion extending from the hub along an axis that is parallel to a plane defined by the tibial paddle when the adaptor is coupled to the tibial paddle.

In some embodiments, the orthopaedic surgical system may further include an orthopaedic surgical instrument configured to couple to the adaptor via the upper retainer clips. The orthopaedic surgical system may also include a tibial trialing component that is positionable over the adaptor. The tibial trialing component may include an inner sidewall defining a first aperture and a second aperture in fluid communication with the first aperture. The first aperture may be configured to receive the hub of the adaptor and the second aperture being configured to receive the anti-rotation protrusion when the tibial trialing component is positioned over the adaptor. In some embodiments, the tibial trialing component is positionable over the adaptor in a first orientation that allows the tibial trialing component to rotate relative to the tibial paddle and a second orientation that restricts rotation of the tibial trialing component relative to the tibial paddle. Additionally, in some embodiments, the anti-rotation protrusion is received in the second aperture when the tibial trialing is positioned over the adaptor in the first orientation and the second aperture may be sized to restrict rotation of the tibial trialing component relative to the tibial paddle. Further, in some embodiments, the tibial trialing component may include a third aperture in fluid communication with the first aperture. In such embodiments, the second aperture may be configured to receive the anti-rotation protrusion when the tibial trialing component is positioned over the adaptor in the second orientation and sized to allow rotation of the tibial trialing component relative to the tibial paddle.

According to another aspect, an orthopaedic surgical system for determining a joint force of a patient's joint may include a sensor module, an adaptor attachable and detachable from the tibial paddle of the sensor module, and a tibial trialing component that is configured to be positioned over the adaptor. The sensor module may include a tibial paddle shaped to be positioned between a patient's proximal tibia and distal femur, an elongated handle secured to the tibial paddle, and a sensor array position in the tibial paddle and configured to generate sensor signals indicative of a joint force between the patient's tibia and femur. The tibial paddle may include an inner sidewall defining a centrally-located aperture. Additionally, the adaptor may include a hub, a plurality of lower retainer clips extending downwardly from the hub and receivable in the centrally-located aperture to attach the adaptor to the tibial paddle, and a plurality of upper retainer clips extending upwardly from the hub and sized such that plurality of upper retainer clips are not receivable in the centrally-located aperture. The tibial trialing component that is positionable over the adaptor in a first orientation that limits rotation of the tibial trialing component to rotate relative to the tibial paddle and a second orientation that allows rotation of the tibial trialing component relative to the tibial paddle.

In some embodiments, the adaptor may further include an anti-rotation protrusion extending from the hub along an axis that is parallel to a plane defined by the tibial paddle when the adaptor is coupled to the tibial paddle. Additionally, the tibial trialing component may include an inner sidewall defining a first aperture sized to restrict rotation of the tibial trialing component relative to the tibial paddle. In such embodiments, the anti-rotation protrusion may be received in the first aperture when the tibial component is positioned over the adaptor in the first orientation. Additionally, in some embodiments, the tibial trialing component may include an inner sidewall defining a first aperture sized to allow rotation of the tibial trialing component relative to the tibial paddle. In such embodiments, the anti-rotation protrusion may be received in the first aperture when the tibial component is positioned over the adaptor in the second orientation.

According to a further aspect, an adaptor for coupling a tibial trialing component to a tibial paddle of a sensor module may include a central hub having a top side and a bottom side, a plurality of lower retainer clips sized to be received in an aperture to the tibial paddle, a plurality of upper retainer clips sized such that the upper retainer clips are not receivable within the aperture of the tibial paddle, a first alignment tab extending downwardly from the central hub, and a second alignment tab extending downwardly from the central hub, the second alignment tab having a length greater than the a length of the first alignment tab. Each lower retainer clip may include a stem extending downwardly from the central hub and a lip extending outwardly from a distal end of the corresponding stem. Similarly, each upper retainer clip may include a stem extending upwardly from the central hub and a lip extending outwardly from a distal end of the corresponding stem. Additionally, the second alignment tab may have a length greater than the length of the first alignment tab.

BRIEF DESCRIPTION OF THE DRAWINGS

The detailed description particularly refers to the following figures, in which:

FIG. 7 is a graph of one embodiment of an illumination configuration display protocol for displays of the sensor module of FIG. 2;

FIGS. 16-18 are illustrative screenshots that may be displayed to a user on the display module of FIG. 12;

FIGS. 20A-20E are perspective views of an adaptor of the system of FIG. 19;

DETAILED DESCRIPTION OF THE DRAWINGS

Figure 1:
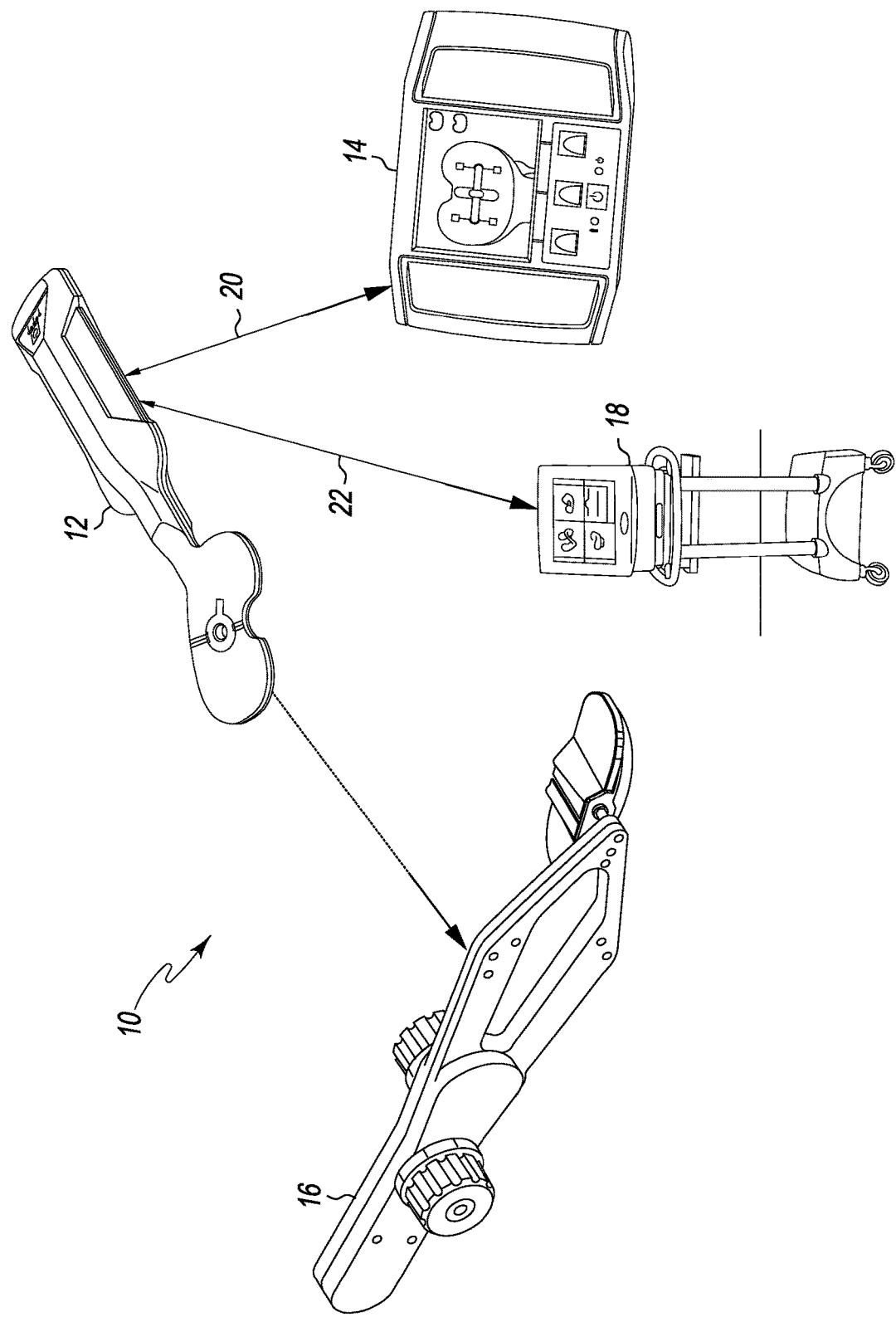
FIG. 1 is a simplified diagram of one embodiment of a system for measuring and displaying joint force data of a patient's joint.
Figure 2:
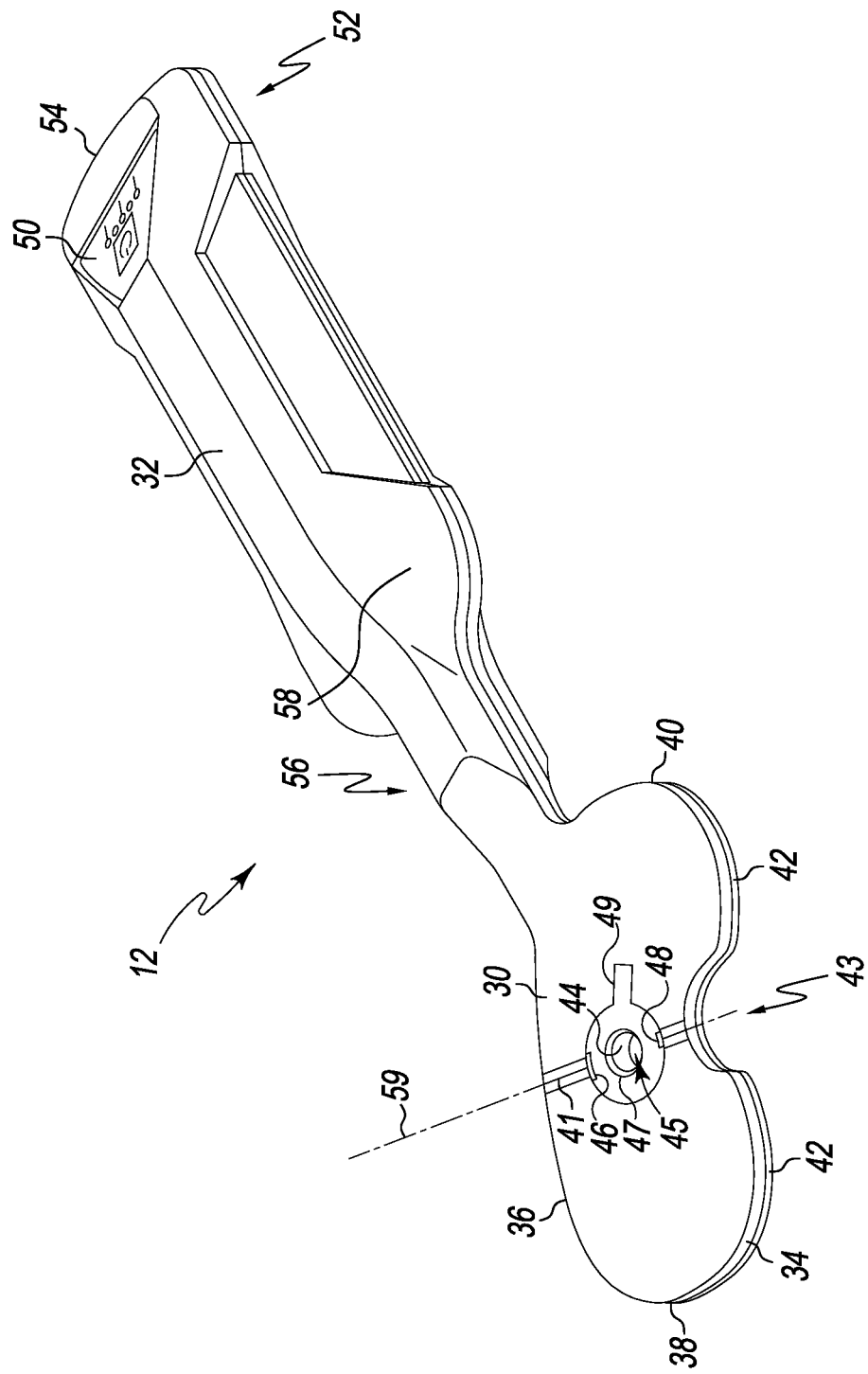
FIG. 2 is a perspective view of one embodiment of a sensor module of the system of FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, in one embodiment, a system 10 for determining and displaying joint forces of a patient's joint during an orthopaedic surgical procedure includes a sensor module 12 and a hand-held display module 14. In some embodiments, the system 10 may also include a joint distractor 16, which is configured to receive the sensor module 12 as discussed below. Additionally, in some embodiments, the system 10 may include a computer assisted surgery system (CAOS) system 18. As discussed in more detail below, the sensor module 12 is configured to be inserted into a patient's knee joint and provide a visual indication of the medial-lateral balance of the knee joint forces to an orthopaedic surgeon. The sensor module 12 may also be configured to transmit joint force data to the handheld display module 14 via a wireless communication link 20 and/or the computer assisted surgery system 18 via a wireless communication link 22. In response, the display module 14 and/or computer assisted surgery system 18 are configured to display the joint force data, or data derived therefrom, to an orthopaedic surgeon. Additionally, during the performance of an orthopaedic surgical procedure, such as a total or partial knee arthroplasty procedure, the sensor module 12 may be coupled to the joint distractor 16 to provide visual indication of the joint forces of the patient's joint during distraction thereof.

Referring now to FIGS. 2-11, the sensor module 12 includes a sensor housing 30 and an elongated handle 32 coupled to the sensor housing 30. The sensor housing 30 is sized and shaped to be positioned in a joint of the patient. In the illustrative embodiment, the sensor housing 30 is embodied as a tibial paddle 34, which is shaped to be positioned in a knee joint of the patient. However, the sensor housing 30 may be configured to be used with other joints of the patient in other embodiments.

Figure 19:
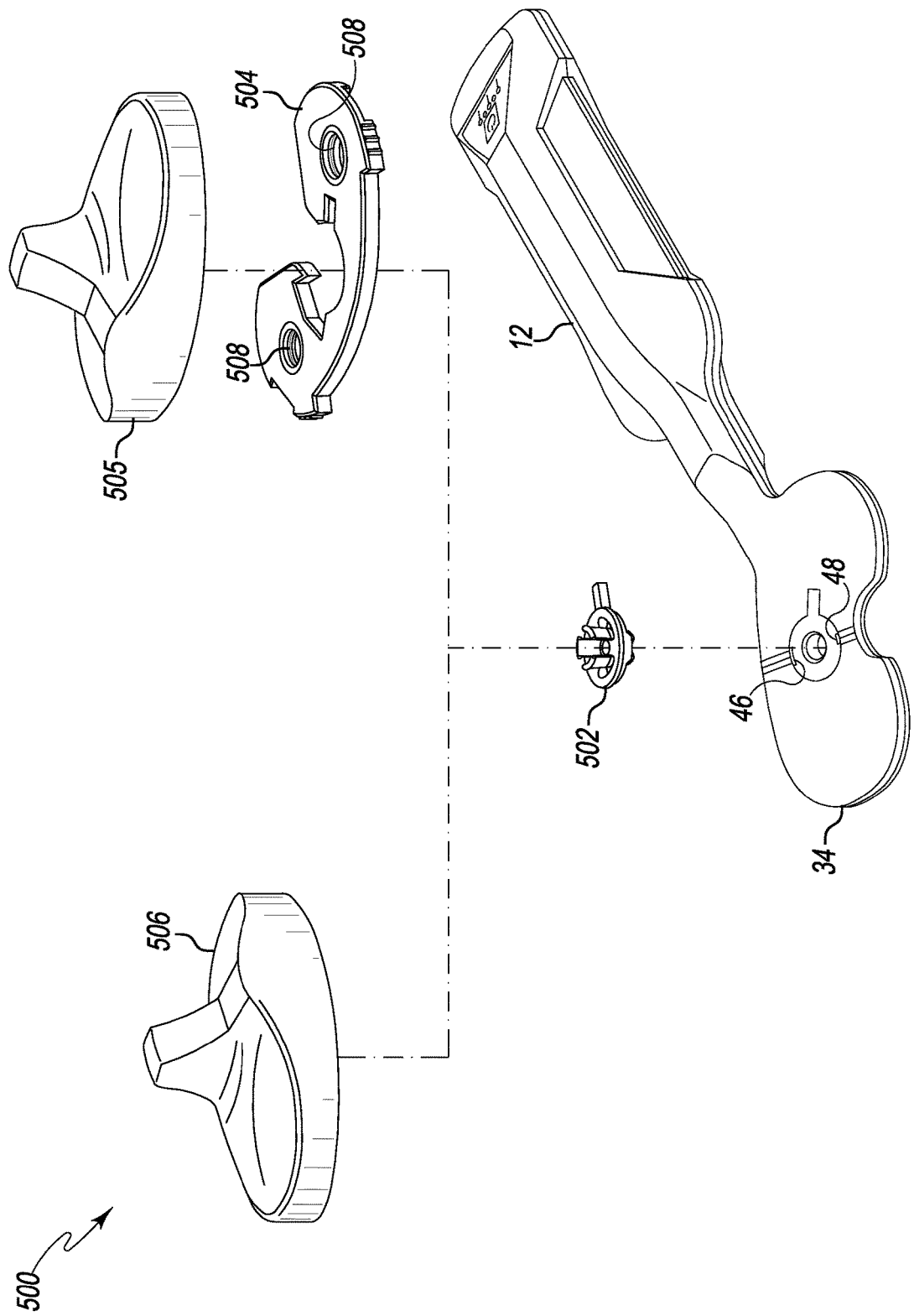
FIG. 19 is a perspective view of one embodiment of a trialing system using the sensor module of FIG. 2.

In use, the tibial paddle 34 is configured to be positioned on a proximal plateau of a patient's resected tibia (see, e.g., FIG. 33-37). As discussed in more detail below, the tibial paddle 34 may be placed in contact with the patient's tibia or may be placed on an intervening platform or other member. Additionally, as discussed in more detail below, the tibial paddle 34 is designed for use with an adaptor 502 (see FIG. 19) and various other orthopaedic surgical instruments, including spacer blocks, balancer/sizer instruments, orthopaedic trials, and/or trial assemblies.

The sensor module 12 may be used on the patient's left or right knee. For example, the sensor module 12 may be used on a patient's left knee via a medial surgical approach wherein the tibial paddle 34 is inserted into the patient's left knee joint via a medial capsular incision. In such position, as discussed below, the handle 32 extends out of the medial capsular incision. Alternatively, by simply flipping or turning over the sensor module 12, the module 12 may be used on the patient's left knee via a lateral surgical approach wherein the tibial paddle 34 is inserted into the patient's left knee joint via a lateral capsular incision. Again, in such position, the handle 32 extends out of the lateral capsular incision.

As such, it should be appreciated that sensor module 12 may be used on the patient's left or right knee using a medial or lateral surgical approach. For clarity of description, the sensor module 12 and the system 10 are described below with reference to an orthopaedic surgical procedure using a medial surgical approach (i.e., using a medial capsular incision to access the patient's joint). However, it should be appreciated that such description is equally applicable to lateral surgical approach procedures. As such, some structures are described using particular anatomical references (e.g., lateral and medial) with the understanding that such references would be flipped or switched when the module 12 is used in a lateral surgical approach procedure. For example, a "medial side" of the tibial paddle 34 becomes a "lateral side" of the tibial paddle 34 when used in a lateral surgical approach procedure.

The tibial paddle 34 is planar or substantially planar and has a shape generally corresponding to the shape of the orthopaedic prosthesis to be implanted in the patient. For example, in the illustrative embodiment, the tibial paddle 34 has a shape generally corresponding to a knee prosthesis of a particular size. However, in other embodiments, the paddle 34 (or sensor housing 30) may have a shape generally corresponding to other types of orthopaedic prostheses such as a hip prosthesis, a shoulder prosthesis, an ankle prosthesis, a spine prosthesis, or a patella prosthesis.

The illustrative tibial paddle 34 includes a curved anterior side 36, a curved lateral side 38, a curved medial side 40, and a curved posterior side 42, each shaped to approximate the shape a tibial bearing of an orthopaedic knee prosthesis. Again, as discussed above, the lateral side 38 and the medial side 40 are lateral and medial sides, respectively, in those embodiments wherein the sensor module 12 is used in a lateral surgical approach procedure. The posterior side 42 includes a posterior notch 43 to allow the tibial paddle 34 to be positioned around the soft tissue of the patient's joint such as the posterior cruciate ligament.

The tibial paddle 34 includes an inner sidewall 44, which defines a vertical aperture or passageway 45 through the tibial paddle 34. The aperture 45 is centrally located on the tibial paddle 34 and, as discussed in more detail below, is shaped and configured to receive an adaptor 502 (see FIG. 19) for attaching various tibial trials and trial assemblies to the sensor module 12. As discussed in more detail below with regard to FIG. 22, the inner sidewall 44 includes an inwardly angled section 47 to facilitate the attachment and removal of the adaptor 502.

The tibial paddle 34 also includes an anterior alignment aperture 46 and a posterior alignment aperture 48. The anterior alignment aperture 46 is located anteriorly (i.e., toward the curved anterior side 36) of the aperture 45, and the posterior alignment aperture 48 is located posteriorly (i.e., toward the posterior notch 43) of the aperture 45. The alignment apertures 46, 48 are inwardly curved in the transverse plane (i.e., a plane defined by the tibial paddle 34) and generally lie along a circle concentric with the aperture 45. Illustratively, the alignment apertures 46, 48 are "keyed" such that the anterior alignment aperture 46 has a greater width (i.e., a medial-to-lateral width) than the posterior alignment aperture 48. As discussed in more detail below, the "keying" of the alignment apertures 46, 48 allow the adaptor 502, or other instruments or devices, to be coupled to the sensor module 12 in a predefined orientation. Of course, it should be appreciated that other features and/or structures may be used in other embodiments to provide a "keyed" coupling to the sensor module 12. For example, in other embodiments, the posterior alignment aperture 48 may have a width greater than the anterior alignment aperture 46, additional or fewer alignment apertures may be used, alignment apertures having different "keyed" shapes may be used, and/or the like.

In some embodiments, the tibial paddle 34 may include an anterior-to-posterior axis indicia 41, such as a printed line, that provides a visual indication of an anterior-to-posterior bisecting axis 59 of the tibial paddle 34. In use, an orthopaedic surgeon or other healthcare provider may use the indicia 41 to help align the tibial paddle 34 within the patient's knee joint. Additionally, in some embodiments, the tibial paddle 34 may include an adaptor indicia 49, such as a printed line, that provides a visual indication of proper positioning of the adaptor 502 when coupled to the tibial paddle 34 of the sensor module 12.

The overall size of the tibial paddle 34 may be selected based on the particular anatomical structure of the patient. For example, in some embodiments, the tibial paddle 34 may be provided in various sizes to accommodate patients of varying sizes. It should be appreciated that the general shape and size of the paddle 34 (and sensor housing 30) is designed and selected such that the paddle 34 or housing 30 does not significantly overhang with respect to the associated bony anatomy of the patient such that the paddle 34 or housing 30 nor adversely impinge the surrounding soft tissue.

The handle 32 includes a pair of displays 50, 52 coupled to a distal end 54 of the handle 32. Another end 56 of the handle 32 opposite the distal end 54 is coupled to the tibial paddle 34. In the illustrative embodiment of FIG. 2, the handle 32 and tibial paddle 34 are substantially monolithic in structure. However, in other embodiments, the tibial paddle 34 may be removably coupled to the handle 32 via a suitable connector or the like.

Figure 4:
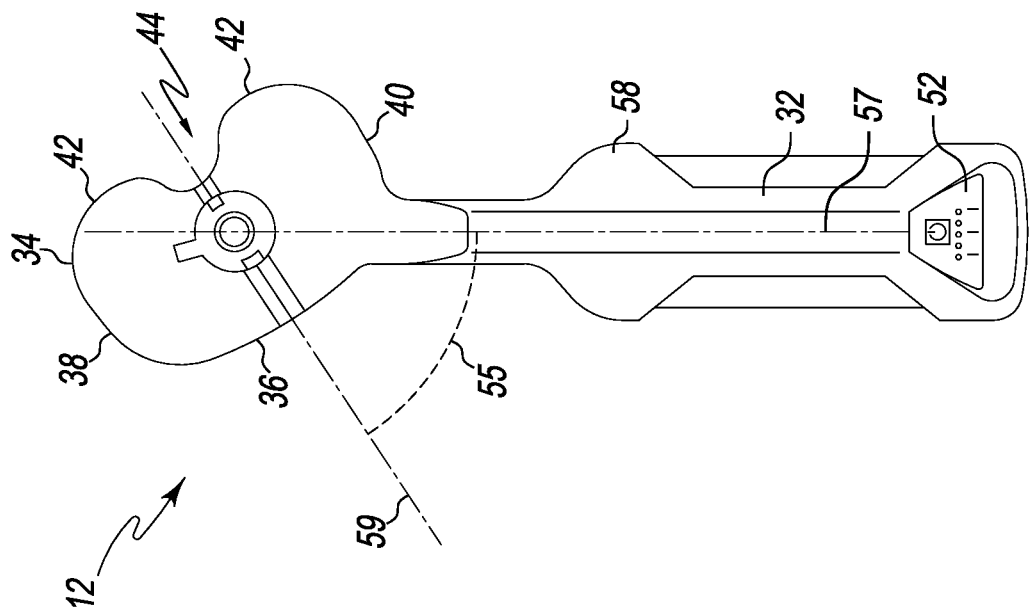
FIG. 4 is a plan view of a bottom side of the sensor module of FIG. 2.
Figure 3:
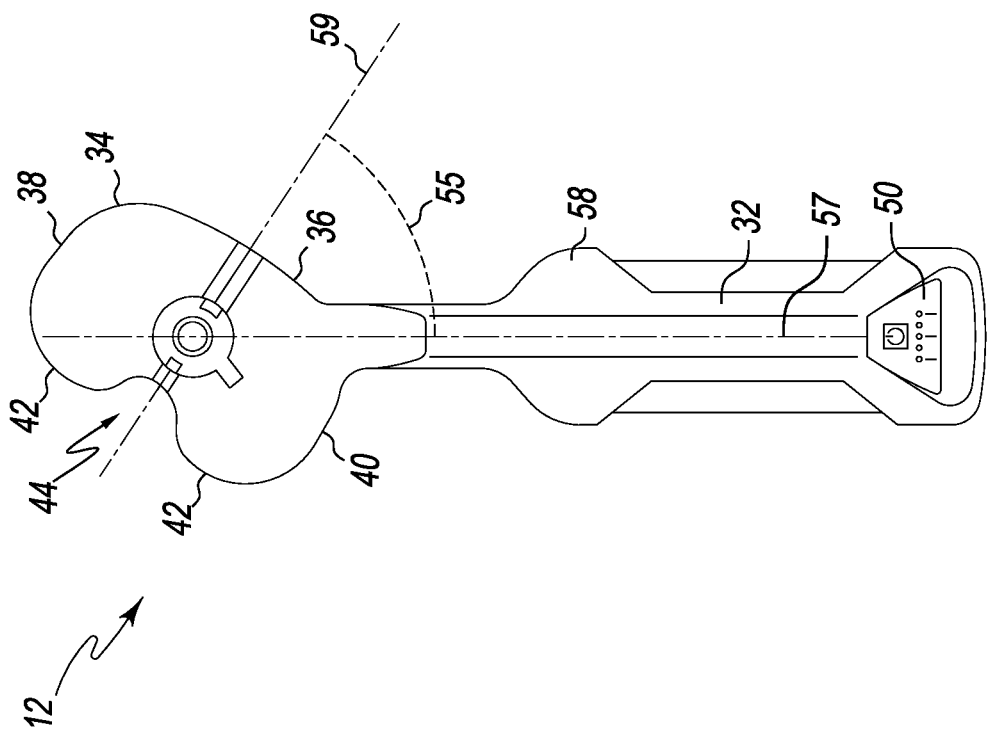
FIG. 3 is a plan view of a top side of the sensor module of FIG. 2.

As illustrated in FIGS. 3 and 4, the elongated handle 32 extends from a side of the tibial paddle 34 and defines a longitudinal axis 57, which is offset from the anterior-to-posterior bisecting axis 59 of the tibial paddle 34 such that an angle 55 greater than 0 degrees is defined between the axes 57, 59. In the illustrative embodiment, the handle 32 extends from the medial side 40 (which is a lateral side when the sensor module 12 is used in a lateral surgical approach procedure). It should be appreciated that because the handle 32 extends from a side of the paddle 34, the tibial paddle 34 may be positioned in a knee joint of a patient without the need to sublux or evert the patient's patella. That is, the tibial paddle 34 may be properly positioned between the patient's proximal tibia and distal femur with the patient's patella in the natural position.

Depending on the particular surgical approach to be used by the orthopaedic surgeon, the surgeon may flip the sensor module 12 to the proper orientation such that the tibial paddle 34 is inserted into the patient's knee joint through the associated capsular incision. In either orientation, the handle 32 extends out of the capsular incision and at least one of the displays 50, 52 is visible to the orthopaedic surgeon. For example, if the orthopaedic surgeon is using a medial surgical approach on a patient's left knee, the orthopaedic surgeon may position the sensor module 12 in the orientation illustrated in FIG. 3 such that the handle 32 extends from the medial side of the patient's knee (through the medial capsular incision) when the tibial paddle 34 is inserted into the knee joint and the display 50 is visible to the surgeon. Alternatively, if the orthopaedic surgeon is using a lateral surgical approach on a patient's left knee, the orthopaedic surgeon may position the sensor module 12 in the orientation illustrated in FIG. 4 such that the handle 32 extends from the lateral side of the patient's knee (through the lateral capsular incision) when the tibial paddle 34 is inserted into the knee joint and the display 52 is visible to the surgeon.

As discussed above, the sensor module 12 is configured to assist a surgeon during the performance of an orthopaedic surgical procedure. As such, the sensor module 12 includes an outer housing 58 formed from a bio-compatible material. For example, the outer housing 58 may be formed from a bio-compatible plastic or polymer. In one particular embodiment, the sensor module 12 is configured for single-usage and, as such, is provided in a sterile form. For example, the sensor module 12 may be provided in a sterile packaging. However, in those embodiments wherein the tibial paddle 34 is removably coupled to the handle 32, the tibial paddle 34 may be designed for single-usage and the handle 32 may be configured to be reusable via an autoclaving procedure or the like.

Figure 5:
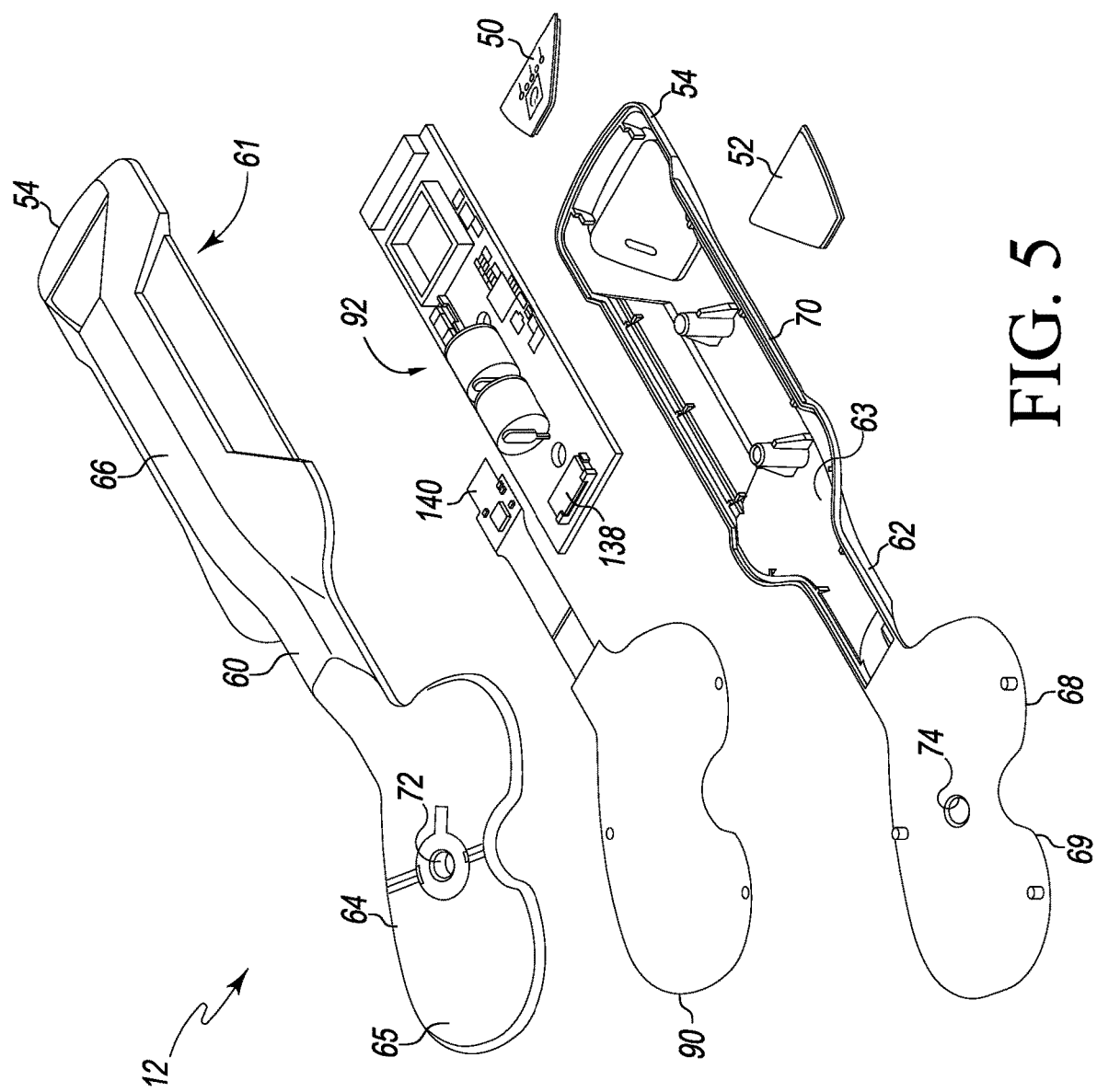
FIG. 5 is an exploded, perspective view of the sensor module of FIG. 2.

As illustrated in FIG. 5, the outer housing 58 of the sensor module 12 includes an upper housing 60 and a lower housing 62, which are coupled to each other. In some embodiments, the upper housing 60 and the lower housing 62 are mirror images of each other. The upper housing 60 includes an interior surface 61 that confronts, or otherwise, faces an interior surface 63 of the lower housing 62 when the housings 60, 62 are coupled to each other. Additionally, the upper housing 60 includes an upper tibial paddle housing 64 and an upper handle housing 66. Similarly, the lower housing 62 includes a lower tibial paddle housing 68 and a lower handle housing 70. The upper tibial paddle housing 64 has a planer or substantially planar outer surface 65 and includes an inner sidewall 72 that defines, in part, the vertical aperture 45 extending through the tibial paddle 34. Similarly, the lower tibial paddle housing 68 has a planer or substantially planar outer surface 69 and includes an inner sidewall 74 that defines, in part, the vertical aperture 45.

Figure 6:
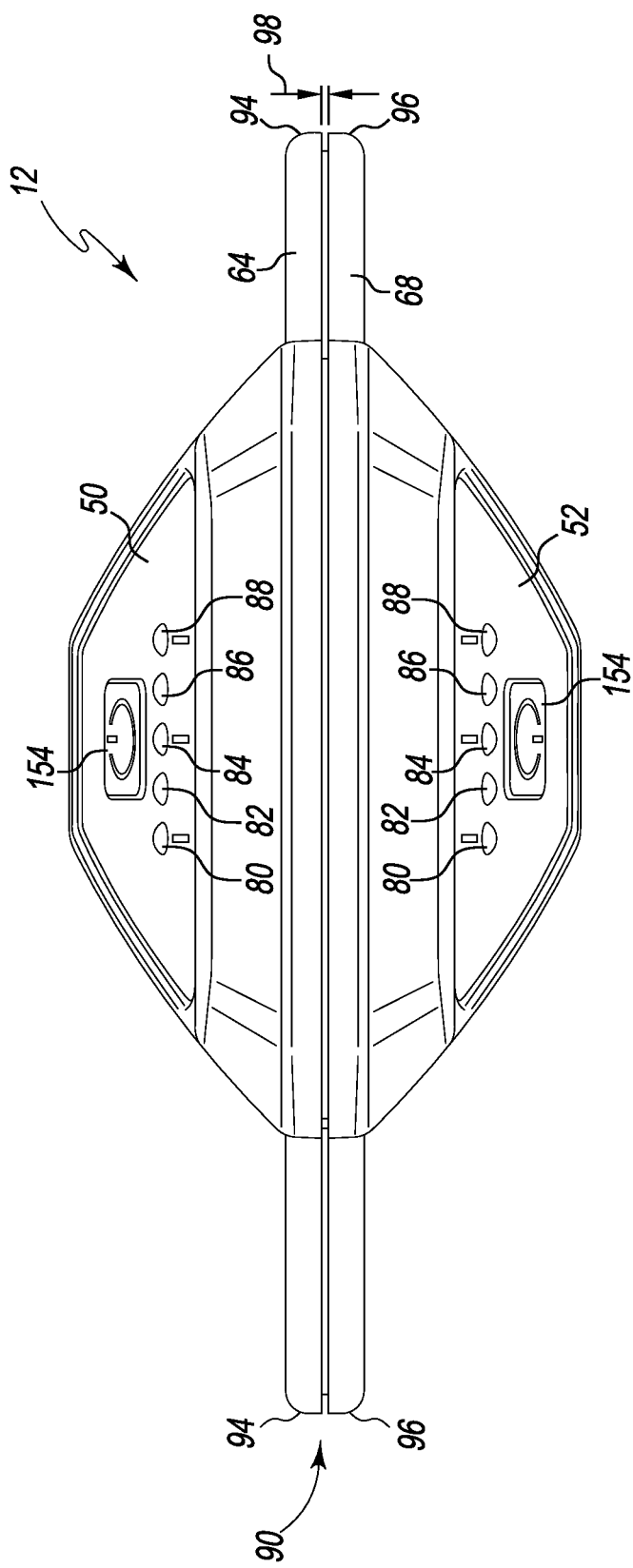
FIG. 6 is an elevation view of a handle end of the sensor module of FIG. 2.

The display 50 is coupled to the distal end 54 of the upper housing 60 and the display 52 is coupled to the distal end 54 of the lower housing 62. As illustrated in FIG. 6, each of the displays 50, 52 is illustratively embodied as a row or an array of light emitting diodes. However, in other embodiments, the displays 50, 52 may be embodied as other types of displays such as liquid crystal displays, segmented displays, and/or the like. In the illustrative embodiment of FIG. 6, each of the displays 50, 52 includes five separate light emitting diodes 80, 82, 84, 86, 88. As discussed in more detail below, the central light emitting diodes 84 are illuminated when the medial-lateral joint forces of the patient's knee joint are approximately equal. Additionally, the light emitting diodes 80 and/or 82 are illuminated when the medial joint force is greater than the lateral joint force of the patient's knee joint by a predetermined threshold amount and the light emitting diodes 86 and 88 are illuminated when the lateral joint force is greater than the medial joint force of the patient's knee by the predetermine threshold amount (again, assuming a medial surgical approach). As shown in FIG. 6, the light emitting diodes 80, 82, 84, 86, 88 of the displays 50, 52 are arranged such that the light emitting diodes 80, 82 correspond with the medial side 40 of the tibial paddle 34 and the light emitting diodes 86, 88 correspond with the lateral side 38 of the tibial paddle 34 regardless of the orientation (i.e., regardless of whether the upper housing 60 or the lower housing 62 is facing upwardly).

As discussed in more detail below, the light emitting diodes 80, 82, 84, 86, 88 may be illuminated in one of a plurality of illumination configurations according to a predetermined display protocol to provide a visual indication to the surgeon of the relative medial-lateral joint force balance. By activating or illuminating one or more of the light emitting diodes 80, 82, 84, 86, 88, an orthopaedic surgeon may visual determine which side of the patient's joint is exerting a greater amount of force and the general magnitude of such force relative to the opposite side of the patient's knee joint. For example, one illustrative display protocol is presented in graph 170 in FIG. 7, which includes nine separate illumination configurations. According to the illustrative display protocol 170, only the light emitting diode 80 is illuminated if the medial force component is between 85%-100% and the lateral force component is between 0%-15%. However, both light emitting diodes 80 and 82 are illuminated if the medial force component is between 75%-84% and the lateral force component is between 16%-25%. If the medial force component is between 65%-74% and the lateral force component is between 26%-35%, only the light emitting diode 82 is illuminated. If the medial force component is between 55%-64% and the lateral force component is between 36%-45%, both light emitting diodes 82 and 84 are illuminated. If the medial force component is between 46%-54% and the lateral force component is between 46%-54%, only the light emitting diode 84 is illuminated, which indicates a relative equal balance of medial and lateral forces. If the medial force component is between 36%-45% and the lateral force component is between 55%-64%, both light emitting diodes 84 and 86 are illuminated. If the medial force component is between 26%-35% and the lateral force component is between 65%-74%, only the light emitting diode 86 is illuminated. If the medial force component is between 26%-35% and the lateral force component is between 75%-84%, both light emitting diodes 86 and 88 are illuminated. And, if the medial force component is between 0%-15% and the lateral force component is between 85%-100%, only the light emitting diode 88 is illuminated. In this way, a visual indication of the relative medial-lateral joint balance of the joint force of the patient's knee is provided to the orthopaedic surgeon. Of course, in other embodiments, other display protocols may be used to control and illuminate the displays 50, 52.

The sensor module 12 includes a sensor array 90 positioned in the tibial paddle 34 and communicatively coupled to a control circuit 92 positioned in the handle 32. The sensor array 90 is "sandwiched" between the upper housing piece 60 and the lower housing piece 62 and includes a centrally-located aperture 91 through which the vertical aperture or passageway 45 extends when the upper housing 60 and a lower housing 62 of the outer housing 58 of the sensor module 12 are coupled together. The anterior alignment aperture 46 and the posterior alignment aperture 48 also extend through the aperture 91 when the upper housing 60 and a lower housing 62 of the outer housing 58 of the sensor module 12 are coupled together. The upper housing piece 60 and the lower housing piece 62 are spaced apart to allow the sensor array 90 to be compressed by the joint force applied to the tibial paddle 34. For example, as illustrated in FIG. 6, the upper housing 64 includes an outer rim 94 and the lower housing 66 includes an outer rim 96, which is spaced apart from the outer rim 94 of the upper housing 64 by a distance 98. When a joint force is applied to the tibial paddle 34, the outer rims 94, 96 are moved toward each as the sensor array 90 is compressed.

Figure 8:
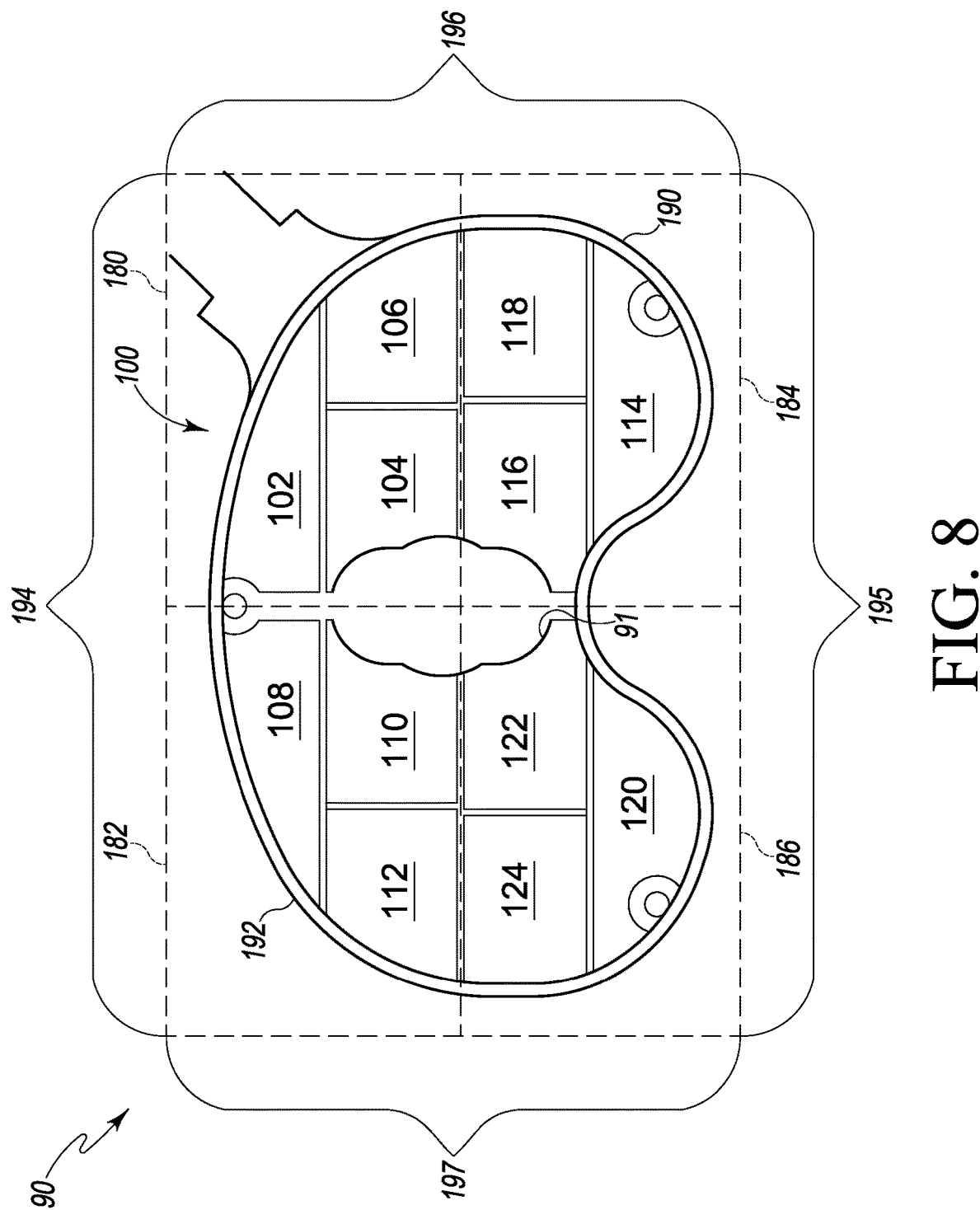
FIG. 8 is a simplified diagram of one embodiment of a sensor array of the sensor module of FIG. 2.

The sensor array 90 includes a plurality of pressure sensors or sensor elements 100 configured to generate sensor signals indicative of the joint force applied to the sensor array 90. In the illustrative embodiment, the pressure sensors 100 are embodied as capacitive pressure sensors, but may be embodied as other types of sensors in other embodiments. The pressure sensors 100 of the sensor array 90 may be arranged in a particular configuration. For example, in one embodiment as illustrated in FIG. 8, the sensor array 90 includes a set of medial-anterior sensors 180 configured to measure a medial-anterior component of the joint force, a set of lateral-anterior sensors 182 configured to measure a lateral-anterior component of the joint force, a set of medial-posterior sensors 184 configured to measure a medial-posterior component of the joint force, and a set of lateral-posterior sensors 186 to measure a lateral-posterior component of the joint force. Illustratively, the set of medial-anterior sensors 180 includes an anterior-most sensor 102, a sensor 104 located posteriorly from the anterior-most sensor 102 and toward the center of the sensor array 90, and a sensor 106 located posteriorly from the anterior-most sensor 102 and located toward a medial side 190 of the sensor array 90. The set of lateral-anterior sensors 182 includes an anterior-most sensor 108, a sensor 110 located posteriorly from the anterior-most sensor 108 and toward the center of the sensor array 90, and a sensor 112 located posteriorly from the anterior-most sensor 108 and located toward a lateral side 192 of the sensor array 90. The set of medial-posterior sensors 184 includes a posterior-most sensor 114, a sensor 116 located anteriorly from the posterior-most sensor 114 and toward the center of the sensor array 90, and a sensor 118 located anteriorly from the posterior-most sensor 114 and located toward the medial side 190 of the sensor array 90. The set of lateral-posterior sensors 186 includes a posterior-most sensor 120, a sensor 122 located anteriorly from the posterior-most sensor 120 and toward the center of the sensor array 90, and a sensor 124 located anteriorly from the posterior-most sensor 120 and located toward the lateral side 192 of the sensor array 90.

The sets of medial-anterior sensors 180 and lateral-anterior sensors 182 form a set of anterior sensors 194, and the sets of medial-posterior sensors 184 and lateral-posterior sensors 186 form a set of posterior sensors 195. Similarly, the sets of medial-anterior sensors 180 and medial-posterior sensors 184 form a set of medial sensors 196, and the sets of lateral-anterior sensors 182 and lateral-posterior sensors 186 form a set of lateral sensors 197. In the illustrative embodiment of FIG. 8, each of the medial-anterior sensors 180 has a surface area equal, or substantially equal, to the surface area of each of the lateral-anterior sensors 182. Similarly, each of the medial-posterior sensors 184 has a surface area equal, or substantially equal, to the surface area of the lateral-posterior sensors 186. Additionally, in some embodiments, each of the anterior sensors 194 has a surface area less than each of the posterior sensors 195. For example, in one particular embodiment, each of the anterior sensors 194 has a surface area equal to about 0.174 in$^2$, and each of the posterior sensors 195 has a surface area equal to about 0.187 in$^2$. Additionally, in another particular embodiment, each of the anterior sensors 194 has a surface area equal to about 0.243 in$^2$, and each of the posterior sensors 195 has a surface area equal to about 0.263 in$^2$. Of course, in other embodiments, the sensor array 90 may include additional or fewer sensors or sensing elements having similar or dissimilar sizes, locations, and/or orientations.

Figure 9:
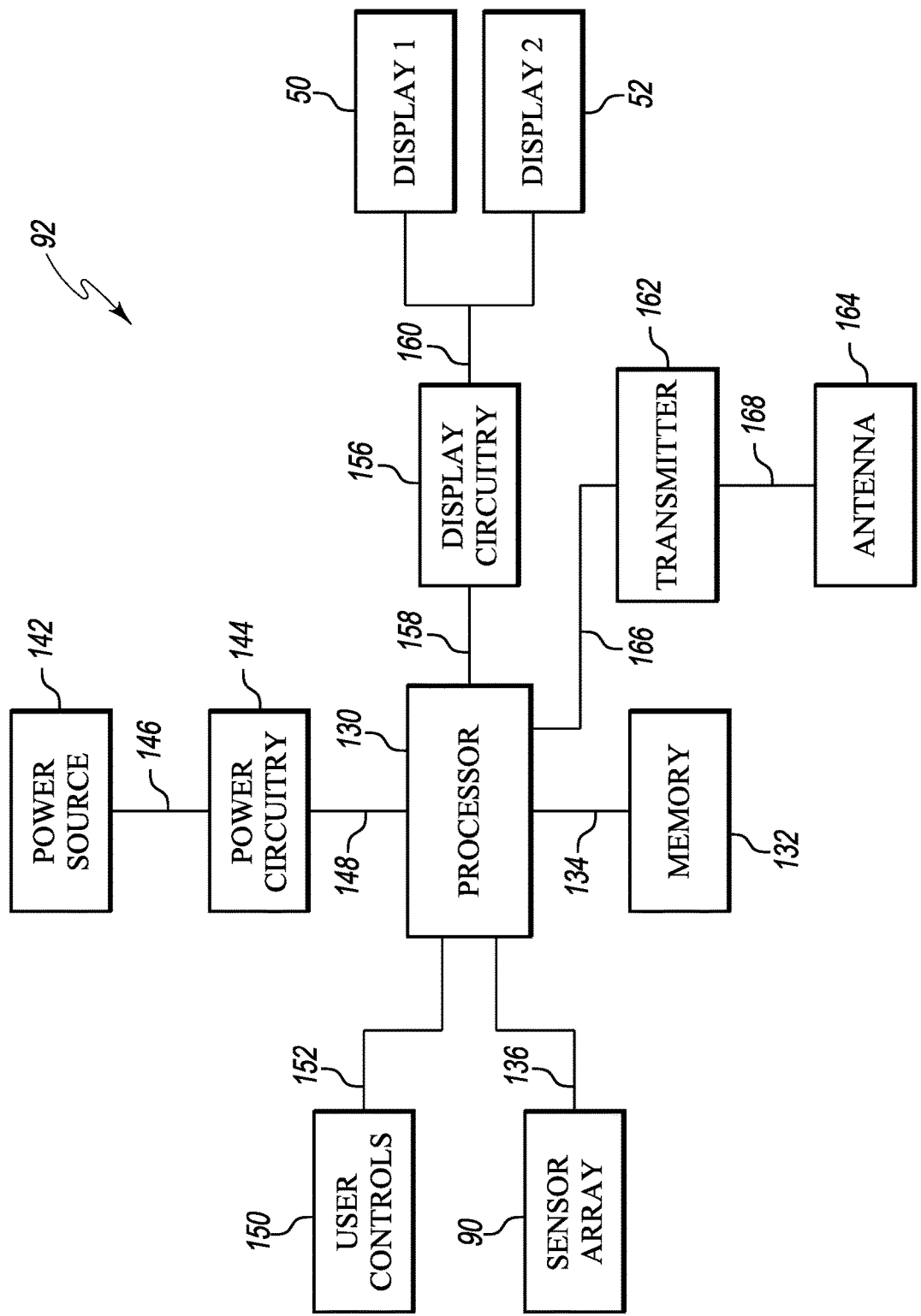
FIG. 9 is a simplified block diagram of one embodiment of an electrical circuit of the sensor module of FIG. 2.
Figure 10:
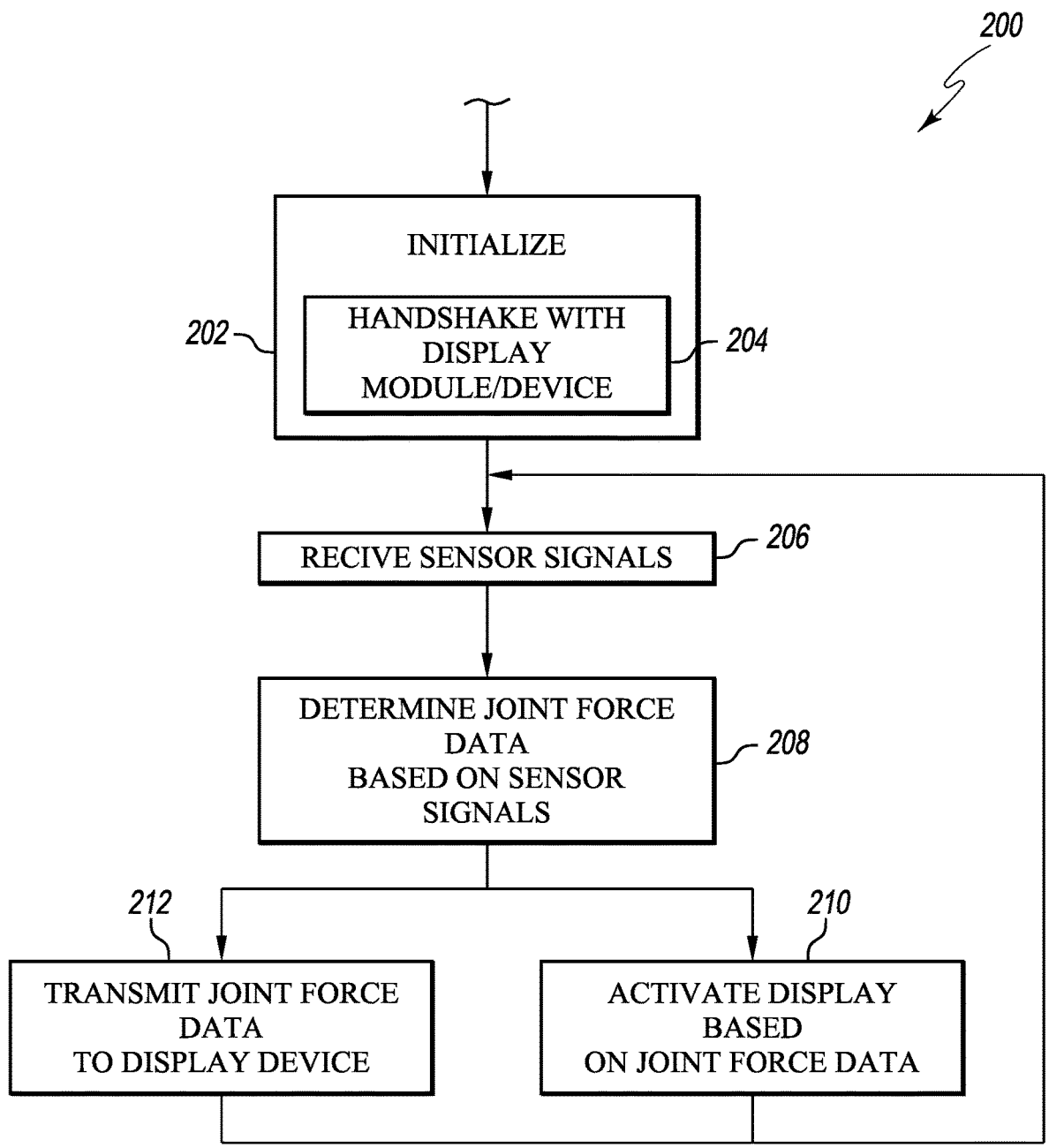
FIG. 10 is a simplified flow diagram of one embodiment of a method for determining and displaying joint force data that may be executed by the sensor module of FIG. 2.

Referring now to FIG. 9, the control circuit 92 includes a processor 130 and a memory device 132. The processor 130 may be embodied as any type of processor configured to perform the functions described herein. For example, the processor 130 may be embodied as a separate integrated circuit or as a collection of electronic devices. Additionally, the processor may be a single or multi-core processor. Although only a single processor 130 is illustrated in FIG. 10, it should be appreciated that in other embodiments, the control circuit 92 may include any number of additional processors. The memory device 132 may be embodied as one or more read-only memory devices and/or random access memory devices. For example, the memory device 132 may be embodied as or otherwise include electrically erasable programmable read-only memory devices (EEPROM), dynamic random access memory devices (DRAM), synchronous dynamic random access memory devices (SDRAM), double-data rate dynamic random access memory devices (DDR SDRAM), and/or other volatile or non-volatile memory devices. Additionally, although only a single memory device is illustrated in FIG. 9, in other embodiments, the control circuit 92 may include additional memory devices.

The processor 130 is communicatively coupled to the memory device 132 via signal paths 134. The signal paths 134 may be embodied as any type of signal paths capable of facilitating communication between the processor 130 and the memory device 132. For example, the signal paths 134 may be embodied as any number of wires, printed circuit board traces, via, bus, intervening devices, and/or the like. The processor 130 is also communicatively coupled to the sensor array 90 via signal paths 136. Similar to signal paths 134, the signal paths 136 may be embodied as any type of signal paths capable of facilitating communication between the processor 130 and the sensor array 90 including, for example any number of wires, printed circuit board traces, via, bus, intervening devices, and/or the like. Additionally, the signal path 136 may include a connector 138 (see FIG. 5) configured to receive a plug-end 140 of the sensor array 90.

The control circuit 92 also includes a power source 142 and associated power control circuitry 144. The power source 142 may be embodied as a number of batteries sized to fit in the sensor module 12. The power source 142 is electrically coupled to the power control circuitry 144 via signal paths 146 and the power control circuitry 144 is electrically coupled to the processor 130 and other devices of the control circuit 92 via signal paths 148. The signal paths 146, 148 may be embodied as any type of signal paths including, for example any number of wires, printed circuit board traces, via, bus, intervening devices, and/or the like. The power circuitry 144 may include power control, distribution, and filtering circuitry and is configured to provide or distribute power from the power source 142 to the processor 130 and other devices or components of the control circuit 92. As discussed in more detail below, the power circuitry 144 may be configured to continuously supply power to the processor 130 and other components of the control circuit 92 after being turned "on" and until the power source 142 is depleted. That is, a user is unable to turn "off" the sensor module 12 after initially turning the module 12 "on" in some embodiments. Such functionality ensures, for example, that the sensor module 12 is not reused in subsequent surgeries.

The control circuit 92 also includes user controls 150 communicatively coupled to the processor 130 via signal paths 152. The user controls 150 are embodied as power buttons 154 (see FIG. 6) located on the displays 50, 52 and selectable by a user to turn the sensor module 12 on. However, in the illustrative embodiment, the control circuit 92 is configured to prevent or otherwise limit the ability of the user from turning off the sensor module 12 via the power buttons 154 or other controls after the sensor module 12 has been turned on. That is, once turned on, the control circuit 92 is configured to remain on until the power source 142 is depleted. Such a configuration ensures that the sensor module 12 is used during a single orthopaedic surgical procedure and is not otherwise reusable in multiple procedures.

The signal paths 152 are similar to the signal paths 134 and may be embodied as any type of signal paths capable of facilitating communication between the user controls 150 and the processor 130 including, for example any number of wires, printed circuit board traces, via, bus, intervening devices, and/or the like.

The control circuit 92 also includes display circuitry 156 for driving and/or controlling the displays 50, 52. The display circuitry 156 is communicatively coupled to the processor 130 via signal paths 158 and to the displays 50, 52 via signal paths 160. Similar to the signal paths 134 discussed above, the signal paths 158, 160 may be embodied as any type of signal paths capable of facilitating communication between the processor 130 and display circuitry 156 and the display circuit 156 and displays 50, 52, respectively. For example, the signal paths 158, 160 may be embodied as any number of wires, printed circuit board traces, via, bus, intervening devices, and/or the like. As discussed above, in the illustrative embodiment, the displays 50, 52 are embodied as an arrangement of light emitting diodes 80, 82, 84, 86, 88.

In some embodiments, the sensor module 12 is configured to transmit force data to the display module 14 and/or computer assisted orthopaedic surgery (CAOS) system 18. In such embodiments, the control circuit 92 includes transmitter circuitry 162 and an antenna 164. The transmitter circuitry 162 is communicatively coupled to the processor 130 via signal paths 166 and to the antenna 164 via signal paths 168. The signal paths 166, 168 may be embodied as any type of signal paths capable of facilitating communication between the transmitter circuitry 162 and the processor 130 and antenna 164, respectively. For example, similar to the signal paths 134, the signal paths 166, 168 may be embodied as any number of wires, printed circuit board traces, via, bus, intervening devices, and/or the like. The transmitter circuitry 162 may be configured to use any type of wireless communication protocol, standard, or technologies to transmit the joint force data to the display module 14 and/or computer assisted orthopaedic surgery (CAOS) system 18. For example, the transmitter circuitry 162 may be configured to use a wireless networking protocol, a cellular communication protocol such as a code division multiple access (CDMA) protocol, a Bluetooth® protocol, or other wireless communication protocol, standard, or technology.

Figure 11:
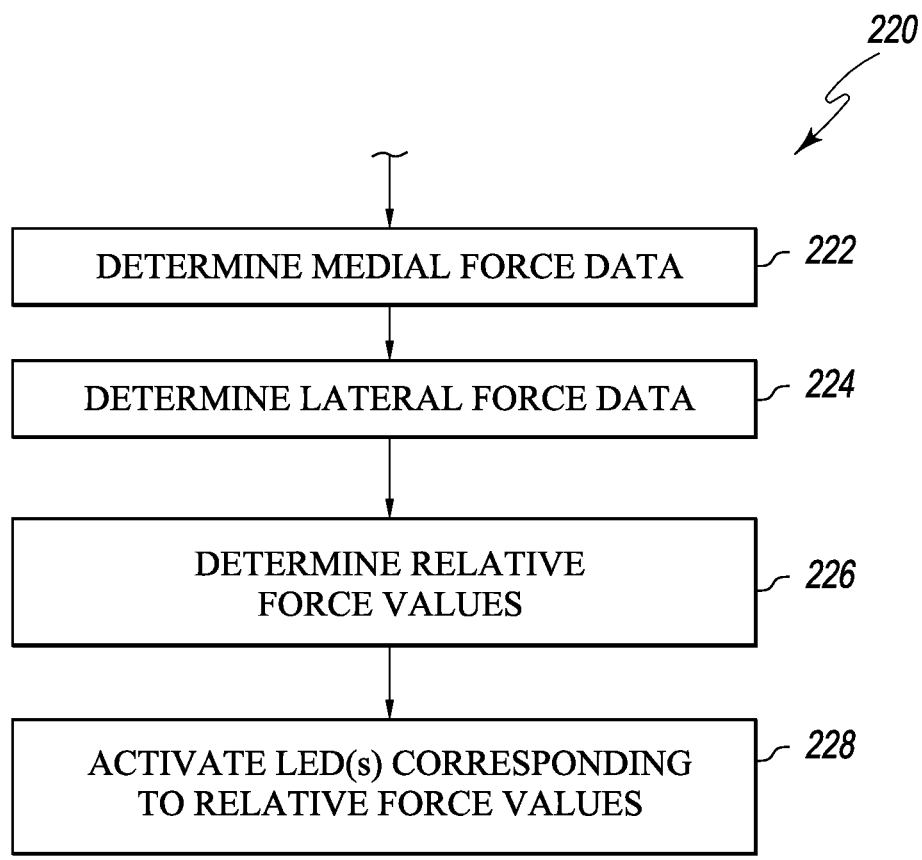
FIG. 11 is a simplified flow diagram of one embodiment of a method for displaying relative joint force data that may be executed by the sensor module of FIG. 2.

Referring now to FIGS. 10 and 11, in use, the control circuit 92 is configured to execute a method 200 for determining joint force data of a patient's joint and providing a visual indication of the medial-lateral balance of the joint force of the patient's knee joint. The method 200 begins with block 202 in which the control circuit 92 is initialized. For example, in block 202, the control circuit 92 may perform any number of system checks, clear any registers of the processor 130, and/or perform other initialization and/or integrity checks. Additionally, in some embodiments, the control circuit 92 is configured to perform a handshaking routine in block 204 with the hand-held display device 14 and/or the computer assisted orthopaedic surgery (CAOS) system 18. During the handshaking routine, the control circuit 92 and the hand-held display device 14 and/or the computer assisted orthopaedic surgery (CAOS) system 18 may be configured to determine communication protocols and/or otherwise establish any type of communication procedures for transmitting the joint force data from the sensor module 12 to the device 14 or system 18.

In block 206, the control circuit 92 receives the sensor signals or data from the sensor array 90. As discussed above, the sensor array 90 generates sensor signals indicative of a joint force applied to the tibial paddle 34 when the paddle 34 is positioned in the knee joint of a patient. In block 208, the processor 130 of the control circuit 92 determines joint force data based on the sensor signals received from the sensor array 90. The joint force data is indicative of the joint force of the patient's knee joint. In some embodiments, the joint force data may be embodied as specific joint force values such as a medial joint force component value, a lateral joint force component value, an anterior joint force component value, and/or a posterior joint force component value, each force being determined in Newtons or similar force measurement unit. In such embodiments, the medial joint force component may be determined based on the sensor signals from the set of medial sensors 196, and the lateral joint force component may be determined based on the sensor signals from the set of lateral sensors 197. Additionally, the anterior joint force component may be based on the set of anterior sensors 194, and the posterior joint force component may be based on the sensor signals from the set of posterior sensors 195. Subsequently, in block 210 the control circuit 92 controls or otherwise activates the displays 50, 52 to display the joint force data determined in block 208. For example, in embodiments wherein one or more specific joint forces are determined, the processor 130 may display the determine joint forces or indicia thereof on the displays 50, 52.

Additionally or alternatively, the control circuit 92 may be configured to determine the medial-lateral balance of the joint force and display indicia of such medial-lateral balance on the displays 50, 52 in blocks 208, 210. For example, as illustrated in FIG. 11, the control circuit 92 may execute a method 220 for determining the medial-lateral balance of the joint force of the patient's knee joint. In block 222, the control circuit 92 determines medial joint force data based on the sensor signals received from the set of medial sensors 196. Similarly, in block 224, the control circuit 92 determines lateral joint force data based on the sensor signals received from set of lateral sensors 197. The medial and lateral joint force data may be embodied as the specific joint force determined in Newtons or may be embodied as some representation thereof. For example, in some embodiments, the medial and lateral joint force data is measured in capacitance. Additionally, it should be appreciated that the blocks 222 and 224 may be executed in either order.

In block 226, the control circuit 92 determines the relative medial-lateral balance of the joint force of the patient's joint. To do so, the control circuit 92 compares the medial force data and the lateral force data. For example, in one embodiment, the control circuit 92 is configured to determine a total force value by summing the medial force data and the lateral force data. The control circuit 92 subsequently determines a medial percentage value by dividing the medial force data by the total force value and a lateral percentage value by dividing the lateral force data by the total force value. As such, if the medial and lateral forces of a patient's joint are balanced, the medial percentage value would be determined to be about 50% and the lateral percentage value would be determined to be about 50%. Of course, in some embodiments, the control circuit 92 may be configured to determine only one of the medial and lateral percentage values, the remaining one being known or determined by simple subtraction from 100%.

In block 228, the control circuit 92 activates or controls the displays 50, 52 to provide a visual indication of the relative medial-lateral balance of the joint forces of the patient's joint. For example, in embodiments wherein the displays 50, 52 are embodied as light emitting diodes, the control circuit 92 is configured to activate or illuminate one or more of the light emitting diodes to provide a visual indication of the medial-lateral balance of joint forces. The control circuit 92 may use any display protocol or illumination configuration of the light emitting diodes that provides an appropriate indication to the orthopaedic surgeon of such joint forces. For example, in one particular embodiment, the control circuit 92 is configured to control the displays 50, 52 according to the display protocol 170 illustrated in and discussed above in regard to FIG. 7.

In this way, sensor module 12 provides a visual indication to the orthopaedic surgeon of the relative medial and lateral forces of the patient's joint. As discussed in more detail below, the orthopaedic surgeon can perform balancing procedures on the patient's knee joint while monitoring the current balance of the medial and lateral forces via the displays 50, 52 to achieve the desired balance for the particular patient. Additionally, because the sensor module 12 includes a display 50, 52 on either side, the orthopaedic surgeon is provide the visual indication of the joint forces whether the surgeon is operating on the patient's left or right knee.

Figure 12:
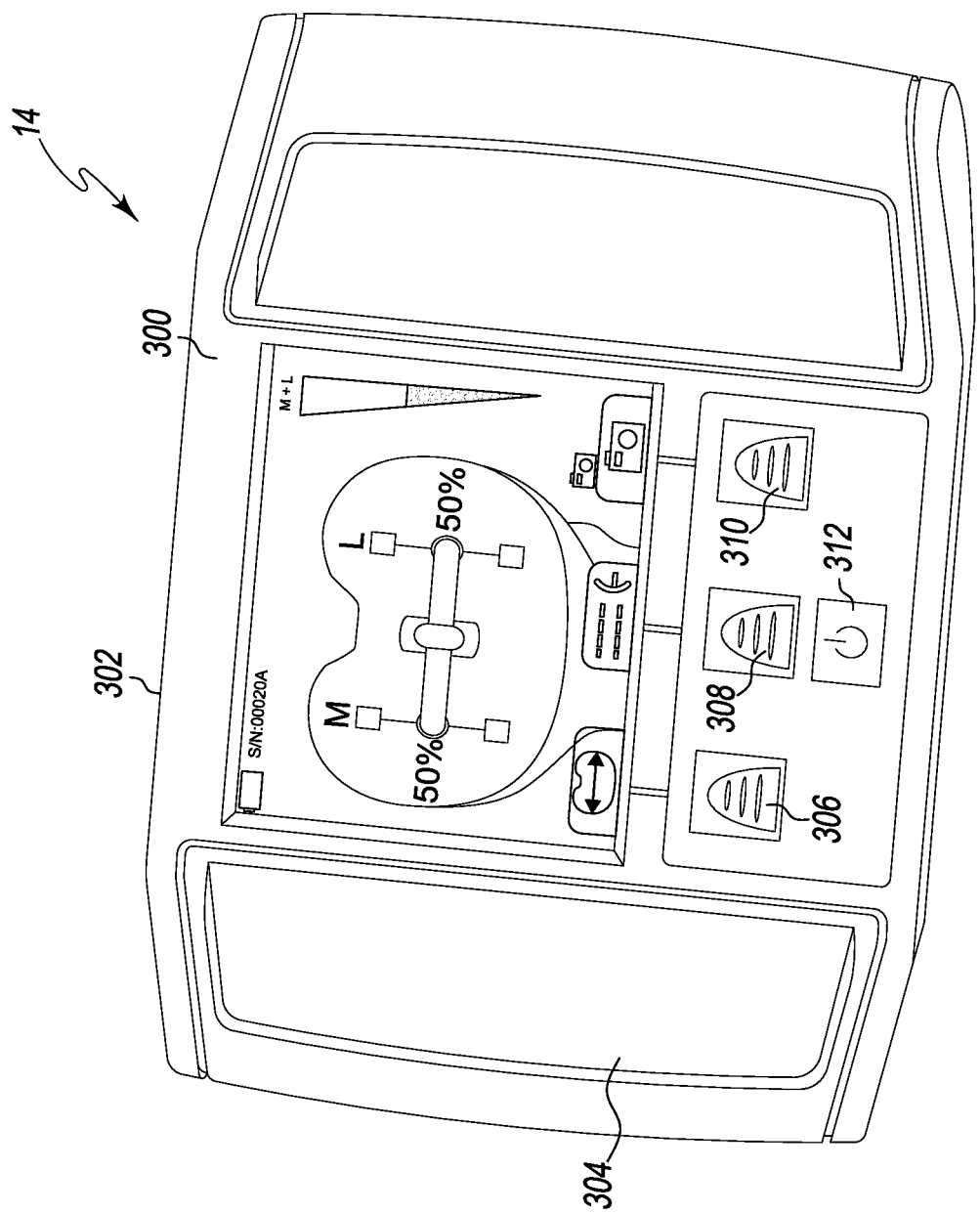
FIG. 12 is a perspective view of one embodiment of a display module of the system of FIG. 1.
Figure 13:
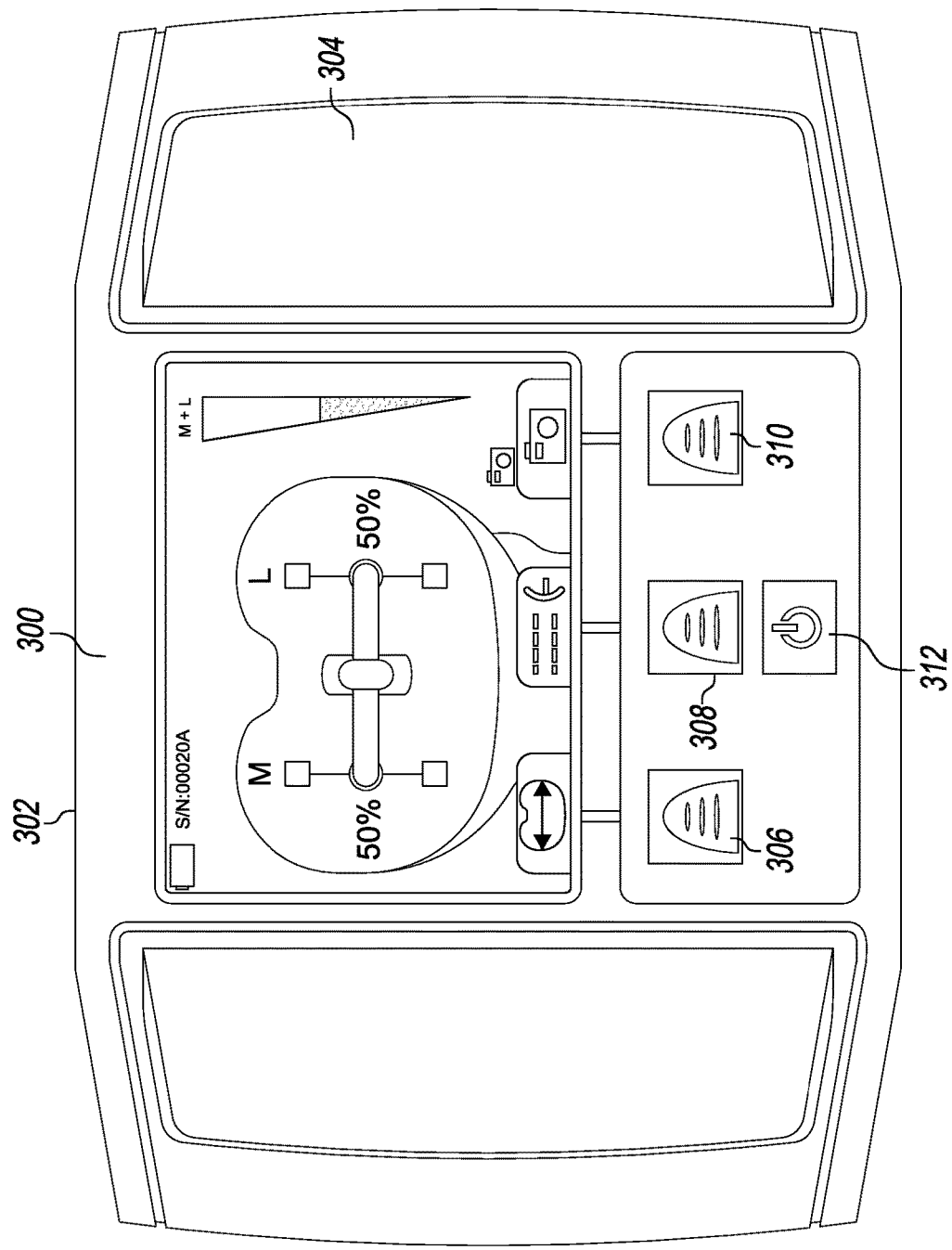
FIG. 13 is a plan view of the display module of FIG. 12.

Referring back to FIG. 12, in addition to activating the displays 50, 52 to provide the visual notification of the joint forces in block 210, the sensor module 12 may be configured to transmit the joint force data in block 212. As discussed above, the sensor module 12 may transmit the joint force data to the hand-held display 14 and/or computer assisted orthopaedic surgery (CAOS) system 18 in block 212. The transmitted joint force data may be embodied as the specific joint forces measured in Newtons, for example, or may be representations thereof. For example, the sensor signals received from the sensor array 90 or electrical representations of the levels of such signals may be transmitted in block 212. Alternatively, the sensor module 12 may transmit joint force data indicative of the determined medial-lateral balance of the joint force of the patient's joint.

Referring now to FIGS. 12-18, the hand-held display module 14 includes a housing 300 sized to be held in the hands of an orthopaedic surgeon and used during the performance of an orthopaedic surgical procedure. In this way, the display module 14 is configured to be mobile. The display module 14 also includes a display 302 coupled to an upper side 304 of the housing 300. A plurality of user input buttons 306, 308, 310 are also positioned on the upper side 304 of the housing 300 below the display 302. The display module 14 also includes a power button 312. In the illustrative embodiment of FIGS. 20-26, the power button 312 is positioned below the row of input buttons 306, 308, 310, but the buttons 306, 308, 310, 312 may be positioned in other configurations and/or orientations in other embodiments.

As discussed above, the hand-held display module 14 is configured to be used with the sensor module 12 to receive joint force data form the module 12 and display indicia on the display 302 indicative of the joint forces of the patient's joint. Similar to the sensor module 12, the display module 14 may be configured to determine the relative medial-lateral balance of the joint force of the patient's joint and display indicia of such balances on the display 302. Additionally, the display module 14 may be configured to determine the anterior-posterior balance of the joint force of the patient's joint and display indicia of such balances on the display 302. Additionally, the display module 14 may also be configured to perform other functions such as store screenshots and data of the patient's joint forces as displayed on the display 302 and download such data to other devices.

Figure 14:
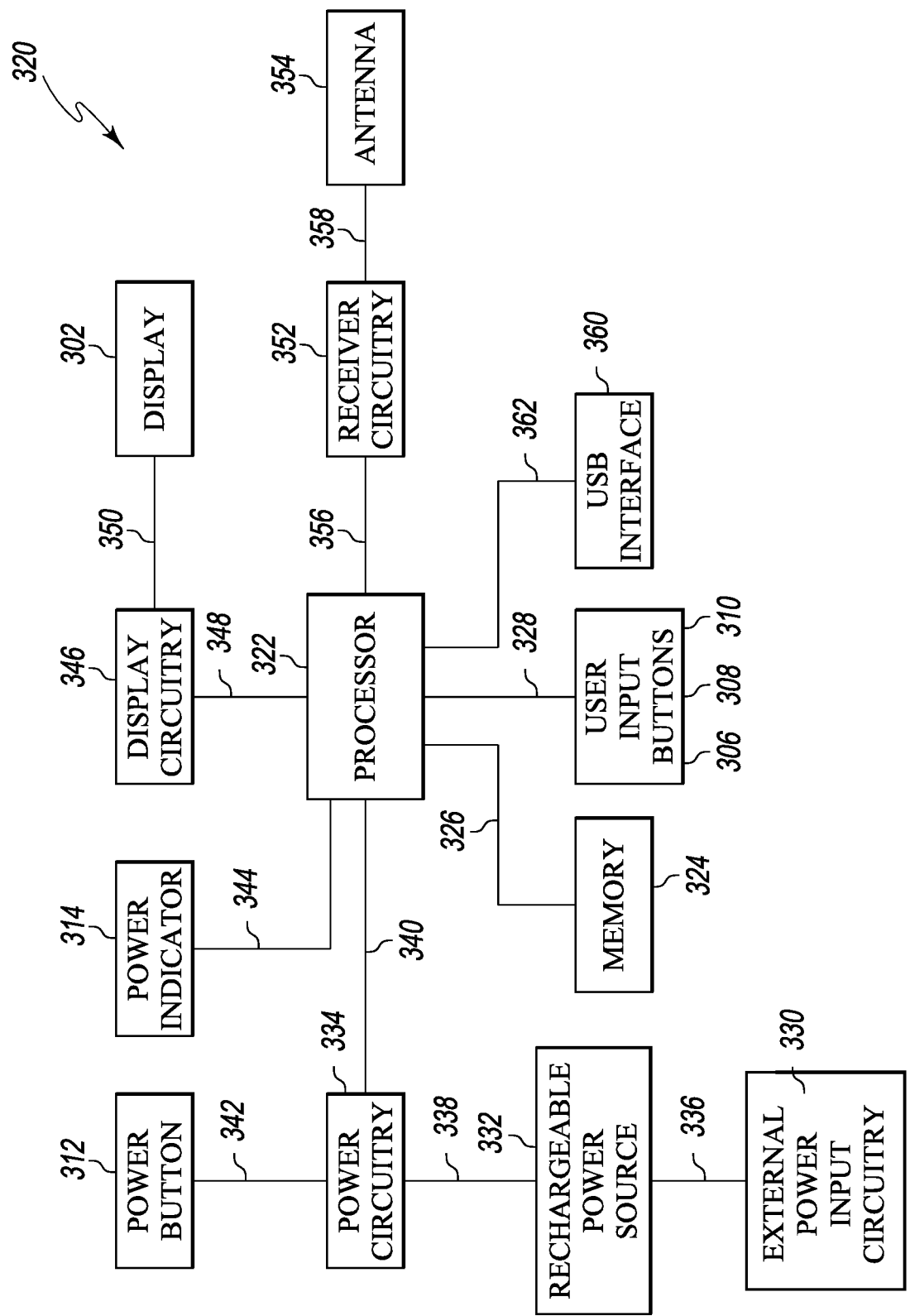
FIG. 14 is a simplified block diagram of one embodiment of an electrical circuit of the display module of FIG. 12.

As illustrated in FIG. 14, the hand-held display module 14 includes a control circuit 320 positioned in the housing 300. The control circuit 320 includes a processor 322 and a memory device 324. The processor 322 may be embodied as any type of processor configurable to perform the functions described herein. For example, the processor 322 may be embodied as a separate integrated circuit or as a collection of electronic devices. Additionally, the processor may be a single or multi-core processors. Although only a single processor 322 is illustrated in FIG. 14, it should be appreciated that in other embodiments, the control circuit 320 may include any number of additional processors. The memory device 324 may be embodied read-only memory devices and/or random access memory devices. For example, the memory device 324 may be embodied as or otherwise include electrically erasable programmable memory devices (EEPROM), dynamic random access memory devices (DRAM), synchronous dynamic random access memory devices (SDRAM), double-data rate dynamic random access memory devices (DDR SDRAM), and/or other volatile or non-volatile memory devices. Additionally, although only a single memory device is illustrated in FIG. 14, in other embodiments, the control circuit 320 may include additional memory devices.

The processor 322 is communicatively coupled to the memory device 324 via signal paths 326. The signal paths 326 may be embodied as any type of signal paths capable of facilitating communication between the processor 322 and the memory device 324. For example, the signal paths 326 may be embodied as any number of wires, printed circuit board traces, via, bus, intervening devices, and/or the like.

The processor 322 is also communicatively coupled to the user input buttons 306, 308, 310 via signal paths 328 and to a power indicator 314 via signal paths 344. Similar to signal paths 326, the signal paths 328, 344 may be embodied as any type of signal paths capable of facilitating communication between the processor 322 and the user input buttons 306, 308, 310 and the power indicator 314, respectively. For example, the signal paths 328, 344 may include any number of wires, printed circuit board traces, via, bus, intervening devices, and/or the like. The user input buttons 306, 308, 310 are software or "soft" buttons, the functionality of each of which may be determined based on the particular screen displayed on the display 302.

The control circuit 320 also includes an external power input circuitry 330, a rechargeable power source 332 such as a rechargeable battery or the like, and power circuitry 334. The external power input circuitry 330 is configured to receive a plug of a charger such as a "wall charger" and is communicatively coupled to the rechargeable power source 332 via signal paths 336. The rechargeable power source 332 is communicatively coupled to the power circuitry 334 via signal paths 338. The power circuitry 334 is communicatively coupled to the processor 332 via signal paths 340 and to the power button 312 via signal paths 342. The signal paths 336, 338, 340, 342 may be embodied as any type of signal paths including, for example any number of wires, printed circuit board traces, via, bus, intervening devices, and/or the like. The power circuitry 334 may include power control, distribution, and filtering circuitry and is configured to provide or distribute power the rechargeable power source 332 to the processor 322 and other devices or components of the control circuit 320.

The control circuit 320 also includes display circuitry 346 for driving and/or controlling the display 392. The display circuitry 346 is communicatively coupled to the processor 322 via signal paths 348 and to the display 302 via signal paths 350. The signal paths 348, 350 may be embodied as any type of signal paths capable of facilitating communication between the processor 322 and display circuitry 346 and the display circuit 346 and display 302, respectively. For example, the signal paths 348, 350 may be embodied as any number of wires, printed circuit board traces, via, bus, intervening devices, and/or the like.

As discussed above, the hand-held display module 14 is configured to receive joint force data from the sensor module 12. As such the control circuit 320 includes receiver circuitry 352 and an antenna 354. The receiver circuitry 352 is communicatively coupled to the processor 322 via signal paths 356 and to the antenna 354 via signal paths 358. The signal paths 356, 358 may be embodied as any type of signal paths capable of facilitating communication between the receiver circuitry 352 and the processor 322 and the antenna 354, respectively. For example, the signal paths 356, 358 may be embodied as any number of wires, printed circuit board traces, via, bus, intervening devices, and/or the like. The receiver circuitry 352 may be configured to use any type of wireless communication protocol, standard, or technologies to receive the joint force data from the sensor module 12. For example, as discussed above in regard to the sensor module 12, the display module 14 may be configured to a wireless networking protocol, a cellular communication protocol such as a code division multiple access (CDMA) protocol, a Bluetooth® protocol, or other wireless communication protocol, standard, or technology to communicate with the sensor module 12.

The control circuit 320 also includes a universal serial bus (USB) interface 360. The USB interface 360 is communicatively coupled to the processor 322 via signal paths 362, which may be embodied as any type of signal paths capable of facilitating communication between the USB interface 360 and the processor 322. For example, the signal paths 362 may be embodied as any number of wires, printed circuit board traces, via, bus, intervening devices, and/or the like. The USB interface 360 may be used to download data, such as joint force data or screenshot data, from the display module 14 to another device such as a computer. Additionally, the USB interface 360 may be used to update the software or firmware of the control circuit 320.

Referring now to FIGS. 23-26, in use, the control circuit 320 is configured to execute a method 400 for determining and displaying joint force data related to a patient's joint to an orthopaedic surgeon. The method 400 begins with block 402 in which the control circuit 320 is initialized. For example, in block 402, the control circuit 320 may perform any number of system checks, clear any registers of the processor 322, and/or perform other initialization and/or integrity checks. Additionally, in some embodiments, the control circuit 320 is configured to perform a handshaking routine in block 404 with the sensor module 12. During this handshaking routine, the control circuit 320 and the sensor module 12 may be configured to determine communication protocols and/or otherwise establish any type of communication procedures for transmitting the joint force data from the sensor module 12 to the device module 14.

In block 406, the control circuit 320 receives the joint force data from the sensor module 12. As discussed above, the joint force data is indicative of the joint force of the patient's knee as indicated by the sensor signals generated by the sensor array 90 of the sensor module 12. In block 408, the control circuit 320 determines a medial joint force value and a lateral joint force value based on the joint force data received in block 406. The medial joint force value is based on the set of medial sensors 196 and the lateral joint force value is based on the set of lateral sensors 197. In block 410, the control circuit 320 determines the medial/lateral balance of the joint force of the patient's joint based on the medial and lateral joint force values. As discussed above, the medial/lateral balance may be represented by a percentage value. The medial/lateral balance of the joint force is subsequently displayed on the display 302 in block 412. For example, as illustrated in the screenshots 450, 452, 454 in FIGS. 24, 25, and 26, the medial joint force component percentage value 430 is displayed toward a medially designated side 460 of the display 302 and the lateral joint force component percentage value 432 is displayed toward a laterally designated side 462 of the display 302.

In blocks 414, 416, the control circuit 320 determines which mode the orthopaedic surgeon has selected. In the illustrative embodiment, the orthopaedic surgeon may select a first mode in which indicia of only the medial-lateral balance of the patient's joint forces is displayed on the display 302 or a second mode in which may indicia of the medial-lateral and the anterior-posterior balance of the patient's joint forces is displayed in the display 302. The user may switch between the two modes by selecting the appropriate user input buttons 306, 308, 310.

If the orthopaedic surgeon has selected the medial-lateral only mode, the method 400 advances to block 418 in which indicia of the medial-lateral balance of the joint force of the patient's knee joint are displayed on the display 302. To do so, as illustrated in FIG. 16, a screen display 450 is presented on the display 302 of the display module 14. The screen display 450 includes a background image 470, which is illustratively embodied as an image of a proximal end of a resected tibia. The control circuit 320 displays a balance bar 472 on the background image 470 and an icon 474 on the balance bar 472 in a position that indicates the relative medial-lateral balance of the joint forces of the patient's joint. For example, in the illustrative screen display 450, the icon 474, which is embodied as a rounded rectangle, is displayed on the balance bar 472 toward the lateral side 462 of the screen display 450 (i.e., the side of the display 302 corresponding to the lateral side of the resected tibia image 470, which illustrative corresponds to the right side of the display 302). Such positioning indicates that the lateral force component of the total joint force of the patient's knee joint is greater than the medial joint force component. The farther way the icon 474 is located from the center of the balance bar 472, the greater the respective medial or lateral force component. In some embodiments, the background image 470 includes a "balanced" icon 476, illustratively embodied as a rounded rectangular outline, positioned on the background image 470 such that when the icon 474 is located within the boundaries of the icon 476, the medial joint force and the lateral joint force of the patient's knee are balanced or within a predetermined threshold of each other. Additionally, in some embodiments, the screen display 450 may include a total force fill bar 434, which may be filled or unfilled as the total force balance is increased or decreased depending on the particular configuration of the display 450.

If, however, the orthopaedic surgeon has selected the medial-lateral and anterior-posterior mode, the method 400 advances to block 420 in which indicia of the medial-lateral and anterior-posterior balance of the joint force of the patient's knee are displayed on the display 302. To do so, as illustrated in FIG. 17, a screen display 452 is presented on the display 302 of the display module 14. The screen display 450 includes the background image 470 on which the balance bar 472 is overlaid. Again, the control circuit 320 displays the icon 474 in a on the balance bar 472 indicative of the relative medial-lateral balance of the joint force of the patient's joint. In addition, however, a medial end 480 of the balance bar 472 and a lateral end 482 of the balance bar 472 are positioned based on the corresponding anterior-posterior balance. For example, the medial end 480 of the balance bar 472 is positioned toward the posterior side 464 of the display 302 or the anterior side 466 of the display 302 based on the anterior-posterior balance of the medial joint force. As discussed above, the anterior-posterior balance of the medial joint force component may be determined based on the sensor signals from the set of medial-anterior sensors 180 and the set of medial-posterior sensors 184. Similarly, the lateral end 482 of the balance bar 472 is positioned toward the posterior side 464 of the display 302 or the anterior side 466 of the display 302 based on the anterior-posterior balance of the lateral joint force. As discussed above, the anterior-posterior balance of the lateral joint force component may be determined based on the sensor signals from set of lateral-anterior sensors 182 and the set of lateral-posterior sensors 186.

Figure 18:
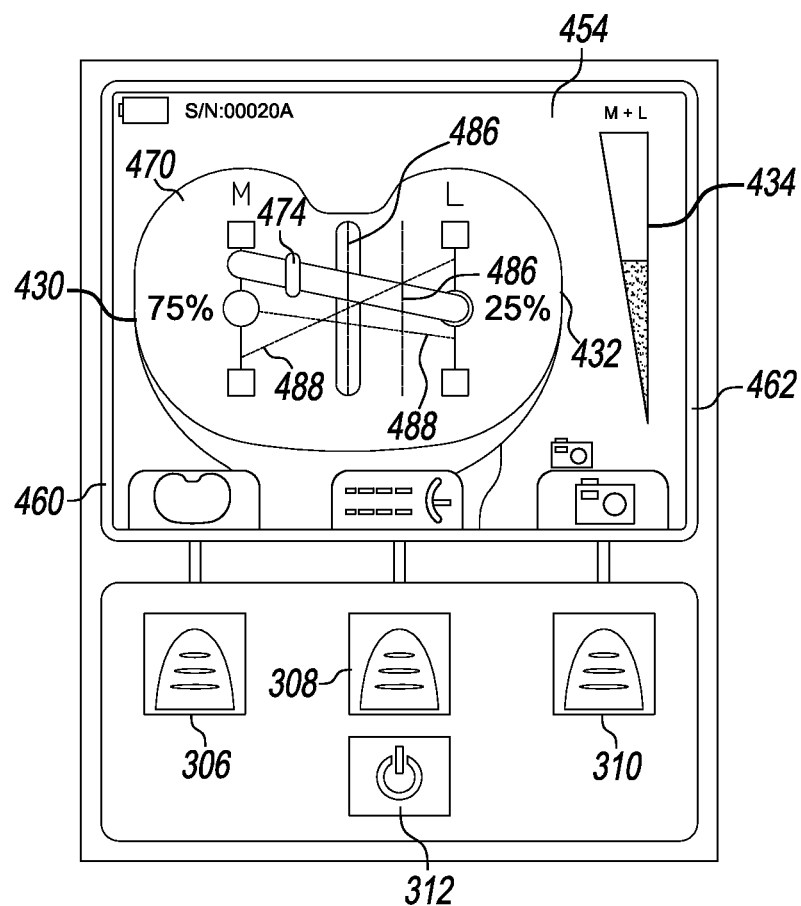

In the illustrative screen display 452 of FIG. 18, the medial end 480 of the balance bar 472 is positioned toward the anterior side 466 of the display 302 and the lateral end 482 of the balance bar 472 is positioned toward the posterior side 464 of the display 302. Such positioning indicates that the anterior force component of the medial force component is greater than the posterior force component of the medial force component and that the posterior force component of the lateral force component is greater than the anterior force component of the lateral force component. The farther way the ends 480, 482 are from the anterior-posterior center, the greater the respective anterior or posterior force component.

Figure 15:
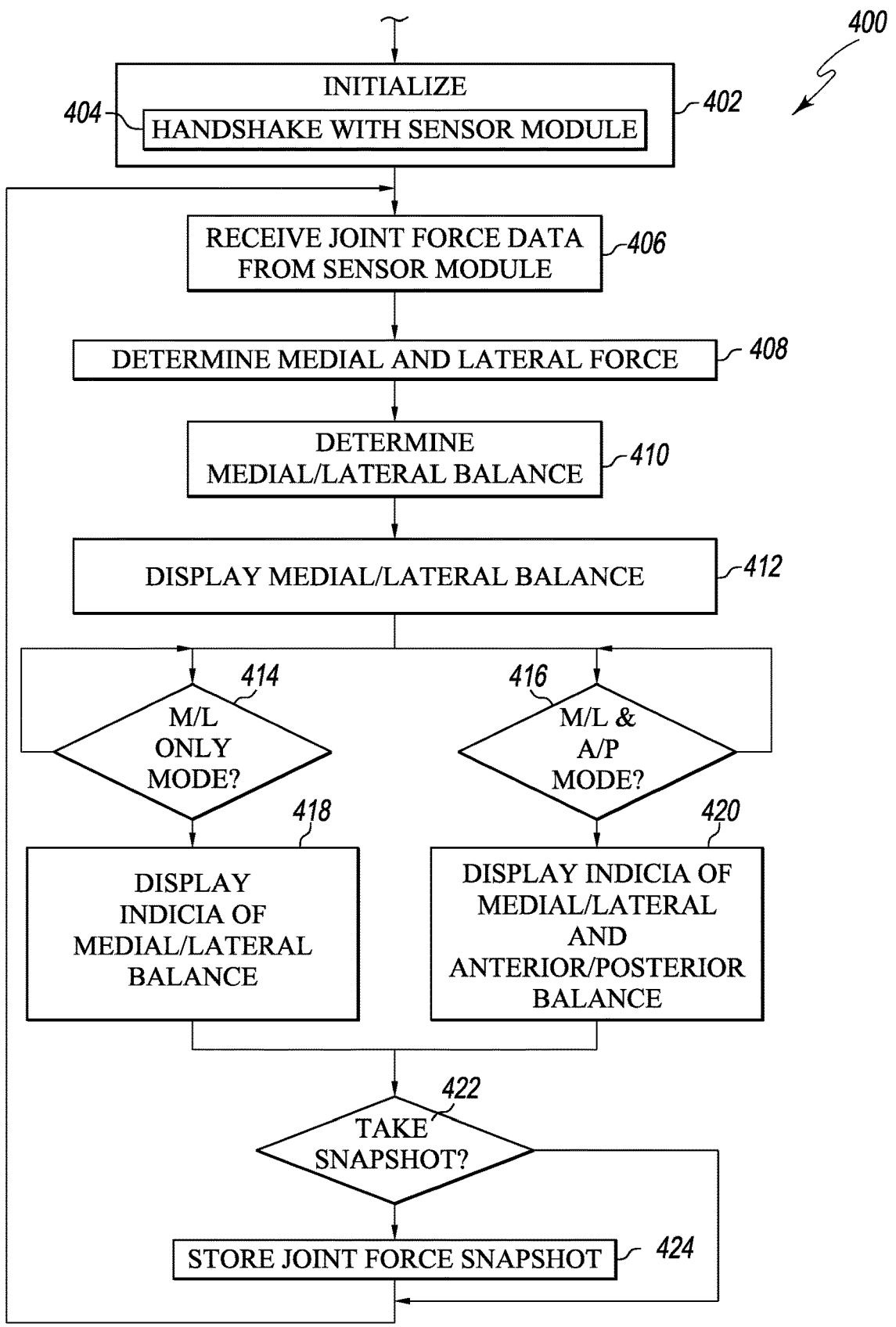
FIG. 15 is a simplified flow diagram of one embodiment of a method for displaying joint force data that may be executed by the display module of FIG. 12.

Referring now back to FIG. 15, once the appropriate indicia of the joint force balances have been displayed on the display 302, the control circuit 320 determines whether the orthopaedic surgeon would like to take a snapshot of the current display in block 422. The orthopaedic surgeon may take a screenshot of the display 302 by selecting the appropriate user input button 306, 308, 310. Additionally, the screenshot is stored in the memory device 324 in block 424 and may be subsequently downloaded from the display module 14.

When a screenshot is stored, an icon 484 appears in the lower right corner of the display 302. In addition to the icon 484, in some embodiments, a corresponding vertical balance line 486 is displayed on the display 302 when a screenshot is stored. The balance line 486 provides a visual indication of the medial-lateral balance of the joint force displayed in the associated stored screenshot. Further, if the orthopaedic surgeon has selected the medial-lateral and anterior-posterior mode, an anterior-posterior balance line 488 is displayed on the display 302. The balance line 488 provides a visual indication of the anterior-posterior balance of the medial and lateral forces of the patient's knee joint displayed in the associated stored screenshot.

Referring now to FIGS. 19-27, in some embodiments, the sensor module 12 may be used with a tibial trialing system 500. The tibial trialing system 500 includes an adaptor 502 and one or more tibial trialing components configured be positioned over the adaptor 502 on the tibial paddle 34 as discussed in more detail below. In the illustrative embodiment, the tibial trialing components of the system 500 may include, for example, one or more trialing shims 504, tibial bearing surface trials 505 that may be coupled to the trialing shims 504, and/or one or more tibial bearing trials 506. In some embodiments, the tibial bearing trials 506 may be configured to receive the adaptor 502 as discussed below with regard to FIGS. 26 and 27, while the tibial bearing surface trials 505 may be configured to couple to a selected trialing shim 504. For example, tibial bearing surface trial 505 may include a pair of lugs or protrusions (not shown) shaped and located to be received in a pair of corresponding apertures 508 of the trialing shim 504 to couple the tibial bearing trial surface trial 505 to the trialing shim 504, thereby forming a modular tibial bearing trial.

As discussed above, the adaptor 502 is configured to couple or otherwise connect to the tibial paddle 34 of the sensor module 12. As shown in FIGS. 20A-20E, the adaptor 502 includes a hub 510 having a bottom side 512, which contacts or otherwise confronts the tibial paddle 34 when the adaptor 502 is couple thereto, and a top side 514 opposite the bottom side 512. Illustratively, the hub 510 has a circular shape, or near-circular shape. However, in other embodiments, the hub 510 may be formed to have other geometric shapes capable of facilitating rotation of attached rotatable tibial trialing components as discussed in more detail below. Additionally, the illustrative adaptor 502 is formed from a plastic material, but may be formed from other materials having enough flexibility to allow the clip to be coupled to the tibial paddle 34 and any tibial trialing component while retaining such coupling during use.

A set of upper retainer clips 516 extend upwardly from the top side 514. Each upper retainer clip 516 includes an elongated stem 518 attached to the hub 510 and a lip or nub 520 attached to a distal end of the elongated stem 518. The elongated stem 518 extends upwardly from the hub 510, and the associated lip 520 extends outwardly from the distal end of the elongated stem 518. Each of the upper retainer clips 516 is inwardly curved in the transverse plane (i.e., the plane of the tibial paddle 34 when the adaptor 502 is coupled thereto) and is arranged to generally define a circle. Additionally, each lip or nub 520 has a curved or rounded exterior surface. As discussed in more detail below, the upper retainer clips 516 are shaped and configured to facilitate attachment and detachment of a spacer block 832 and/or the joint distractor 16 during a surgical procedure. Although the illustrative adaptor 502 includes three upper retainer clips 516, additional or fewer upper retainer clips 516 may be used in other embodiments.

Similar to the upper retainer clips 516, a set of lower retainer clips 522 extend downwardly from the bottom side 512. Each lower retainer clip 522 includes an elongated stem 524 attached to the hub 510 and a lip or nub 526 attached to a distal end of the elongated stem 524. The elongated stem 524 extends downwardly from the hub 510, and the associated lip 526 extends outwardly from the distal end of the elongated stem 524. Each of the lower retainer clips 522 is inwardly curved in the transverse plane (i.e., the plane of the tibial paddle 34 when the adaptor 502 is coupled thereto) and is arranged to generally define a circle. Additionally, each lip or nub 526 has a number of substantially planar exterior surfaces that intersect at selected angles. It should be appreciated that in other embodiments the nub 526 may include curved or rounded exterior surfaces. As discussed in more detail below, the lower retainer clips 522 are shaped and configured to facilitate attachment and detachment of the adaptor 502 to the tibial paddle 34 of the sensor module 12. To do so, the lower retainer clips 522 are received in the vertical aperture 45 of the tibial paddle 34. Although the illustrative adaptor 502 includes three lower retainer clips 522, additional or fewer lower retainer clips 522 may be used in other embodiments.

The upper retainer clips 516 and the lower retainer clips 522 are "keyed" such that the adaptor 502 is couplable to the tibial paddle 34 in a single vertical orientation. In the illustrative embodiment, the upper retainer clips 516 are larger than the lower retainer clips 522 such that the upper retainer clips 516 cannot be inserted into the vertical aperture 45 of the tibial paddle 34. For example, the upper retainer clips 516 generally define circle 550 (see FIG. 20E) having a diameter greater than a circle 552 generally defined by the lower retainer clips 522 (see FIG. 20D). Of course, other structures or features may be used in other embodiments to "key" the adaptor 502 to the tibial paddle 34.

As shown in FIG. 20B, the adaptor 502 also includes an anterior alignment tab 530 and a posterior alignment tab 532, which extend downwardly from the bottom side 514. As discussed in more detail below, the alignment tabs 530, 532 are configured to be received in the corresponding alignment apertures 46, 48 of the tibial paddle (see FIG. 19) when the adaptor 502 is coupled to the tibial paddle 34. The alignment tabs 530, 532 are "keyed" such that the adaptor 502 is attachable to the tibial paddle 34 in a single orientation. For example, in the illustrative embodiment, the anterior alignment tab 530 has a greater width or arc length 534 than the width or arc length 536 of the posterior tab 532 (see FIG. 20D). Similarly, as discussed above, the anterior alignment aperture 46 of the tibial paddle 34 has a greater width or arc length than the posterior alignment aperture 48. As such, the adaptor 502 is attachable to the tibial paddle 34 only in the orientation in which the anterior alignment tab 530 is received in the anterior alignment aperture 46 and the posterior alignment tab 532 is received in the posterior alignment aperture 48. Each of the alignment tabs 530, 532 are inwardly curved in the transverse plane and include angled sides 538, 540, respectively, which facilitate the auto-detachment of the adaptor 502 from the tibial paddle 34 in response to excessive torque being exerted on the adaptor 502 as discussed in more detail below.

The adaptor 502 also includes an anti-rotation key or protrusion 542, which extends outwardly from the hub 510. The anti-rotation key 542 includes a bottom surface 544 that is co-planer with the bottom side 512 of the hub 510 such that the anti-rotation key 542 rests on, contacts, or otherwise confronts the tibial paddle 34 when the adaptor 502 is coupled to the sensor module 12. In the illustrative embodiment, the anti-rotation key 542 has a rectangular shape, but may have other shapes in other embodiments. As discussed in more detail below, the anti-rotation key 542 prevents or restricts rotation of non-mobile tibial trial components and limits the rotation of mobile tibial trial components.

Figure 21:
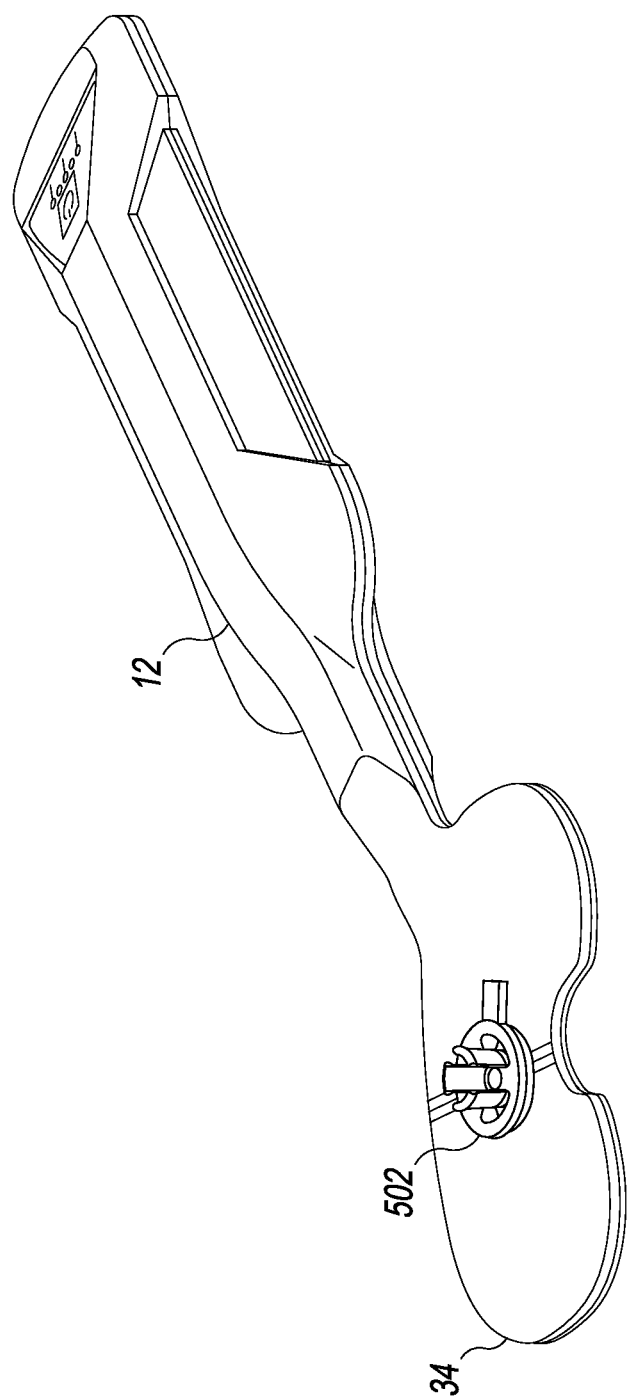
FIG. 21 is a perspective view of the adaptor of FIG. 20 coupled to the sensor module of FIG. 2.
Figure 22:
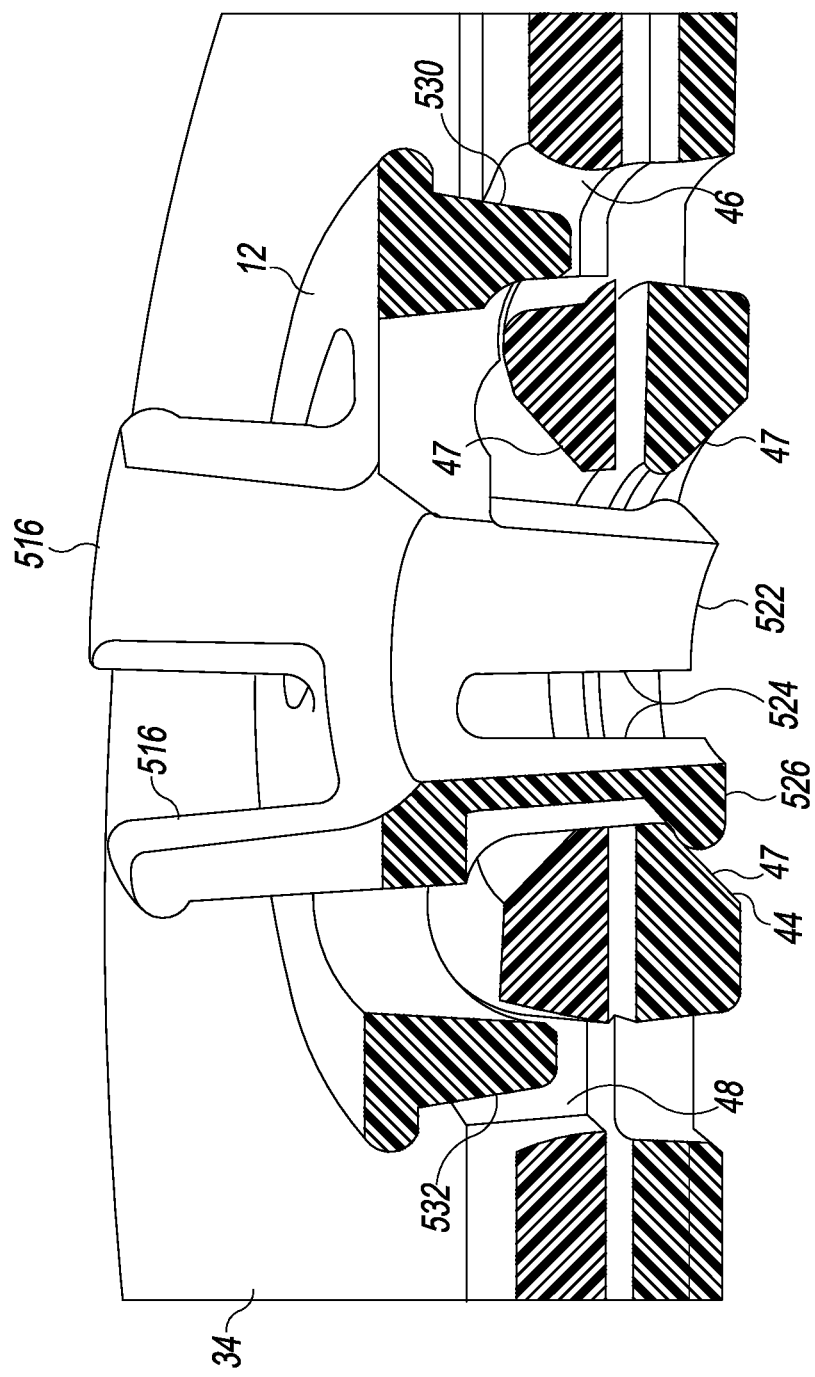
FIG. 22 is a cross-sectional view of the adapter and sensor module of FIG. 21.

As discussed above, the adaptor 502 is configured to be attached to the tibial paddle 34 of the sensor module 12 as shown in FIG. 21. To do so, the lower retainer clips 522 are inserted into the vertical aperture 45 of the tibial paddle 34, and the adaptor 502 is aligned such that the anterior alignment tab 530 is received in the anterior alignment aperture 46 and the posterior alignment tab 532 is received in the posterior alignment aperture 48 of the tibial paddle 34 as shown in FIG. 22. The lower retainer clips 522 are configured to flex inwardly slightly to allow attachment of the adaptor 502 to the tibial paddle 34. Upon successful insertion, the lower retainer clips 522 return to their normal, or near normal, position to provide an amount of lift-off resistance to thereby secure the adaptor 502 to the tibial paddle 34. As shown in FIG. 22, the lip or nub 526 contact the inwardly angled section 47 of the inner sidewall 44 of the tibial paddle 34, which provides an amount of lift-off resistance for the adaptor 502. However, if excessive torque is applied to the adaptor 502, the inwardly angled section 47 of the inner sidewall 44 of the tibial paddle 34 facilitates the detachment of the adaptor 502 by forcing the lower retainer clips 522 inwardly as discussed in more detail below.

Figure 25:
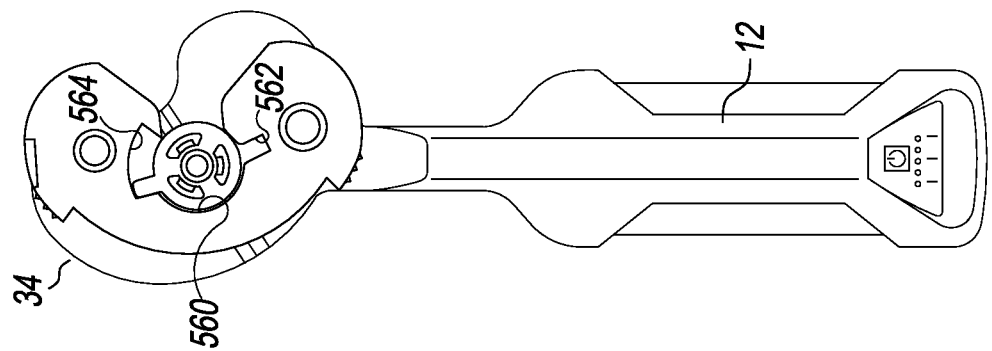
FIG. 25 is a top plan view of the spacer block of FIG. 23 coupled to the sensor module and adaptor of FIG. 21 in a rotating orientation and rotated to an opposite maximum rotation position relative to FIG. 24.
Figure 24:
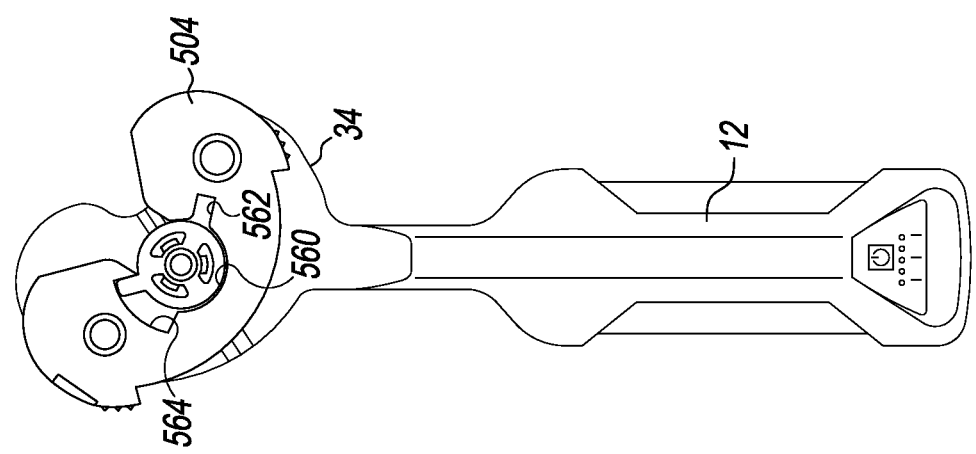
FIG. 24 is a top plan view of the spacer block of FIG. 23 coupled to the sensor module and adaptor of FIG. 21 in a rotating orientation and rotated to a maximum rotation position.
Figure 23:
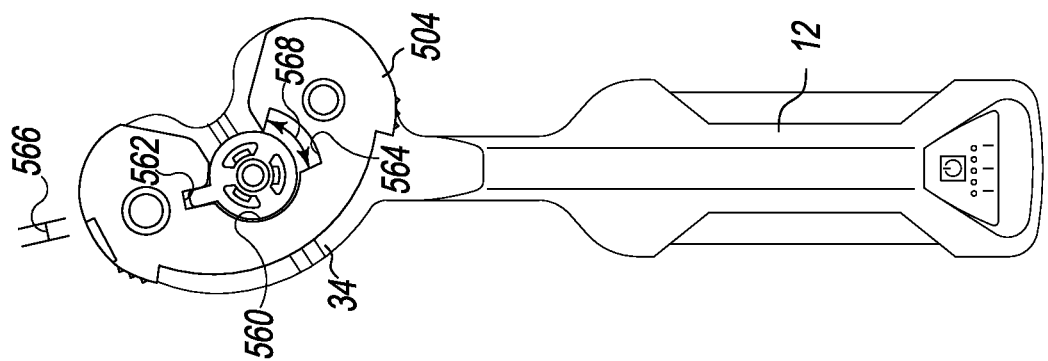
FIG. 23 is a top plan view of a spacer block of FIG. 19 coupled to the sensor module and adaptor of FIG. 21 in a non-rotating orientation.

As shown in FIGS. 23-25, the trialing shim 504 may be coupled to the adaptor 502 and sensor module 12 in a fixed (FIG. 23) or mobile (FIGS. 24 and 25) orientation. To facilitate such orientations, the trialing shim 504 includes a central aperture 560 sized and shaped to receive the hub 510 of the adaptor 502. Additionally, the trialing shim 504 includes a anti-rotation aperture 562 and a rotation-enabling aperture 564, each in fluid communication with the central aperture 560. As shown in FIG. 23, anti-rotation aperture 562 has a width 566 slightly larger than the anti-rotation key 542 of the adaptor 502 such that the anti-rotation key 542 is receivable in the anti-rotation aperture 562. Conversely, the rotation-enabling aperture 564 has a generally trapezoidal shape and an arc length 568 that is substantially greater than the width of the anti-rotation key 542.

Figure 34:
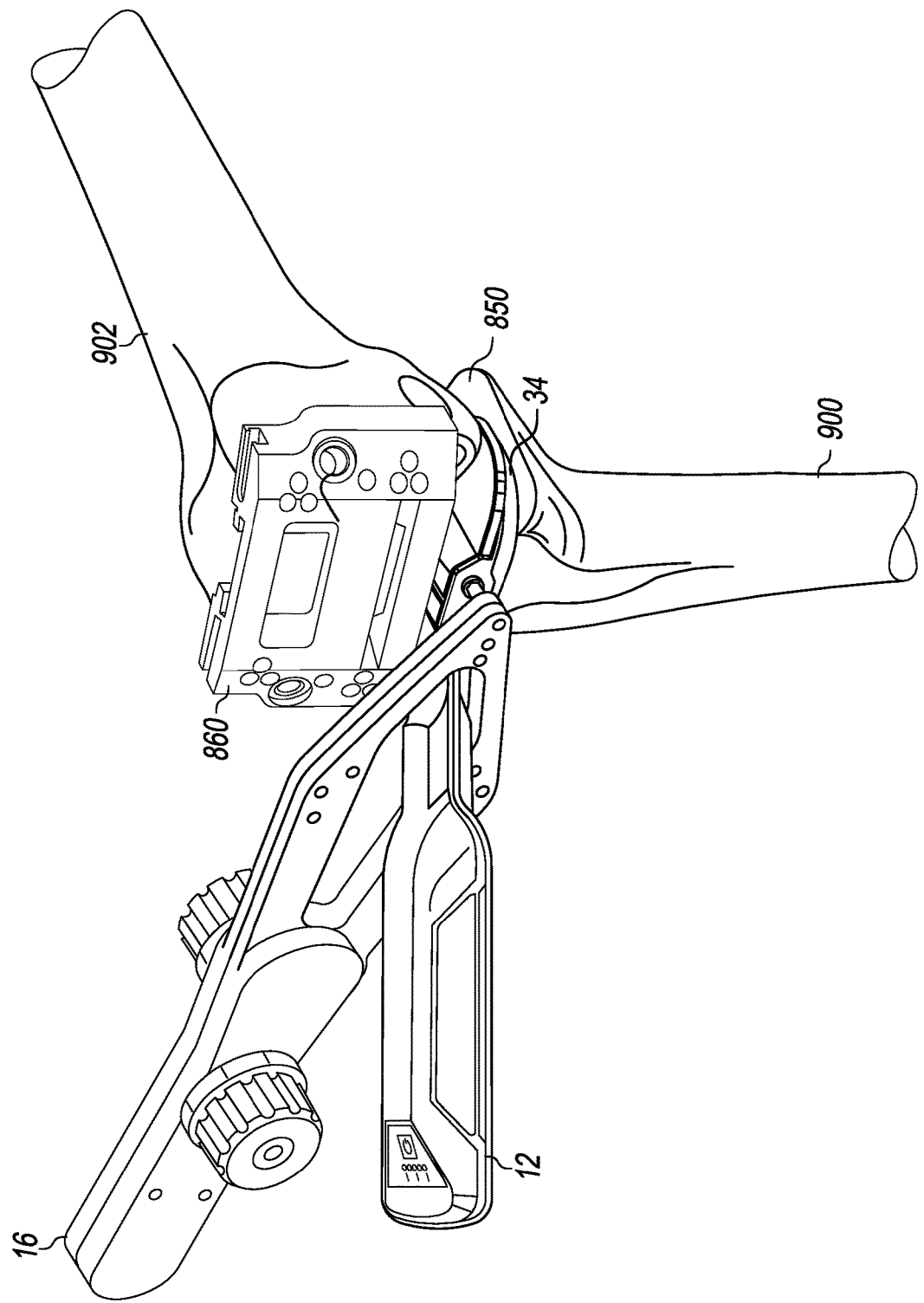
FIG. 34 is a perspective view of a patient's joint during an orthopaedic surgical procedure using the distractor and sensor module of FIG. 1.
Figure 35:
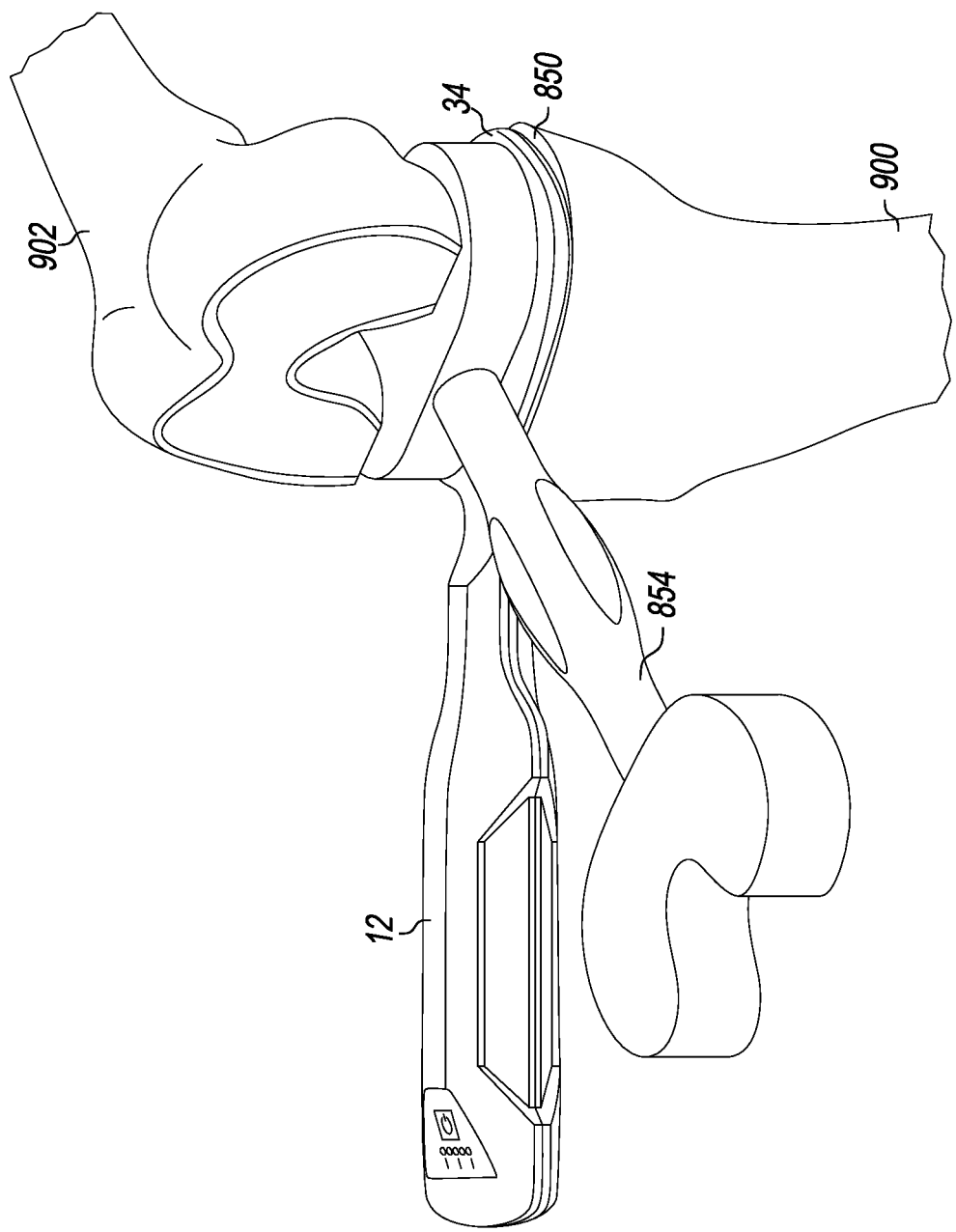
FIG. 35 is another perspective view of a patient's joint in flexion during an orthopaedic surgical procedure using the sensor module of FIG. 2.

As shown in FIG. 23, the trialing shim 504 may be coupled to the adaptor 502 and the sensor module 12 in a fixed orientation such that the anti-rotation key 542 of the adaptor 502 is received in the anti-rotation aperture 562 of the trialing shim 504. Because the anti-rotation aperture 562 is only slightly larger than the anti-rotation key 542, substantial rotation of the trialing shim 504 relative to the tibial paddle 34 is restricted or otherwise prevented. Alternatively, as shown in FIGS. 34 and 35, the trialing shim 504 may be coupled to the adaptor 502 and the sensor module 12 in a mobile orientation such that the anti-rotation key 542 of the adaptor 502 is received in the rotation-enabling aperture 564 of the trialing shim 504. Because the rotation-enabling aperture 564 is significantly larger than the anti-rotation key 542, rotation of the trialing shim 504 relative to the tibial paddle 34 is facilitated or otherwise allowed.

In either the fixed or mobile orientation, the application of an excessive torque to the adaptor 502 causes the adaptor 502 to detach from the tibial paddle 34. That is, as the excessive torque is applied to the adaptor 502, the angled sides 538, 540 of the alignment tabs 530, 532 engage the corresponding angled sides of the alignment apertures 46, 48, which generates a lift-off force. The lift-off force, in turn, causes the lower retainer clips 522 to be pushed inwardly via the inwardly angled section 47 of the inner sidewall 44 of the tibial paddle 34. As such, the adaptor 502 is auto-detached from the tibial paddle 34. In this way, damage to the adaptor 502 and sensor module 12 may be avoided.

Figure 26:
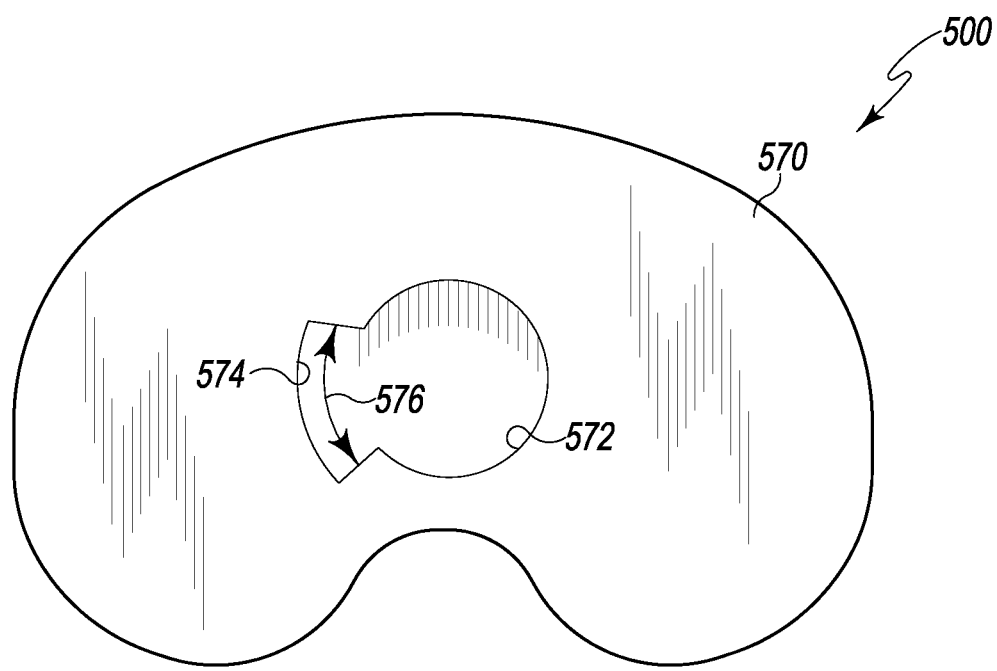
FIG. 26 is a bottom plan view of a mobile tibial trial of FIG. 19 having rotation key aperture.

As discussed above, the tibial bearing trial 506 may be configured to couple to the adaptor 502. The tibial bearing trial 506 may be embodied as a fixed or mobile bearing trial. For example, as shown in FIG. 26, a mobile tibial bearing trial 570 includes a central aperture 572 sized and shaped to receive the hub 510 of the adaptor 502 and a rotation-enabling aperture 574 in fluid communication with the central aperture 572. Similar to the rotation-enabling aperture 564 of the trialing shim 504, the rotation-enabling aperture 574 has a generally trapezoidal shape and an arc length 576 that is substantially greater than the width of the anti-rotation key 542. As such, when the mobile tibial bearing trial 570 is coupled to the adaptor 502 and sensor module 512, rotation of the mobile tibial bearing trial 570 relative to the tibial paddle 34 of the sensor module 512 is facilitated or otherwise allowed.

Figure 27:
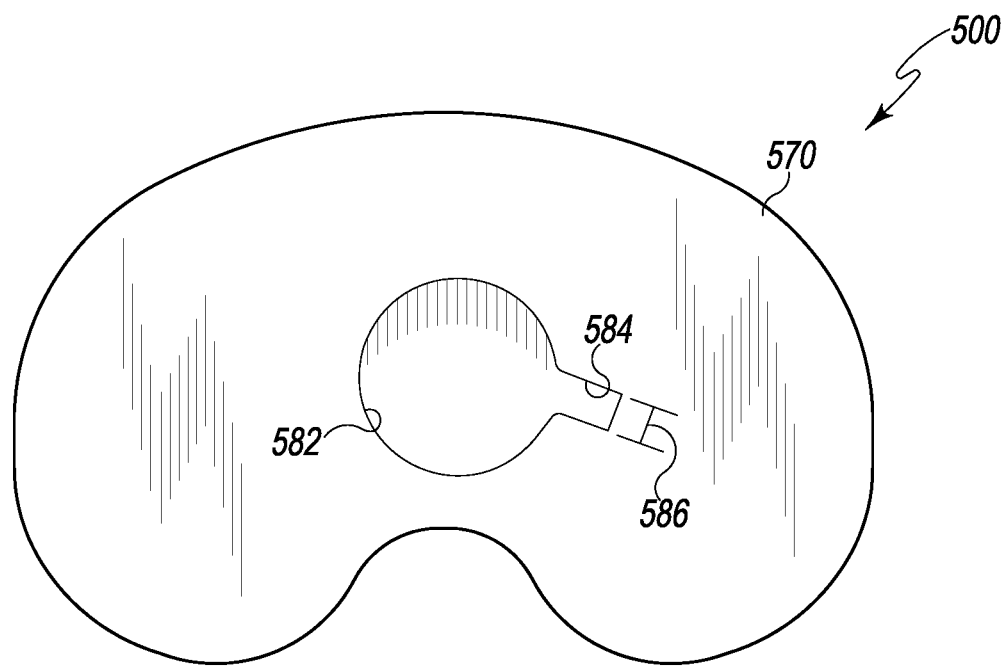
FIG. 27 is a bottom plan view of a fixed tibial trial having a non-rotation key aperture.

Alternatively, the tibial bearing trial 506 may be embodied as a fixed tibial bearing trial 580 as shown in FIG. 27. The fixed tibial bearing trial 580 includes a central aperture 582 sized and shaped to receive the hub 510 of the adaptor 502 and an anti-rotation aperture 584 in fluid communication with the central aperture 582. Similar to the anti-rotation aperture 562 of the trialing shim 504, the anti-rotation aperture 584 has a width slightly greater than the width of the anti-rotation key 542 of the adaptor 502 such that the anti-rotation key 542 is receivable in the anti-rotation aperture 562. As such, when the fixed tibial bearing trial 580 is coupled to the adaptor 502 and sensor module 512, rotation of the fixed tibial bearing trial 580 relative to the tibial paddle 34 of the sensor module 512 is restricted or otherwise prevented.

Figure 28:
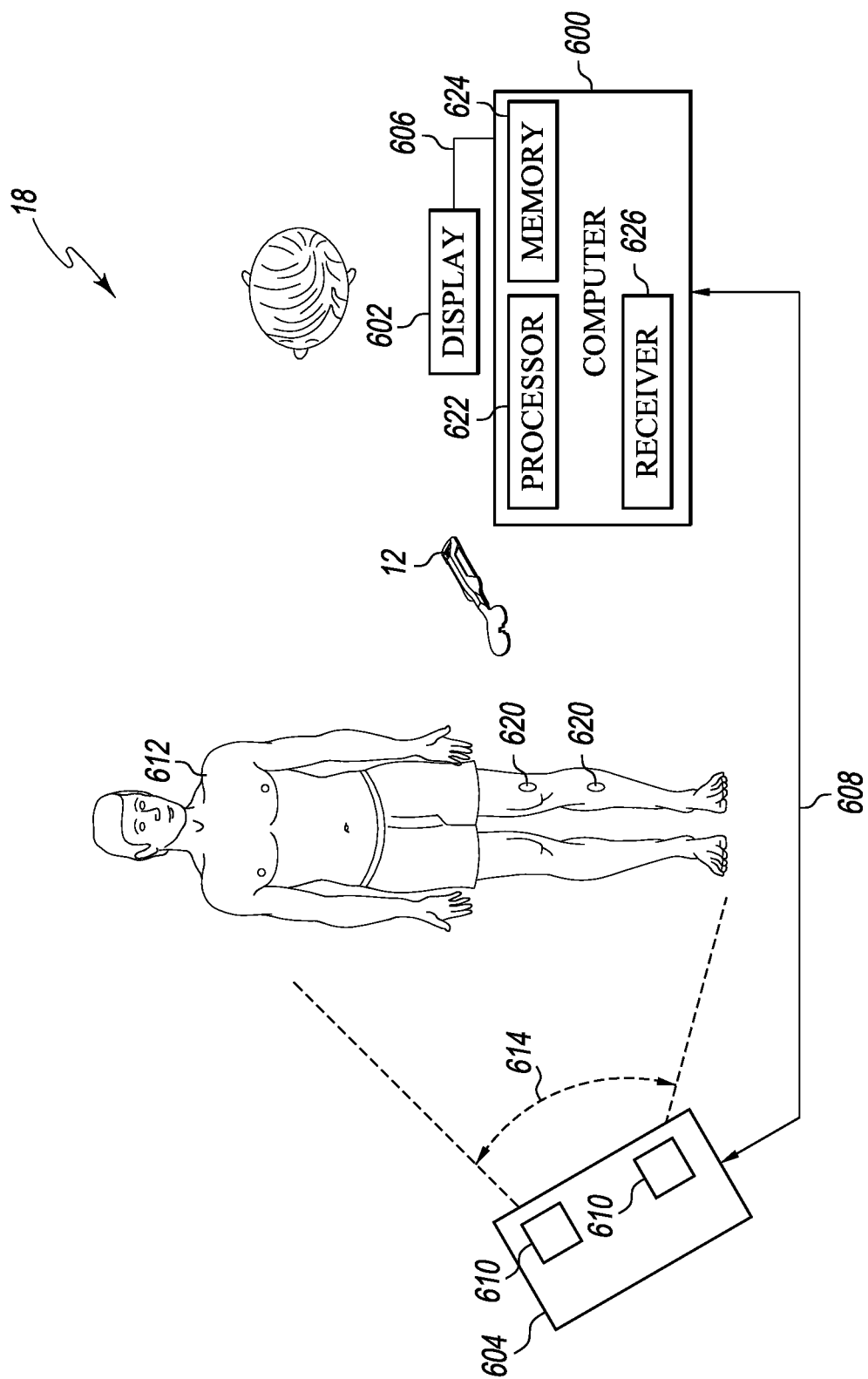
FIG. 28 is a simplified block diagram of one embodiment of a computer assisted surgery system of the system of FIG. 1.

Referring now to FIGS. 28-31, in some embodiments, the sensor module 12 may be configured for use with the computer assisted orthopaedic surgery (CAOS) system 18. In such embodiments, the sensor module 12 is configured to transmit the joint force data to the system 18. As illustrated in FIG. 28, the computer assisted orthopaedic surgery (CAOS) system 18 includes a computer 600, a display 602, and a camera unit 604. The computer 600 is communicatively coupled to the display 602 via signal paths 606 and to the camera unit 604 via signal paths 608. The signal paths 606, 608 may be embodied as any type of signal paths capable of facilitating electrical communication between the computer 600 and the display 602 and the computer 600 and the camera unit 604, respectively. For example, the signal paths may be embodied as any number of wires, printed circuit board traces, via, bus, intervening devices, and/or the like.

The display 602 may be embodied as any type of device such as a liquid crystal display monitor, a cathode ray tube (CRT) display monitor, or the like. Additionally, in some embodiments, the display 602 may be embodied as a "heads-up" display. In such embodiments, the signal path 606 may be embodied as a wired or wireless signal path. The camera unit 604 includes two or more cameras 610, which are positioned such that reflective arrays 620 coupled to the relevant bones of a patient 612 are in the field of view 614 of the cameras 610.

The computer 600 includes a processor 622, a memory device 624, and a receiver or receiver circuitry 626. The processor 622 may be embodied as any type of processor configurable to perform the functions described herein. For example, the processor 622 may be embodied as a separate integrated circuit or as a collection of electronic devices. Additionally, the processor may be a single or multi-core processors. Although only a single processor 622 is illustrated in FIG. 28, it should be appreciated that in other embodiments, the computer 600 may include any number of additional processors. The memory device 624 may be embodied read-only memory devices and/or random access memory devices. For example, the memory device 624 may be embodied as or otherwise include electrically erasable programmable memory devices (EEPROM), dynamic random access memory devices (DRAM), synchronous dynamic random access memory devices (SDRAM), double-data rate dynamic random access memory devices (DDR SDRAM), and/or other volatile or non-volatile memory devices. Additionally, although only a single memory device is illustrated in FIG. 28, in other embodiments, the computer 600 may include additional memory devices.

The receiver circuitry 626 may be configured to use any type of wireless communication protocol, standard, or technologies to receive the joint force data from the sensor module 12. For example, as discussed above in regard to the sensor module 12, the computer 600 may be configured to communicate using a wireless networking protocol, a cellular communication protocol such as a code division multiple access (CDMA) protocol, a Bluetooth® protocol, or other wireless communication protocol, standard, or technology to communicate with the sensor module 12.

In use, the computer assisted orthopaedic surgery (CAOS) system 18 is configured to provide surgical navigation by tracking and displaying the position of the patient's relevant bony anatomy (e.g., the patient's tibia and femur) to which the reflective arrays 620 are coupled and provide an amount of surgical procedure walk-through. Additionally, the computer assisted orthopaedic surgery (CAOS) system 18 is configured to receive the joint force data from the sensor module 12 and display the joint force data or other indicia of the joint forces of the patient's joint on the display 602.

Figure 29:
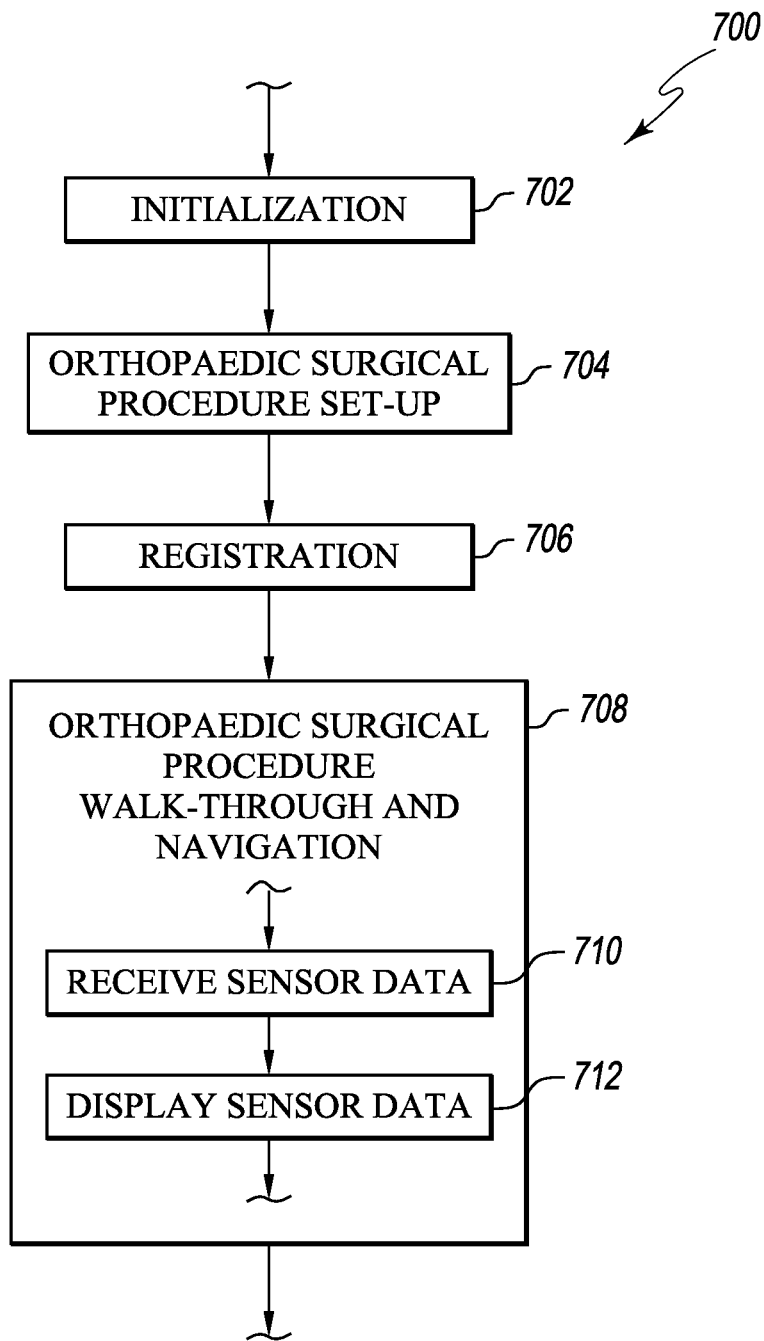
FIG. 29 is a simplified flow diagram of one embodiment of a method for performing an orthopaedic surgical procedure using the computer assisted surgery system of FIG. 28.

To do so, the computer 600 may execute a method 700 for performing an orthopaedic surgical procedure as illustrated in FIG. 29. The method 700 begins with block 702 in which the system 18 is initialized. For example, in block 702, the computer 600 may perform any number of system checks, clear any registers of the processor 622, and/or perform other initialization and/or integrity checks. Additionally, any number of settings, preferences, and calibrations of the CAOS system 18 may be established and performed in block 702. For example, the video settings of the display 602 may be selected, the language displayed by the computer 600 may be chosen, and the touch screen of the display device 602, if applicable, may be calibrated in block 702.

In block 704, the selections and preferences of the orthopaedic surgical procedure are chosen by the surgeon. Such selections may include the type of orthopaedic surgical procedure that is to be performed (e.g., a total knee arthroplasty), the type of orthopaedic implant that will be used (e.g., make, model, size, fixation type, etc.), the sequence of operation (e.g., the tibia or the femur first), and the like. Once the orthopaedic surgical procedure has been set up in block 704, the bones of the patient are registered in block 706. To do so, the reflective arrays 620 are coupled with the relevant bones of the patient (e.g., the tibia and femur of the patient). Additionally, the contours of such bones are registered using an appropriate registration tool. To do so, a pointer end of such tool is touched to various areas of the bones to be registered. In response to the registration, the computer 600 displays rendered images of the bones wherein the location and orientation of the bones are determined based on the reflective arrays coupled therewith and the contours of the bones are determined based on the registered points. Additionally, one or more surgical tools may be registered with the computer assisted orthopaedic surgery (CAOS) system in block 706.

Once the pertinent bones have been registered in block 706, the computer 600, in cooperation with the camera unit 604, displays the images of the surgical steps of the orthopaedic surgical procedure and associated navigation data (e.g., location of surgical tools) in block 708. To do so, the block 708 may include any number of sub-steps in which each surgical procedure step is displayed to the orthopaedic surgeon in sequential order along with the associated navigational data. Additionally, in block 710 the computer 600 receives joint force data from the sensor module 12. As discussed above, the joint force data is indicative of the joint force of the patient's knee as indicated by the sensor signals generated by the sensor array 90 of the sensor module 12.

In block 712, the computer 600 displays the joint force data or other data derived therefrom that is indicative of the joint forces of the patient's joint on the display 602. The computer 600 may be configured to determine any one or more joint force values based on the joint force data in block 712. For example, similar to the hand-held display module 14, the computer 600 may be configured to determine a medial joint force component value and a lateral joint force component value based on the joint force data received in block 710. Again, such medial joint force value is based on the sensor signals received from the pressure sensors 102, 104, 106, 108, 120, 124 and the lateral joint force value is based on the set of medial sensors 196 and the set of lateral sensors 197. In some embodiments, the computer 600 may also determine an average medial/lateral force value based on the medial joint force value and the lateral joint force value. In such embodiments, the medial joint force value, the lateral joint force value, and the average joint force value are subsequently displayed on the display 602 in block 712. In addition, the computer 600 may be configured to determine the medial-lateral and/or anterior-posterior balance of the joint forces based on the joint force data and display indicia of joint force balance on the display 602 in a manner similar to the hand-held display module 14. For example, the computer 600 may present displays similar to the displays 450, 452, 454 illustrated in and described above in regard to FIGS. 16, 17, and 18, respectively. in block 412.

Figure 30:
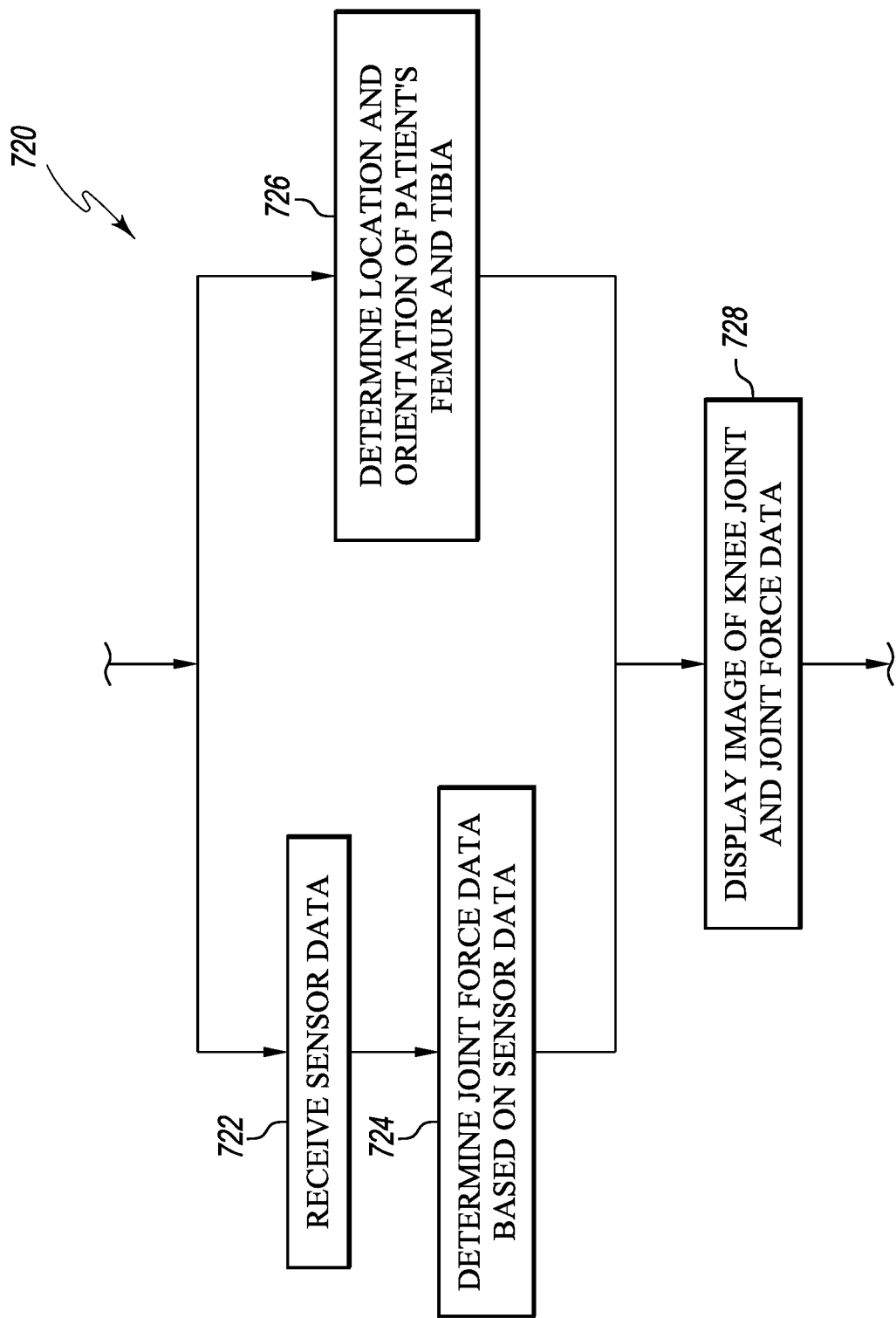
FIG. 30 is a simplified flow diagram of one embodiment of a method for determining and displaying navigation and joint force data that may be executed by the computer assisted surgery system of FIG. 28.

In some embodiments, the computer assisted orthopaedic surgery (CAOS) system 18 may be configured to determine and display joint force data on the display 602 in association with the navigation data. For example, the computer 600 may execute a method 720 for displaying joint force data in association with navigation data as illustrated in FIG. 30. The method 720 includes a block 722 in which the computer 600 receives joint force data from the sensor module 12. Again, the joint force data is indicative of the joint force of the patient's knee as indicated by the sensor signals generated by the sensor array 90 of the sensor module 12. In block 724, the computer 600 determines the medial, lateral, and/or average joint force values based on the joint force data received in block 722.

Contemporaneously with the determination of the joint force values in block 722, the computer 600 determines the location and orientation of the patient's relevant bones, such as the patient's femur and tibia in those embodiments wherein the patient's knee is undergoing an orthopaedic surgical procedure, in block 724. Subsequently, in block 728, the computer 600 displays the joint force values determined in block 722 and the image of the knee joint in block 728. As such, the computer 600 may be used to display, for example, the flexion and extension gaps of the medial and lateral condyles of the patient's knee and contemporaneously display the associated medial, lateral, and/or average joint force values of the patient's knee. By monitoring the flexion and extension gaps and the associated joint force values, the orthopaedic surgeon may determine the appropriate amount of gap or joint force for a particular orthopaedic procedure.

Additionally, in some embodiments, the computer 600 may also be configured to determine other anatomical data based on the orientation and position of the patients bones determined in block 726 and display such anatomical data along with the associated joint force values. For example, in one embodiment, the computer 600 is configured to determine the varus/valgus angle of the patient's knee and display the associated medial and lateral force values. Additionally, the computer 600 may be configured to determine the loaded condyle based on the medial and lateral force values and identify the loaded condyle to the orthopaedic surgeon on the display 602. Further, in some embodiments, the computer 600 may be configured to store the anatomical data, the joint force values, and/or other surgical data such as the implant type size, patient identification data, and/or the like in association with each other in the memory device 624 or other storage device.

Figure 31:
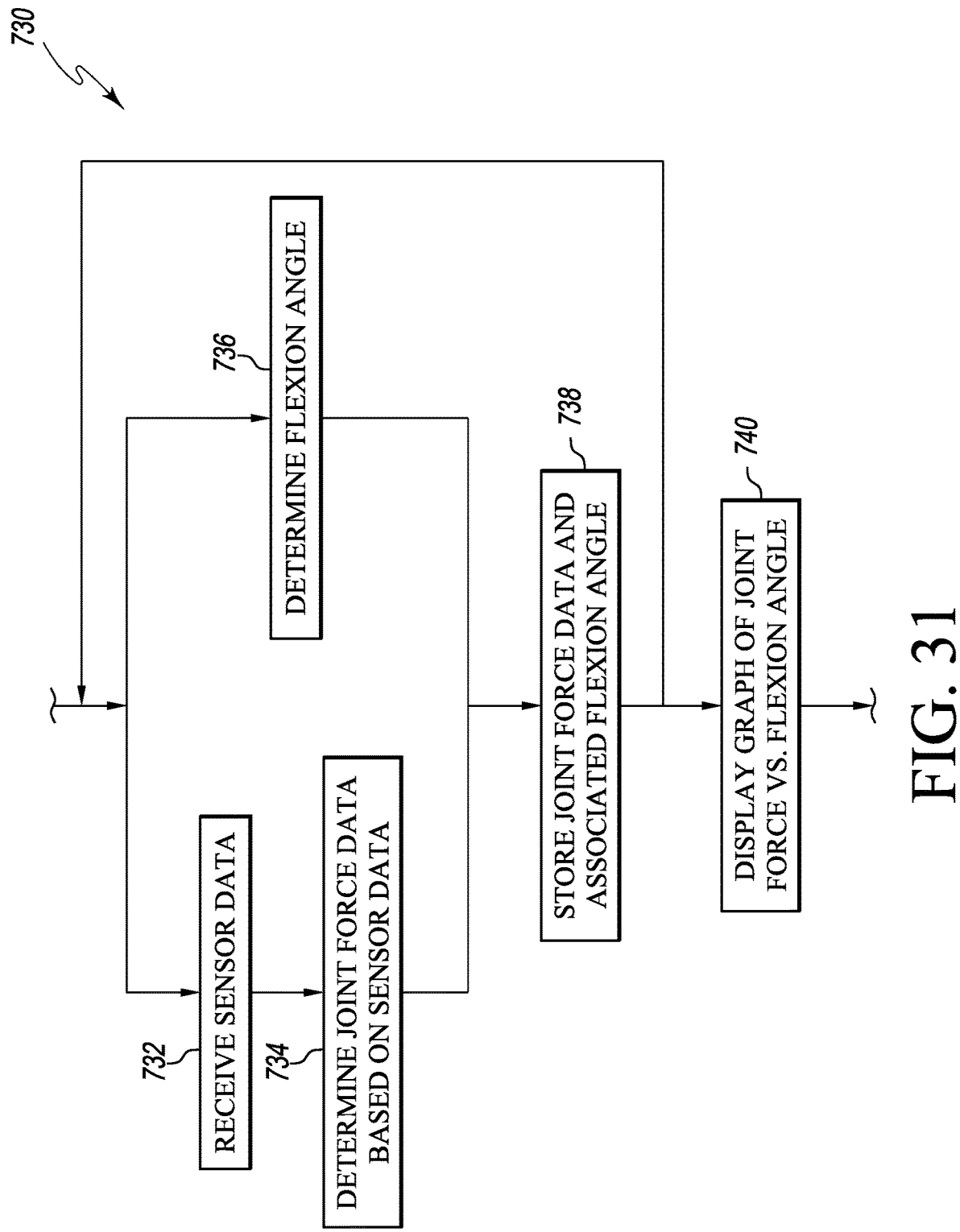
FIG. 31 is a simplified flow diagram of one embodiment of a method for determining and displaying flexion angle and force data of a patient's joint that may be executed by the computer assisted surgery system of FIG. 28.

The computer 600 may also be configured to determine and display a graph of flexion angle and associated joint force values in some embodiments. To do so, the computer 600 executes a method 730 as illustrated in FIG. 31. The method 730 includes a block 732 in which the computer 600 receives joint force data from the sensor module 12. Again, the joint force data is indicative of the joint force of the patient's knee as indicated by the sensor signals generated by the sensor array 90 of the sensor module 12. In block 734, the computer 600 determines the medial, lateral, and/or average joint force values based on the joint force data received in block 732.

Contemporaneously with the determination of the joint force values in block 732, the computer 600 determines the flexion angle of the patient's knee in block 736. To do so, the computer 600 determines the relative location of the patient's tibia and femur and determines the flexion angle defined therebetween based on these locations. In block 738, the computer 600 stores the joint force data determined in block 734 and the flexion angle data determined in block 738. The method repeats through blocks 732, 734, 736 to collect data and each, or every predetermined, flexion angle within a desired range of flexion. After such data has been collected, the method 730 advances to block 740 in which the computer 600 displays a graph of joint force values versus flexion angle. Such graph may include medial and lateral joint force values or may include an average joint force values depending on the preference of the orthopaedic surgeon.

Figure 32:
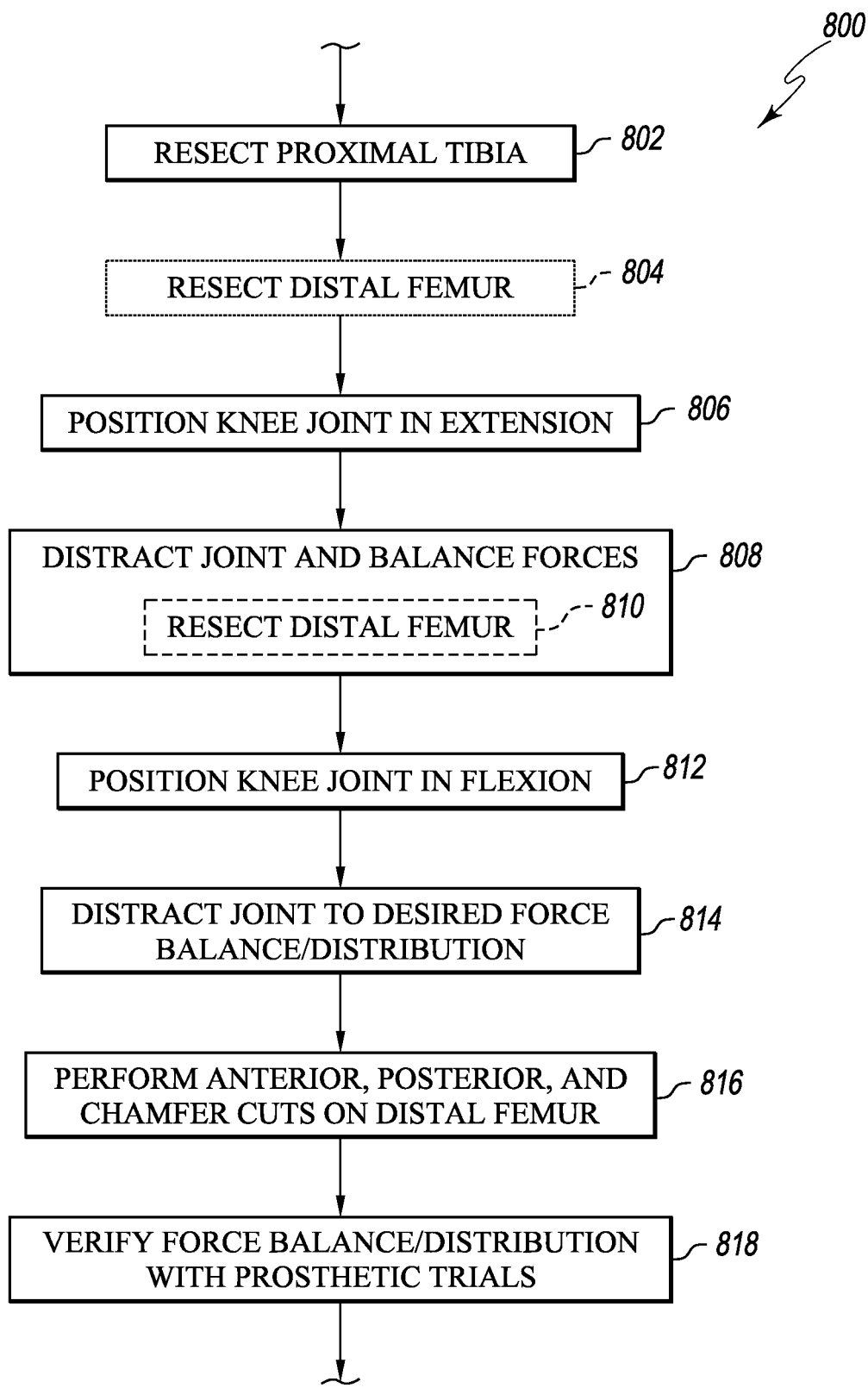
FIG. 32 is a simplified flow diagram of one embodiment of a method for performing an orthopaedic surgical procedure using the system of FIG. 1.

Referring now to FIGS. 32-37, as discussed above, the sensor module 12 may be used during the performance of an orthopaedic surgical procedure to monitor the relative medial-lateral balance of the patient's joint forces. For example, a surgical method 800 for performing a total knee arthroplasty procedure using the sensor module 12 is illustrated in FIG. 32. The method 800 begins with block 802 in which the proximal tibia 900 of the patient is resected. By resecting the patient's tibia 900, a resected planar surface or plateau is established on the proximal end of the tibia. In some embodiments, such as those embodiments wherein the computer assisted orthopaedic surgery (CAOS) system 18 is not used, the distal end of the patient's femur 902 may be resected in block 804.

Figure 33:
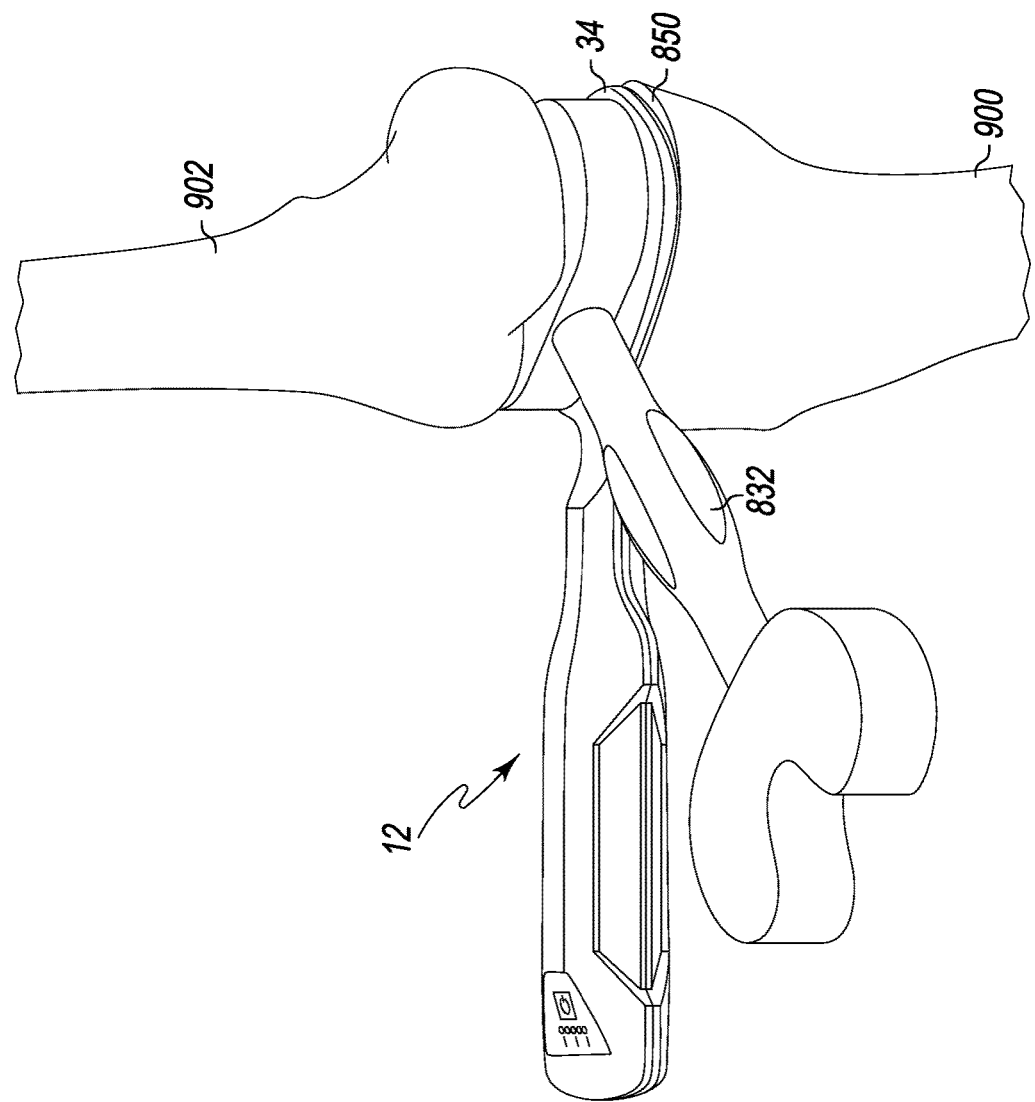
FIG. 33 is a perspective view of a patient's joint in extension during an orthopaedic surgical procedure using the sensor module of FIG. 2.

In block 806, the patient's knee is placed in extension. Subsequently, in block 808, the patient's knee is distracted while in extension and the joint forces are balanced. To do so, the orthopaedic surgeon may place the tibial paddle 34 of the sensor module 12 in the patient's knee joint. In particular, the tibial paddle 34 is placed on the resected plateau 850 of the patient's proximal tibia as illustrated in FIG. 33. The tibial paddle 34 may be placed in contact with the patient's tibia or may be placed on a membrane or other intervening member. As shown in FIG. 33, a spacer block 832 may be used to distract the patient's knee in extension a desired amount, which may be coupled to the sensor module 12 via the upper retainer clips 516 of the adaptor 502 in some embodiments. Alternatively, the sensor module 12 may be coupled to the joint distractor 16, which may be inserted into the patient's knee joint and operated to distract the joint to the desired amount. Typically, the patient's knee joint is distracted in extension an amount necessary to establish a generally rectangular joint gap (i.e., the resected plateau 850 of the patient's tibia is approximately parallel with the resected distal end of the patient's femur).

Once a generally rectangular joint gap is established, the orthopaedic surgeon may balance the medial and lateral joint forces. To do so, the orthopaedic surgeon may perform a ligament release or balancing procedure to reduce the medial or lateral force of the patient's knee. While so doing, the orthopaedic surgeon may monitor the display 50, 52 of the sensor module 12 and/or the hand-held display module 14 to determine which side to release and when the medial and lateral forces are approximately equal (e.g., when the middle light emitting diode 84 is illuminated). Of course, the orthopaedic surgeon may decide that an alternative joint force balance, such as a 45%-55% medial-lateral joint force balance, is desirable for the particular patient based on such criteria as, for example, the age of the patient, the gender of the patient, the extent of soft tissue damage of the patient's joint, the extent of pre-operative deformity of the patient's joint, etc. Additionally, in some embodiments, such as those embodiments wherein the computer assisted orthopaedic surgery (CAOS) system 18 is used, the distal end of the patient's femur 902 may be resected in block 810.

After the orthopaedic surgeon has properly balanced the medial-lateral joint forces of the patient's joint in extension, the patient's joint is placed in flexion in block 812. Subsequently, in block 814, the patient's knee is distracted while in flexion to the desired balance of joint forces. To do so, the orthopaedic surgeon may again place the tibial paddle 34 of the sensor module 12 on the resected plateau 850 of the patient's proximal tibia 900. The tibial paddle 34 may be placed in contact with the patient's tibia or may be placed on a membrane or other intervening member. The orthopaedic surgeon may distract the patient's knee using, for example, the distractor 16, or other distractor to distract each condyle of the patient's femur differing amounts until the medial and lateral joint forces are approximately equal. By, equalizing the medial and lateral joint forces, the rotation of the femur is established.

After the patient's joint has been distracted to achieve the desired medial-lateral joint balance in block 814, a number of additional resectioning cuts are performed on the patient's distal femur 902 in block 816. To do so, as illustrated in FIG. 34, a cutting block 860 may be coupled to the joint distractor 16 and used to perform an anterior femoral cut, a posterior femoral cut, and/or chamfer cuts on the patient's distal femur 902 while the patient's joint is distracted in flexion. In one particular embodiment, the cutting block 860 is positioned such that the anterior and posterior femoral cuts are substantially parallel to the tibial cut while the patient's knee is distracted in flexion as discussed above. In other embodiments, the cutting block 860 may be positioned such that the angle of the anterior and posterior femoral cuts correspond to particular angles of the intended implant. As such, the anterior and posterior femoral cuts are performed with the femur rotated to the desired position. The position of the cutting block 860 may also be adjusted anteriorly or posteriorly to set the flexion gap for the orthopaedic implant.

Alternatively, in some embodiments, the rotation of the femur in flexion is predetermined based on anatomical references such as the posterior condyles, Whiteside's line, and/or the transepicondylar axis. The anterior femoral cut, a posterior femoral cut, and/or chamfer cuts are performed on the patient's distal femur 902 based on the predetermined rotation of the femur. As illustrated in FIG. 35, a spacer block 854 may be used to check or verify such femoral cuts. Additionally, ligamentous release may be used by the surgeon to balance or define the desired medial-lateral joint forces. In such embodiments, the orthopaedic surgeon may also verify that ligament releases performed in flexion do not adversely affect the joint force balance in extension.

Figure 36:
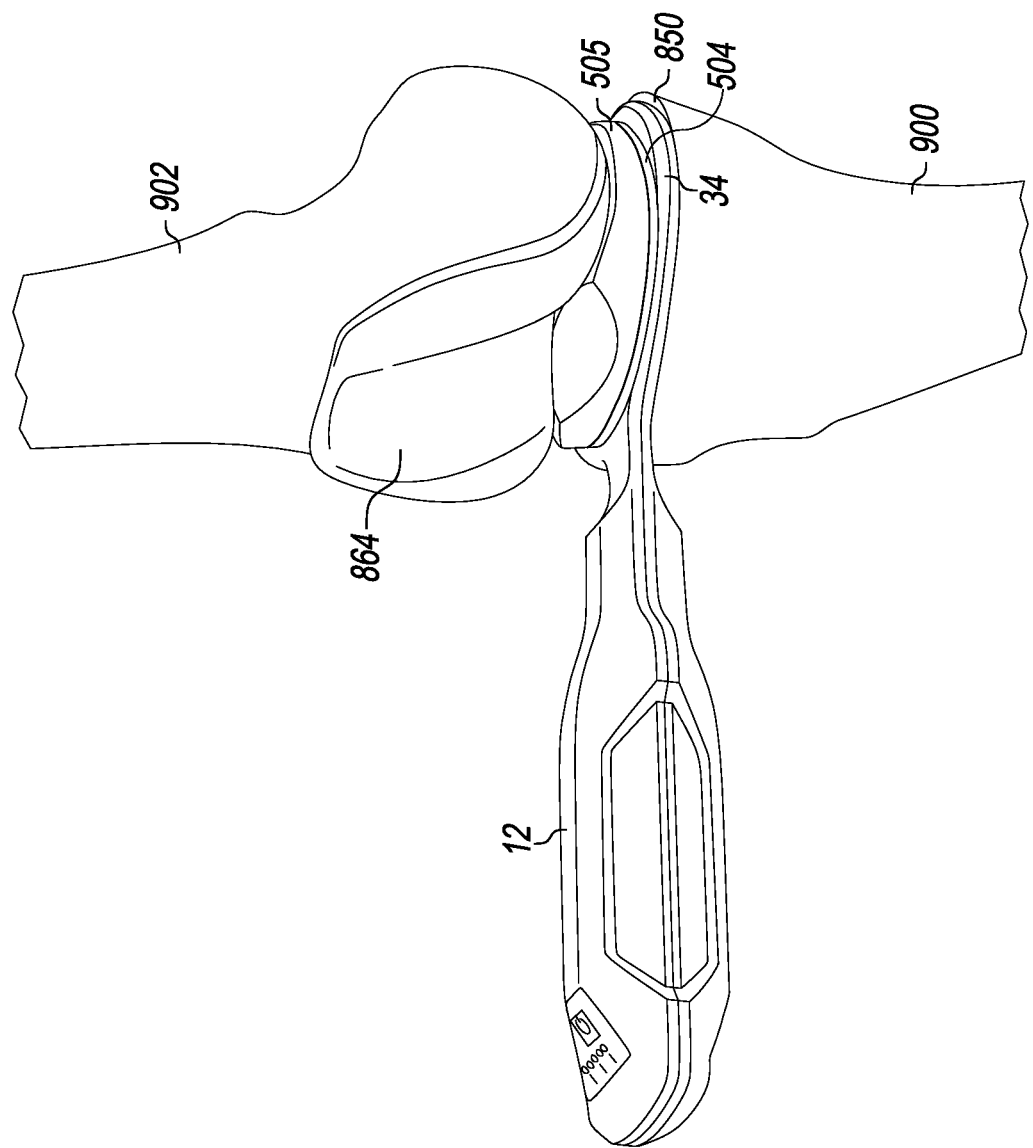
FIG. 36 is another perspective view of a patient's joint in extension during an orthopaedic surgical procedure using the sensor module of FIG. 2.
Figure 37:
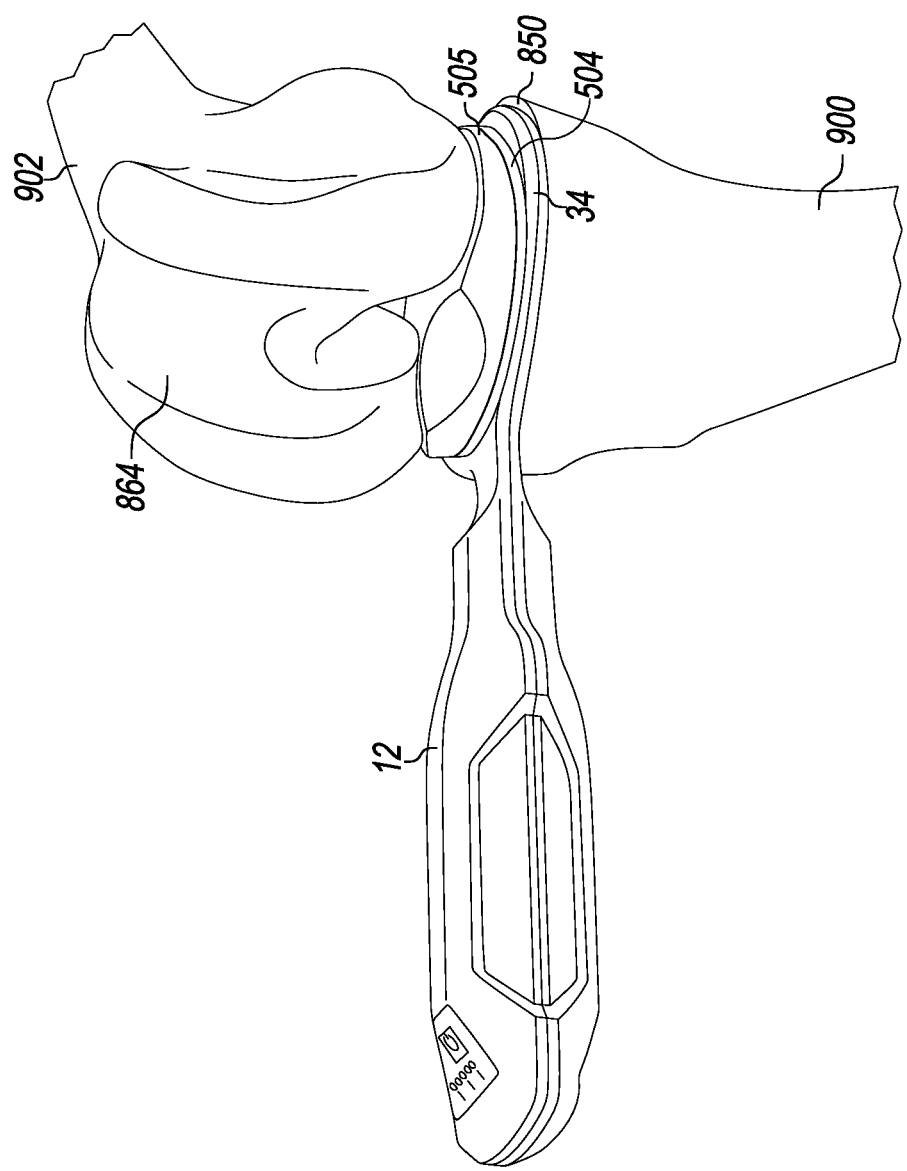
FIG. 37 is another perspective view of a patient's joint in flexion during an orthopaedic surgical procedure using the sensor module of FIG. 2.

After the final resectioning of the patient's distal femur is complete, the joint force balance of the patient's knee joint is verified in block 818. To do so, the orthopaedic surgeon may utilize the tibial trialing system 500 described above with regard to FIGS. 19-27. For example, as illustrated in FIGS. 36 and 37, a trialing shim 504 may be positioned over the adaptor 502 on the sensor module 12, and a tibial surface trial 505 may be secured to the trialing shim 504. A trial femoral component 864 may also be temporarily coupled to the distal end of the patient's femur 902. The patient's knee joint may then be moved through various degrees of flexion as illustrated in FIG. 37 while the orthopaedic surgeon monitors the associated joint force balance as indicated by the displays 50, 52 of the sensor module 12 or the display 302 of the display module 14 to verify that the desired joint force balance is maintained throughout flexion of the patient's joint. It should be appreciated that the trialing shim 504 may be arranged on the tibial paddle 34 of the sensor module 12 in either the fixed trialing orientation or mobile trialing orientation, as described above in regard to FIGS. 23-25. In other embodiments, a fixed or mobile tibial bearing trial 506 may be used with the adaptor 502 and sensor module 12.

The system 10 has been described above in regard to the measuring, determining, and displaying of joint forces. Such joint forces generally correspond to the joint pressure of the patient's joint over a defined area. As such, it should be appreciated that in other embodiments the sensor module 12, the hand-held display module 14, and the computer assisted surgery system 18 may be configured to measure, determine, and display the pressure of the patient's relative joint in addition to or alternatively to the patient's joint force. For example, in one embodiment, the pressure of the patient's joint may be determined based on the known area of each sensor of the pressure sensors or sensor elements 100 of the sensor array 90.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the devices, systems, and methods described herein. It will be noted that alternative embodiments of the devices, systems, and methods of the present disclosure may not include all of the features described yet still benefit from at least some of the advantages of such features. Those of ordinary skill in the art may readily devise their own implementations of the devices, systems, and methods that incorporate one or more of the features of the present invention and fall within the spirit and scope of the present disclosure as defined by the appended claims.

The invention claimed is:

1. A surgical instrument for coupling a tibial trialing component to a tibial paddle of a sensor module, the surgical instrument comprising:
a central hub having a top side and a bottom side,
a plurality of lower retainer clips sized to be received in an aperture of the tibial paddle of the sensor module, each lower retainer clip of the plurality of lower retainer clips comprising (i) a stem extending downwardly from the bottom side of the central hub and (ii) a lip extending outwardly from a distal end of the stem of the lower retainer clip,
a plurality of upper retainer clips sized such that the plurality upper retainer clips is not receivable within the aperture of the tibial paddle, each upper retainer clip of the plurality of upper retainer clips comprising (i) a stem extending upwardly from the top side of the central hub and (ii) a lip extending outwardly from a distal end of the stem of the upper retainer clip,
a first alignment tab extending downwardly from the bottom side of the central hub, and
a second alignment tab extending downwardly from the bottom side of the central hub, the second alignment tab having an arc length greater than an arc length of the first alignment tab.

2. The surgical instrument of claim 1, wherein the plurality of lower retainer clips are configured to flex to allow the surgical instrument to attach to and detach from the tibial paddle.

3. The surgical instrument of claim 1, wherein each of the first alignment tab and the second alignment tab comprises a first angled sidewall and a second angled sidewall, wherein each of the first angled sidewall and the second angled sidewall is configured to cooperate with an angle surface of the tibial paddle to provide a lift-off force to detach the surgical instrument from the tibial paddle in response to a reference amount of torque being applied to the surgical instrument.

4. The surgical instrument of claim 3, wherein the plurality of lower retainer clips are configured to flex inwardly in response to the lift-off force provided by at least one of the first angled sidewall and the second angled sidewall to detach the surgical instrument from the tibial paddle.

5. The surgical instrument of claim 4, wherein the first angled sidewall and the second angled sidewall of the first alignment tab have opposite slopes, and wherein the first angled sidewall and the second angled sidewall of the second alignment tab have opposite slopes.

6. The surgical instrument of claim 1, wherein the surgical instrument includes an anti-rotation protrusion configured to prevent rotation of the surgical instrument relative to the tibial paddle, the anti-rotation protrusion extending outwardly from the central hub along an axis that is parallel to a plane defined by the tibial paddle when the tibial paddle is coupled to the surgical instrument.

7. The surgical instrument of claim 6, wherein the anti-rotation protrusion is configured to be positioned in a first aperture of the tibial trialing component to prevent rotation of the tibial trialing component relative to the tibial paddle.

8. The surgical instrument of claim 7, wherein the anti-rotation protrusion is configured to be positioned in a second aperture of the tibial trialing component to provide a limited range of rotation of the tibial trialing component relative to the tibial paddle.

9. The surgical instrument of claim 1, wherein each lower retainer clip of the plurality of lower retainer clips is inwardly curved when viewed in a transverse plane that is parallel to a plane defined by the tibial paddle when the tibial paddle is coupled to the surgical instrument.

10. The surgical instrument of claim 1, wherein the plurality of lower retainer clips are arranged to generally define a circle when viewed in a transverse plane that is parallel to a plane defined by the tibial paddle when the tibial paddle is coupled to the surgical instrument.

11. The surgical instrument of claim 1, wherein each of the first alignment tab and the second alignment tab are inwardly curved when viewed in a transverse plane that is parallel to a plane defined by the tibial paddle when the tibial paddle is coupled to the surgical instrument.

12. A method of determining a joint force of a patient's knee joint, the method comprising:
aligning a plurality of lower retainer clips extending downwardly from a hub of a surgical instrument with an aperture of a tibial paddle of a sensor module,
inserting the plurality of lower retainer clips of the surgical instrument into the aperture of the tibial paddle to secure the surgical instrument to the tibial paddle, and positioning the tibial paddle having the surgical instrument secured thereto between a proximal end of a patient's tibia and a distal end of a patient's femur to allow a sensor array positioned in the tibial paddle of the sensor module to generate sensor signals indicative of a joint force between the proximal end of the patient's tibia and the distal end of the patient's femur.

13. The method of claim 12, further comprising positioning a tibial trialing component over the surgical instrument in a first orientation that prevents rotation of the tibial trialing component relative to the tibial paddle.

14. The method of claim 13, wherein positioning the tibial trialing component over the surgical instrument in the first orientation comprises positioning an anti-rotation protrusion extending from the hub of the surgical instrument in a first aperture of the tibial trialing component.

15. The method of claim 14, further comprising positioning the tibial trialing component over the surgical instrument in a second orientation that provides a limited range of rotation of the tibial trialing component relative to the tibial paddle.

16. The method of claim 15, wherein positioning the tibial trialing component over the surgical instrument in the second orientation comprises positioning the anti-rotation protrusion in a second aperture of the tibial trialing component.

17. The method of claim 16, wherein positioning the tibial trialing component over the surgical instrument in the first orientation and positioning the tibial trialing component over the surgical instrument in the second orientation each comprise:
   aligning a central aperture of the tibial trialing component with the hub of the surgical instrument, the central aperture of the tibial trialing component being in fluid communication with the first aperture and the second aperture of the tibial trialing component, and
   inserting the hub of the surgical instrument into the central aperture of the tibial trialing component.

18. The method of claim 12, further comprising securing an additional surgical instrument to the surgical instrument prior to positioning the tibial paddle between the proximal end of the patient's tibia and the distal end of the patient's femur such that positioning the tibial paddle between the proximal end of the patient's tibia and the distal end of the patient's femur distracts the patient's knee joint.

19. The method of claim 18, wherein securing the additional surgical instrument to the surgical instrument comprises inserting a plurality of upper retainer clips of the surgical instrument into an aperture of the second surgical instrument.

20. The method of claim 12, further comprising rotating the patient's knee joint into flexion such that the sensor signals generated by the sensor array of the sensor module are indicative of joint force values versus flexion angles.

* * * * *